(12) United States Patent
Jensen et al.

(10) Patent No.: US 12,098,208 B2
(45) Date of Patent: *Sep. 24, 2024

(54) EARLY INTERVENTION METHODS TO PREVENT OR AMELIORATE TOXICITY

(71) Applicant: Seattle Children's Hospital, Seattle, WA (US)

(72) Inventors: Michael C. Jensen, Bainbridge Island, WA (US); Rebecca Gardner, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/329,987

(22) Filed: Jun. 6, 2023

(65) Prior Publication Data

US 2023/0322937 A1 Oct. 12, 2023

Related U.S. Application Data

(63) Continuation of application No. 18/061,196, filed on Dec. 2, 2022, now Pat. No. 11,760,804, which is a continuation of application No. 16/087,488, filed as application No. PCT/US2017/023676 on Mar. 22, 2017, now Pat. No. 11,518,814.

(60) Provisional application No. 62/429,722, filed on Dec. 2, 2016, provisional application No. 62/417,287, filed on Nov. 3, 2016, provisional application No. 62/311,906, filed on Mar. 22, 2016.

(51) Int. Cl.
| C07K 16/28 | (2006.01) |
| A61K 9/00 | (2006.01) |
| A61K 39/00 | (2006.01) |
| A61P 35/02 | (2006.01) |

(52) U.S. Cl.
CPC ........ *C07K 16/2866* (2013.01); *A61K 9/0019* (2013.01); *A61K 9/0053* (2013.01); *A61P 35/02* (2018.01); *A61K 2039/505* (2013.01); *C07K 2319/03* (2013.01)

(58) Field of Classification Search
CPC ....................... A61K 39/3955; C07K 16/2866
See application file for complete search history.

(56) References Cited

U.S. PATENT DOCUMENTS

| 4,235,871 A | 11/1980 | Papahadjopoulos et al. |
| 4,452,773 A | 6/1984 | Molday |
| 4,501,728 A | 2/1985 | Geho et al. |
| 4,690,915 A | 9/1987 | Rosenberg |
| 4,795,698 A | 1/1989 | Owen et al. |
| 4,837,028 A | 6/1989 | Allen |
| 5,019,369 A | 5/1991 | Presant et al. |
| 5,087,616 A | 2/1992 | Myers et al. |
| 5,200,084 A | 4/1993 | Liberti et al. |
| 5,219,740 A | 6/1993 | Miller et al. |
| 5,591,827 A | 1/1997 | Brakenhoff et al. |
| 6,030,615 A | 2/2000 | Bucala |
| 6,040,177 A | 3/2000 | Riddell et al. |
| 6,207,453 B1 | 3/2001 | Maass et al. |
| 6,410,319 B1 | 6/2002 | Raubitschek et al. |
| 6,451,995 B1 | 9/2002 | Cheung et al. |
| 7,070,995 B2 | 7/2006 | Jensen |
| 7,265,209 B2 | 9/2007 | Jensen |
| 7,354,762 B2 | 4/2008 | Jensen |
| 7,446,179 B2 | 11/2008 | Jensen et al. |
| 7,446,190 B2 | 11/2008 | Sadelain et al. |
| 7,446,191 B2 | 11/2008 | Jensen |
| 8,324,353 B2 | 12/2012 | Jensen |
| 8,339,645 B2 | 12/2012 | Nakawaki |
| 8,389,282 B2 | 3/2013 | Sadelain et al. |
| 8,479,118 B2 | 7/2013 | Lyndersay et al. |
| 8,562,991 B2 | 10/2013 | Igawa et al. |
| 8,802,374 B2 | 8/2014 | Jensen |
| 8,822,647 B2 | 9/2014 | Jensen |
| 8,911,993 B2 | 12/2014 | June et al. |
| 11,518,814 B2 | 12/2022 | Jensen et al. |
| 2002/0131960 A1 | 9/2002 | Sadelain et al. |
| 2003/0170238 A1 | 9/2003 | Gruenberg et al. |

(Continued)

FOREIGN PATENT DOCUMENTS

| EP | 0 452 342 | 11/1994 |
| EP | 2 537 416 | 11/2014 |

(Continued)

OTHER PUBLICATIONS

Maude et al. Cancer J. 2014; 20(2): 119-122 (Year: 2014).*
Lee et al. Blood. Jul. 10, 2014; 124(2): 188-195 (Year: 2014).*
Grupp et al. Blood, 2012; 120(21)) (Year: 2012).*
Davilla et al.Science Translational Medicine, 2014; 6(224): 224ra25) (Year: 2014).*
Grupp et al. Chimeric Antigen Receptor-Modified T Cells for Acute Lymphoid Leukemia. N Engl J Med 2013;368:1509-18 (Year: 2013).*
Aagaard et al. RNAi therapeutics: Principles, prospects and challenges. Advanced Drug Delivery Reviews 59 (2007) 75-86 (Year: 2007).
Ali et al., Sep. 29, 2016, T cells expressing and anti-B-cell maturation antigen chimeric antigen receptor cause remissions of multiple myeloma, Blood, 128(13):1688-1700.

(Continued)

*Primary Examiner* — Vanessa L. Ford
*Assistant Examiner* — Sandra Carter
(74) *Attorney, Agent, or Firm* — Knobbe, Martens, Olson & Bear LLP

(57) ABSTRACT

Provided are methods for preventing or ameliorating toxicity caused by or due to a therapy, such as an immunotherapy or a cell therapy, by pre-emptive or early administration toxicity-targeting agent(s). In some embodiments, the therapy is a cell therapy in which the cells generally express recombinant receptors such as chimeric receptors, e.g., chimeric antigen receptors (CARs) or other transgenic receptors such as T cell receptors (TCRs). Features of the methods, including the timing of the administration of the agents or treatments for toxicity, provide various advantages, such as lower toxicity while maintaining persistence and efficacy of the administered cells.

20 Claims, 6 Drawing Sheets

Specification includes a Sequence Listing.

(56) References Cited

U.S. PATENT DOCUMENTS

| | | |
|---|---|---|
| 2009/0175879 A1 | 7/2009 | Utku |
| 2011/0003380 A1 | 1/2011 | Miltenyi et al. |
| 2013/0149337 A1 | 6/2013 | Cooper et al. |
| 2013/0287748 A1 | 10/2013 | June et al. |
| 2014/0271635 A1 | 9/2014 | Brogdon et al. |
| 2015/0202286 A1 | 7/2015 | June |
| 2023/0091447 A1 | 3/2023 | Jensen |
| 2023/0212298 A1 | 7/2023 | Jensen |

FOREIGN PATENT DOCUMENTS

| | | |
|---|---|---|
| WO | WO 92/008796 | 5/1992 |
| WO | WO 94/028143 | 12/1994 |
| WO | WO 00/14257 | 3/2000 |
| WO | WO 10/033140 | 3/2009 |
| WO | WO 09/072003 | 6/2009 |
| WO | WO 12/035141 | 3/2012 |
| WO | WO 12/129514 | 9/2012 |
| WO | WO 13/071154 | 5/2013 |
| WO | WO 13/123061 | 8/2013 |
| WO | WO 13/126726 | 8/2013 |
| WO | WO 13/166321 | 11/2013 |
| WO | WO 14/011984 | 1/2014 |
| WO | WO 14/031687 | 2/2014 |
| WO | WO 14/055668 | 4/2014 |
| WO | WO 16/132366 | 8/2016 |
| WO | WO 17/035362 | 3/2017 |
| WO | WO 17/040930 | 3/2017 |
| WO | WO 18/013918 | 1/2018 |

OTHER PUBLICATIONS

Alonso-Camino et al., "CARbodies: Human Antibodies Against Cell Surface Tumor Antigens Selected From Repertoires Displayed on T Cell Chimeric Antigen Receptors," Mol Ther ucleic Acids (2013) 2(5):e93.

Annex to the ED's communication on EP 3 433 276, Jun. 10, 2019, 7 pp.

Barret et al., "Chimeric Antigen Receptor Therapy for Cancer," Annual Review of Medicine (2014) 65:333-347.

Barrett et al., Feb. 2014, Toxicity management for patients receiving novel T-cell engaging therapies, Curr Opin Pedatr., 26(1):43-49.

Baum et al., "Retrovirus Vectors: Toward the Plentivirus?" Mol Ther (2006) 13(6):1050-1063.

Bonifant et al., 2016, Toxicity and managemetn in CAR T-cell therapy, Molecular Therapy Oncolytics, 3, 16011.

Boris-Lawrie., "Recent advances in retrovirus vector technology," Curr Opin Genet (1993) 3:102-109.

Bork. Powers and Pitfalls in Sequence Analysis: The 70% Hurdle. Genome Research, 2000, 10:398-400 (Year: 2000).

Bowie et al. Deciphering the Message in Protein Sequences: Tolerance to Amino Acid Substitutions. Science, 1990, 247:1306-1310 (Year: 1990).

Brash et al., "Strontium phosphate transfection of human cells in primary culture: stable expression of the simian virus 40 large-T-antigen gene in primary human bronchial epithelial cells," Mol Cell Biol (1987) 7:2031-2034.

Brentjens et al., "CD19-targeted T cells rapidly induce molecular remissions in adults with chemotherapy-refractory acute lymphoblastic leukemia," Sci Transl Med (2013) 5(177):177ra38.

British National Formulary (BNF) 37 (Mar. 1999) Glucocorticoid therapy, pp. 316-323.

Brown et al. Tolerance to Single, but Not Multiple, Amino Acid Replacements in Antibody VH CDR2. J Immunol. May 1996; 156(9): 3285-91 (Year: 1996).

Brudno et al., Jun. 30, 2016, Toxicities of chimeric antigen receptor T cells: recognition and management, Blood, 127(26):3321-3330.

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).

Burns et al., "Vesicular stomatitis virus G glycoprotein pseudotyped retroviral vectors: concentration to very high titer and efficient gene transfer into mammalian and nonmammalian cells," PNAS (1993) 90(17):8033-8037.

Carlens et al., "Ex vivo T lymphocyte expansion for retroviral transduction: influence of serum-free media on variations in cell expansion rates and lymphocyte subset distribution," Exp Hematol (2000) 28(10):1137-1146.

Cavaletti et al., "Chemotherapy-induced peripheral neurotoxicity," Nature Reviews Neurology (2010) 6:657-666.

Cavalieri et al., "Human T lymphocytes transduced by lentiviral vectors in the absence of TCR activation maintain an intact immune competence," Blood (2003) 102(2):497-505.

Cheadle et al., "Chimeric antigen receptors for T-cell based therapy," Methods Mol Biol (2012) 907:645-666.

Chicaybam et al., "An Efficient Low Cost Method for Gene Transfer to T Lymphocytes," PLoS One (2013) 8(3):e60298.

Cho et al., "Human mammalian cell sorting using a highly integrated micro-fabricated fluorescence-activated cell sorter (μFACS)," Lap Chip (2010) 10:1567-1573.

Cho et al., "Rapid identification of cytokine release syndrome after haploidentical PBSC transplantation and successful therapy with tocilizumab," Bone Marrow Transplantation (2016) 51: 1620-1621.

Clark et al. Discovery and Development of Janus Kinase (JAK) Inhibitors for Inflammatory Diseases. J. Med. Chem., 2014, 57 (12), pp. 5023-5038 (Year: 2014).

Clarke et al., "Immunomagnetic Cell Separation," Chapter 2, pp. 17-23 of Metastasis Research Protocols, vol. II: Analysis of Cell Behavior In Vitro and In Vivo, Methods in Molecular Medicine™ Edited by: S.A. Brooks and U. Schumacher © 2001 Humana Press Inc., Totowa, NJ.

Clinicaltrials.gov, submitted date Sep. 28, 2016 (v2), History of changes for study: NCT02906371, Study of the tocilizumab optimization timing for CART19 associated cytokine release syndrome, 12 pp.

Clinicaltrials.gov., submitted Feb. 15, 2022, History of changes for study: NCT02028455, A pediatric and young adult trial of genetically modified T cells directed against CD19 for relapsed/refractory CD19+ leukemia, 12 pp.

Cohen et al., "Recognition of Fresh Human Tumor by Human Peripheral Blood Lymphocytes Transduced with a Bicistronic Retroviral Vector Encoding a Murine Anti-p53 TCR," J Immunol (2005) 175:5799-5808.

Cooper et al., "T-cell clones can be rendered specific for CD19: toward the selective augmentation of the graft-versus-B-lineage leukemia effect," Blood (2003) 101:1637-1644.

Current Protocols in Molecular Biology, vol. 1 (© 2010) John Wiley & Sons, Inc., New York, NY, Table of Contents, 15 pages.

Davila et al., "CD19 CAR-Targeted T Cells Induce Long-Term Remission and B Cell Aplasia in an Immunocompetent Mouse Model of B Cell Acute Lymphoblastic Leukemia," PLoS One (2013) 8(4):e61338.

Davila et al., "CD19-Targeted T Cells for Hematologic Malignancies: Clinical Experience to Date," Cancer J. Nov.-Dec. 2015;21(6):470-4.

Davila et al., "Efficacy and Toxicity Management of 19-28z CAR T Cell Therapy in B Cell Acute Lymphoblastic Leukemia," Sci Transl Med (2014) 6(224):224ra25.

Davilla et al. Efficacy and Toxicity Management of 19-29z CART Cell Therapy in B Cells Acute Lymphoblastic Leukemia. Science Translational Medicine, 2014; 6(224): 224ra25 (Year: 2014).

Del Bene, 1990, Chapter 218: Temperature, in Clinical Methods: the History, Physical, and Laboratory Examinations, 3rd edition, pp. 990-993.

Dobber et al., "The in vivo effects of neutralizing antibodies against IFN-gamma, IL-4, or IL-10 on the humoral immune response in young and aged mice," Cell Immunol (1995) 160(2):185-192.

Fedorov et al., "PD-1- and CTLA-4-Based Inhibitory Chimeric Antigen Receptors (iCARs) Divert Off-Target Immunotherapy Responses," Science Translational Medicine (2013) 5(215):215ra172.

(56) References Cited

OTHER PUBLICATIONS

Frecha et al., "Advances in the Field of Lentivector-based Transduction of T and B Lymphocytes for Gene Therpy," Mol Ther (2010) 18(10):1748-1757.
Frey et al., 2016, Cytokine release syndrome with novel therapeutics for acute lymphoblastic leukemia, Hematology, pp. 567-572.
Gardner et al. "CD19 CAR-T Cell Products of Defined CD4:CD8 Composition and Transgene Expression Show Prolonged Persistence and Durable MRD-Negative Remission in Pediatric and Young Adult B-Cell ALL" Presented at ASH. 2016 Blood (2016) 128:219.
Gardner et al., "CD19 CAR-T Cell Products of Defined CD4:CD8 Composition and Transgene Expression Show Prolonged Persistence and Durable MRD-Negative Remission in Pediatric and Young Adult B-Cell ALL," Presented at ASH, San Diego, CA on Dec. 3, 2016. Presentation. 15 pages.
Gardner et al., "Decreased Rates of Severe CRS Seen with Early Intervention Strategies for CD19 CAR-T Cell Toxicity Management," ASH 2016, Blood (2016) 128:586.
Gardner et al., "Decreased Rates of Severe CRS Seen with Early Intervention Strategies for CD19 CAR-T Cell Toxicity Management," Presented at ASH, San Diego, CA on Dec. 5, 2016. Presentation. 17 pages.
Gardner et al., Dec. 12, 2019, Preemptive mitigation of CD19 CAR T-cell cytokine release syndrome without attenuation of antileukemic efficacy, Immunobiology and Immunotherapy, 124(24):2149-2158.
Gardner et al., Jun. 22, 2017, Intent-to-treat leukemia remission by CD19 CAR T cells of defined formulation and dose in children and young adults, Blood, 129(25):3322-3331.
Genentech Inc., Oct. 2013, Actemra prescribing information, 40 pp.
Gibney, Apr. 21, 2015, Seattle Children's pediatric leukemia adoptive therapy (PLAT-02) clinical trial boasts 91% complete remission rate in children with relapsed leukemia, PR Newswire press release, 3 pp.
Godin et al., "Microfluidics and photonics for Bio-System-on-a-Chip: a review of advancements in technology towards a microfluidic flow cytometry chip," J Biophotonics (2008) 1(5):355-376.
Gong et al., "An Antagonist of Monocyte Chemoattractant Protein 1 (MCP-1) Inhibits Arthritis in the MRL-lpr Mouse Model," J Exp Med (1997) 186(1):131-137.
Grupp et al. CD19-redirected chimeric antigen receptor t (CART19) cells induce a cytokine release syndrome (CRS) and induction of treatable macrophage activation syndrome (MAS) that can be managed by the IL-6 antagonist tocilizumab (TOC). Blood, 2012; 120(21)) (Year: 2012).
Grupp et al., "Advances in T-cell therapy for ALL," Best Pract Res Clin Haematol. Sep.-Dec. 2014;27(3-4):222-228.
Grupp et al., "Chimeric antigen receptor-modified T cells for acute lymphoid leukemia," N Engl J Med. Apr. 18, 2013;368(16):1509-1518.
Guido et al. Virtual Screening and Its Integration with Modern Drug Design Technologies. Curr Med Chem. 2008; 15(1):37-46) (Year: 2008).
Gust et al., Dec. 2017, Endothelial activation and blood-brain barrier disruption in neurotoxicity after adoptive immunotherapy with CD19 CAR-T cells, Cancer Discov., 7(12):1404-1419.
Hackett et al., "A transposon and transposase system for human application," Mol Ther (2010) 18(4):674-683.
Hannum et al., "Interleukin-1 receptor antagonist activity of a human interleukin-1 inhibitor," Nature (1990) 343:336-340.
Hermans et al., "The VITAL assay: a versatile fluorometric technique for assessing CTL- and NKT-mediated cytotoxicity against multiple targets in vitro and in vivo," J Immunol Methods (2004) 285(1):25-40.
Huang et al., "DNA transposons for modification of human primary T lymphocytes," Methods Mol Biol (2009) 506:115-126.
Hudecek et al., "Receptor affinity and extracellular domain modifications affect tumor recognition by ROR1-specific chimeric antigen receptor T cells," Clin Cancer Res (2013) 19(12):3153-3164.

Hunter et al., "Neutralizing anti-IL-10 antibody blocks the protective effect of tapeworm infection in a murine model of chemically induced colitis," J Immunol (2005) 174(11):7368-7375.
Jensen et al., 2015, CIPO 2015 Conference archives: 4th International Conference on Immunotherapy in Pediatric Oncology, https://web.archive.org/web/20160228223342/http://www.seattlechildrens.org:80/research/childhood-cancer/cipo-2015/, 4 pp.
Jensen, 2015, Enhancing the IQ of CAR T cells using the synthetic biology tool box, Jensen Lab, PowerPoint presentation, 39 pp.
Jensen, 2016, Present experience and enhanced engineering of CAR T cell therapy for B-cell malignancies, PowerPoint presentation, 48 pp.
Johnston et al., "Biolistic transformation: microbes to mice," Nature (1990) 346:776-777.
Johnston, S.A., "Biolistic transformation: microbes to mice," Nature (London) (1990) vol. 346, No. 6286, pp. 776-777.
Jun et al., Feb. 2015, Cytokine Release Syndrome Occurrence mechanism and prevention policy slightly, Cancer Research and Clinic, 27(2):135-139.
Kang et al., "Therapeutic uses of anti-interleukin-6 receptor antibody," Int Immunol. Jan. 2014;27(1):21-9.
Klebanoff et al., "Sorting through subsets: Which T cell populations mediate highly effective adoptive immunotherapy?" J Immunother (2012) 35(9):651-660.
Kochenderfer et al., "B-cell depletion and remissions of malignancy along with cytokine-associated toxicity in a clinical trial of anti-CD19 chimeric-antigen-receptor-transduced T cells," Blood (2012) 119:2709-2720.
Kochenderfer et al., "Construction and preclinical evaluation of an anti-CD19 chimeric antigen receptor," J Immunother (2009( 32(7):689-702.
Kochenderfer et al., "Treating B-cell cancer with T cells expressing anti-CD19 chimeric antigen receptors," Nat Rev Clin Oncol (2013) 10(5):267-276.
Koste et al., "T-cell receptor transfer into human T cells with ecotropic retroviral vectors," Gene Therapy (2014) 21:533-538.
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).
Lee et al., "Current Concepts in the Diagnosis and Management of Cytokine Release Syndrome," Blood (2014) 124(2): 188-195.
Lee et al., Feb. 7, 2015, T cells expressing CD19 chimeric antigen receptors for acute lymphoblastic leukaemia in children and young adults: a phase 1 dose-escalation trial, The Lancet, 385:517-528.
Li et al., "Directed evolution of human T-cell receptors with picomolar affinities by phage display," Nat Biotechnol (2005) 23(3):349-354.
Lupton et al., "Dominant positive and negative selection using a hygromycin phosphotransferase-thymidine kinase fusion gene," Mol and Cell Biol (1991) 11(6):3374-3378.
Manuri et al., "piggyBac Transposon/Transposase System to Generate CD19-Specific T Cells for the Treatment of B-Lineage Malignancies," Hum Gene Ther (2010) 21(4):427-437.
Marofi et al., 2021, CAR T cells in solid tumors: challenges and opportunities, Stem Cell Research & Therapy, 12:81.
Marofi et al., 2021, Novel CAR T therapy is a ray of hope in the treatment of seriously ill AML patients, Stem Cell Research & Therapy, 12:465, 23 pp.
Maude et al., "Chimeric antigen receptor T cells for sustained remissions in leukemia," N Engl J Med. Oct. 16, 2014;371(16):1507-17.
Maude et al., "Managing Cytokine Release Syndrome Associated With Novel T Cell-Engaging Therapies," The Cancer Journal (2014) 20(2):119-122.
Maude et al., Jun. 25, 2015, CD19-targeted chimeric antigen receptor T-cell therapy for acute lymphoblastic leukemia, Blood, 125(26):4017-4023.
Maude et al., Mar./Apr. 2014, Managing cytokine release syndrome associated with novel T cell-engaging therapies, The Cancer Journal, 20(2):119-122.
Maude et al., Oct. 16, 2014, Chimeric antigen receptor T cells for sustained remissions in leukemia, The New England Journal of Medicine, 371:1507-1517.

(56) References Cited

OTHER PUBLICATIONS

Miller et al., "Improved retroviral vectors for gene transfer and expression," Biotechniques (1989) 7(9):980-982.

Miller et al., 2015, CD19-targeted CAR T cells: a new tool in the fight against B cell malignancies, Oncology Research and Treatment, 38:683-690.

Miller, "Retrovirus packaging cells," Hum Gene Ther (1990) 1(1):5-14.

Morris et al., Feb. 2022, Cytokine release syndrome and associate neurotoxicity in cancer immunotherapy, Nature Reviews Immunology, 22:85-96.

Mullen et al., "Transfer of the bacterial gene for cytosine deaminase to mammalian cells confers lethal sensitivity to 5-fluorocytosine: A negative selection system," Proc Natl Acad Sci U.S.A (1992) 89:33-37.

Nellan et al., Aug. 8, 2018, Improved CNS exposure to tocilizumab after cerebrospinal fluid compared to intravenous administration in rhesus macaques, Blood, 132(6):662-666.

Nellan et al., Nov. 2015, Paving the road ahead for CD19 CAR T-cell therapy, Hematology, 22(6):516-520.

Ozmen et al., "Mouse soluble IFN gamma receptor as IFN gamma inhibitor. Distribution, antigenicity, and activity after injection in mice," J Immunol (1993) 150(7):2698-2705.

Park et al., "Treating cancer with genetically engineered T cells," Trends Biotechnol (2011) 29(11):550-557.

Parkhurst et al., "Characterization of Genetically Modified T-Cell Receptors that Recognize the CEA:691-699 Peptide in the Context of HLA-A2.1 on Human Colorectal Cancer Cells," Clin Cancer Res (2009) 15(1):169-180.

Patel et al., "Cancer CARtography: charting out a new approach to cancer immunotherapy," Immunotherapy. (2014);6(6):675-8.

Patentee's letter to the EPO re: European patent application No. 17719044.4, dated May 14, 2019, 14 pp.

Peterson, Jan./Feb. 1995, Therapeutic potential for cytokine antagonists: thalidomide and pentoxifylline in Hansen's disease, Can J Infect Dis., 6(1):30-33.

Remington, The Science and Practice of Pharmacy (2011) $21^{st}$ Ed., Pharmaceutical Press, Royal Pharmaceutical Society, Table of Contents, 4 pages.

Remington's, Remington's Pharmaceutical Sciences (1980) 16th Ed, A. Osol, Ed. Mack Pub. Co., Easton, PA, Table of Contents, 4 pages.

Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant," Human Gene Therapy (1992) 3:319-338.

Rosenberg et al., "Cell transfer immunotherapy for metastatic solid cancer—what clinicians need to know," Nat Rev Clin Oncol (2011) 8(10):577-585.

Rotz et al., "Severe cytokine release syndrome in a patient receiving PD-1-directed therapy," Pediatr Blood Cancer. (2017) e26642.

Sadelain et al., "The basic principles of chimeric antigen receptor (CAR) design," Cancer Discov (2013) 3(4):388-398.

Scarpa et al., "Characterization of recombinant helper retroviruses from Moloney-based vectors in ecotropic and amphotropic packaging cell lines," Virology (1991) 180(2):849-852.

Screen captures from New York Academy of Sciences video clip of presentation entitled "Augmenting Car T Cell Potency and Safety with Synthetic Control Systems", presented at Sohn Conference; Pediatric Cancer in a Post-Genomic World, on Jul. 8, 2016, by Jensen, M.C. 51 pages. Uploaded on Jul. 8, 2016. Retrieved from the internet: <https://www.nyas.org/ebriefings/sohn-conference-pediatric-cancer-in-a-post-genomic-world/?tab=media>.

Screen captures from YouTube video clip of presentation entitled "CIPO2015: Enhancing the IQ of CART Cells Using the Synthetic Biology Tool Box", presented at 4th International Conference on Immunotherapy in Pediatric Oncology on Sep. 26, 2015, by Jensen, M.C. 40 pages. Uploaded on Oct. 16, 2015. Retrieved from internet <https://www.youtube.com/watch?v=TDxZS9hG4yQ>.

Sentman, "Challenges of creating effective chimeric antigen receptors for cancer therapy," Immunotherapy (2013) 5(8):783-785.

Shahrara et al., "Inhibition of Monocyte Chemoattractant Protein-1 Ameliorates Rat Adjuvant-Induced Arthritis," J Imunol (2008) 180:3447-3456.

Sharma et al., "Efficient Sleeping Beauty DNA Transposition From DNA Minicircles," Molec Ther Nucl Acids (2013) 2:e74.

Sohn conference: pediatric cancer in a post-genomic world, The New York Academy of Sciences, Mar. 30-Apr. 1, 2016, Agenda, 8 pp.

Strell et al., 2009, Divergent effects of norepinephrine, dopamine and substance P on the activation, differentiation and effector functions of human cytotoxic T lymphocytes, BMC Immunology, 10:62, 15 pp.

Szoka et al., "Comparative properties and methods of preparation of lipid vesicles (liposomes)," Annu Rev Biophys Bioeng (1980) 9:467-508.

Tanaka et al., "Immunotherapeutic implications of IL-6 blockade for cytokine storm," Immunotherapy. Jul. 2016;8(8):959-70.

Tasian et al., 2015, CD19-redirectec chimeric antigen receptor-modified T cells: a promising immunotherapy for children and adults with B-cell acute lymphoblastic leukemia (ALL), Ther Adv Hematol, 6(5):228-241.

Teachey et al., "Cytokine release syndrome after blinatumomab treatment related to abnormal macrophage activation and ameliorated with cytokine-directed therapy," Blood. Jun. 27, 2013;121(26):5154-7.

Teachey et al., Jun. 2016, Identification of predictive biomarkers for cytokine release syndrome after chimeric antigen receptor T-cell therapy for acute lymphoblastic leukemia, Cancer Discovery, pp. 664-679 and supplemental material.

Terakura et al., "Generation of CD19-chimeric antigen receptor modified CD8+ T cells derived from virus-specific central memory T cells," Blood (2012) 119(1):72-82.

Themeli et al., "Generation of tumor-targeted human T lymphocytes from induced pluripotent stem cells for cancer therapy," Nat Biotechnol (2013) 31(10):928-933.

Tsukahara et al., "CD19 target-engineered T-cells accumulate at tumor lesions in human B-cell lymphoma xenograft mouse models," Biochem Biophys Res Commun (2013) 438(1):84-89.

Tunkel, 2016, Fever, MSD Manual Professional Edition, https://web.archive.org/web/20160224024056/http://www/msdmanuals.com/professional/infectious-diseases/biology-of-infectious-disease/fever, 5 pp.

Turtle et al., "Engineered T cells for anti-cancer therapy," Engineered T cells for anti-cancer therapy, Curr Opin Immunol (2012) 24(5):633-639.

U.S. Department of Health and Human Services, National Institutes of Health, Jun. 10, 2015, Recombinant DNA Advisory Committee, Minutes of Meeting, 51 pp.

Vajdos et al., Jul. 5, 2002, Comprehensive functional maps of the antigen binding site of an anti-ERbB2 antibody obtained with shotgun scanning mutagenesis, J. Mol. Biol. 320(2):415-428.

Van Tedeloo et al., "High-level transgene expression in primary human T lymphocytes and adult bone marrow CD34+ cells via electroporation-mediated gene delivery," Gene Therapy (2000) 7(16):1431-1437.

Varela-Rohena et al., "Control of HIV-1 immune escape by CD8 T cells expressing enhanced T-cell receptor," Nat Med (2008) 14:1390-1395.

Verhoeyen et al., "Lentiviral vector gene transfer into human T cells," Methods Mol Biol (2009) 506:97-114.

Wadhwa et al., "Receptor mediated glycotargeting," J Drug Target (1995) 3(2):111-127.

Wang et al., "Phenotypic and Functional Attributes of Lentivirus Modified CD19-specific Human CD8+ Central Memory T Cells Manufactured at Clinical Scale," J Immunother (2012) 35(9):689-701.

Warzocha et al. Antisense Strategy: Biological Utility and Prospects in the Treatment of Hematological Malignancies. Leukemia and Lymphoma, 1997; 24(3-4): 267-281 (Year: 1997).

(56) References Cited

OTHER PUBLICATIONS

Wei et al., 2020, The model of cytokine release syndrome in CAR T-cell treatment for B-cell non-Hodgkin lymphoma, Signal Transduction and Targeted Therapy, 5:134.

Wigler et al., "Transfer of Purified Herpes Virus Thymidine Kinase Gene to Cultured Mouse Cells," Cell 2:223, 1977.

Wu et al., "Adoptive T-cell therapy using autologous tumor-infiltrating lymphocytes for metastatic melanoma: current status and future outlook," Cancer J (2012) 18(2):160-175.

Xu et al., "Cytokine release syndrome in cancer immunotherapy with chimeric antigen receptor engineered T cells.," Cancer Lett (2014) 343(2):172-178.

Statement of Opposition in European patent No. EP3433276B1, for and on behalf of Boult Wade Tennant LLP, dated Sep. 22, 2022, 62 pp.

Opposition against European patent No. EP3433276B1, by Patent Boutique LLP, dated Sep. 22, 2022, 46 pp.

Opposition to European patent No. EP3433276B1 by Gill Jennings & Every LLP, dated Sep. 22, 2022, 44 pp.

Notice of Opposition to European patent No. EP3433276B1 by Gedion Richter Pharma GmbH, dated Sep. 22, 2022, 47 pp.

Sauter et al. Interim Safety Analysis: a Phase I Trial of High Dose Therapy and Autologous Stem Cell Transplantation Followed By Infusion of Chimeric Antigen Receptor Modified T-Cells (19-28z CAR-T) Directed Against CD19+ B-Cells for Relapsed and. (Blood (2014) 124 (21): 677). (Year: 2014).

Le et al., 2018, FDC approval summary: tocilizumab for treatment of chimeric antigen receptor T cell-included sever or life-threatening cytokine release syndrome, The Oncologist, 23:943-947.

Mackowiak et al., Mar. 31, 2021, Defining Fever, Open Forum Infect Dis., 8(6):ofab161.

Newick et al., 2016, Chimeric antigen receptor T-cell therapy for solid tumors. Molecular Therapy-Oncolytics (2016) 3:16006, 7 pp.

Office of the Director, National Institutes of Health, NIH Recombinant DNA Advisory Committee (RAC) Meeting Special Workshop, Jun. 10, 2015, Cytokine release syndrome after T cell immunotherapy meeting, weblink https://videocast.nih.gov/watch=16420, 1pp.

Titov et al., 2018, The biological basis and clinical symptoms of CAR-T therapy-associated toxicities. Cell Death and Disease, 9:897, 15 pp.

Gardner R.A. et al. Preemptive Mitigation of CD19 CAR T-cell cytokine release syndrome without attenuation of antileukemic efficacy, Blood 134:2149-2158 (2019).

Le, R.Q., et al., FDA Approval Summary: Tocilizumab for Treatment of Chimeric Antigen Receptor T Cell-Induced Sever or Life-Threatening Cytokine Release Syndrome, The Oncologist 23:943-947 (2018).

Porter D.L., et al. Chimeric antigen receptor T cells persist and induce sustained remissions in relapsed refractory chromic lymphocytic leukemia, Sci Transl Med 2015;7:303ra139 (2015).

\* cited by examiner

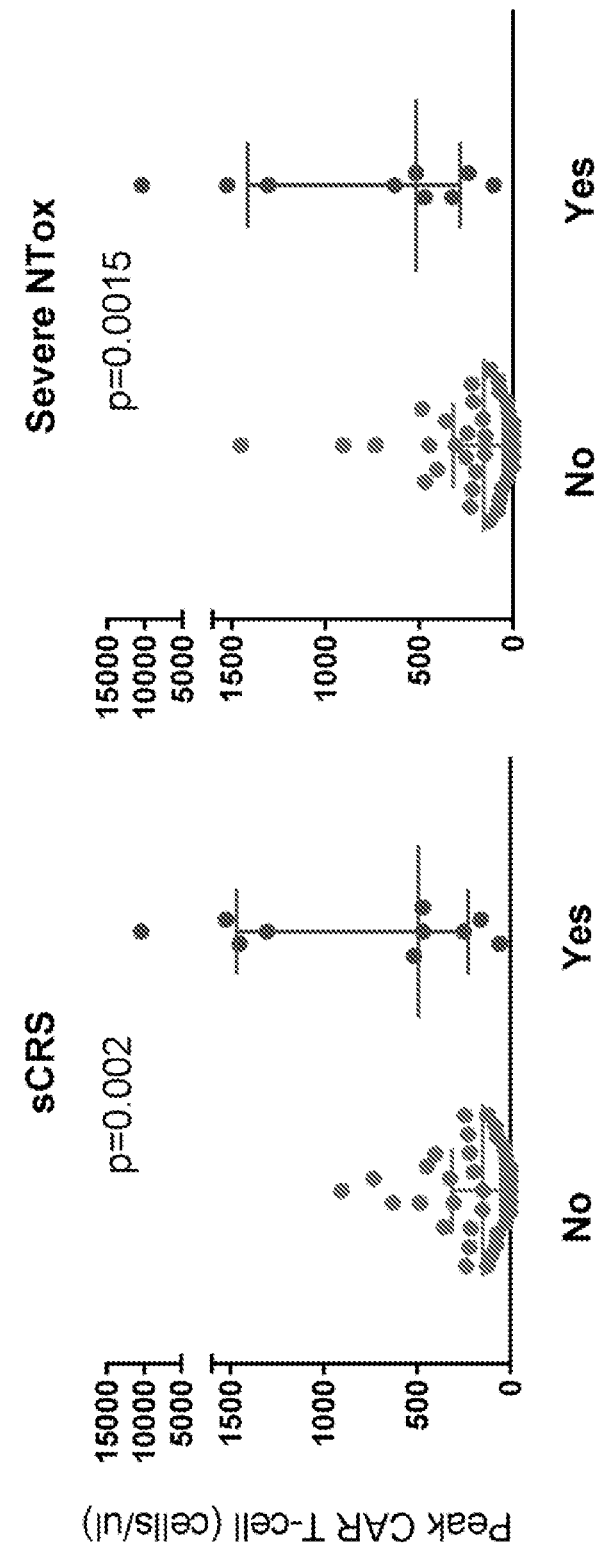

EARLY INTERVENTION METHODS TO PREVENT OR AMELIORATE TOXICITY

CROSS-REFERENCE TO RELATED APPLICATIONS

This application is a continuation of U.S. application Ser. No. 18/061,196 filed Dec. 2, 2022 which is a continuation of U.S. application Ser. No. 16/087,488 filed Sep. 21, 2018 now U.S. patent Ser. No. 11/518,814 issued Dec. 6, 2022 which is the U.S. National Phase of PCT App. No. PCT/US2017/023676 filed Mar. 22, 2017 published as WO 2017/165571 on Sep. 28, 2017 which claims priority to U.S. Prov. App. No. 62/311,906, filed Mar. 22, 2016, entitled "Early Intervention Methods to Prevent or Ameliorate Toxicity", U.S. Prov. App. No. 62/417,287, filed Nov. 3, 2016, entitled "Early Intervention Methods to Prevent or Ameliorate Toxicity", and U.S. Prov. App. No. 62/429,722, filed Dec. 2, 2016, entitled "Early Intervention Methods to Prevent or Ameliorate Toxicity", the contents of each is incorporated by reference in its entirety.

INCORPORATION BY REFERENCE OF SEQUENCE LISTING

The present application is being filed along with a Sequence Listing in electronic format. The Sequence Listing is provided as a file entitled SCRI138C3SEQLIST, created Jun. 6, 2023, which is about 22,803 bytes in size. The information in the electronic format of the Sequence Listing is incorporated by reference in its entirety.

FIELD

The present disclosure relates to methods for preventing or ameliorating toxicity caused by or due to a therapy, such as an immunotherapy or a cell therapy, by pre-emptive or early administration of a toxicity-targeting agent(s). In some embodiments, the therapy is a cell therapy in which the cells generally express recombinant receptors such as chimeric receptors, e.g., chimeric antigen receptors (CARs) or other transgenic receptors such as T cell receptors (TCRs). Features of the methods, including the timing of the administration of the agents or treatments for toxicity, provide various advantages, such as lower toxicity while maintaining persistence and efficacy of the administered cells.

BACKGROUND

Various immunotherapy and/or cell therapy methods are available for treating diseases and conditions. Improved methods are needed, for example, to reduce the risk of toxicity of such methods. For example, improved methods are needed to reduce the risk of toxicity to cell therapies, while maintaining exposure of the subject to the administered cells, for example, due to expansion and/or persistence of the administered cells. Provided are methods and uses that meet such needs.

SUMMARY

Provided in some aspects are methods of treatment including administering to a subject an agent or other treatment capable of treating, preventing, delaying, or attenuating the development of a toxicity. In some cases, at the time of said administration, the subject has been previously administered a therapy, such as a therapy including an immunotherapy and/or a cell therapy. In some embodiments, the administration of the agent or other treatment is at a time that is less than or no more than ten, seven, six, five, four or three days after initiation of the administration of the therapy. In some embodiments, the administration of the agent or other treatment is at a time at which the subject does not exhibit a sign or symptom of severe cytokine release syndrome (CRS) and/or does not exhibit grade 2 or higher CRS. In some embodiments, the administration of the agent or other treatment is at a time at which the subject does not exhibit a sign or symptom of severe neurotoxicity and/or does not exhibit grade 2 or higher neurotoxicity. In some aspects, between the time of the initiation of the administration of the therapy and the time of the administration of the agent or other treatment the subject has not exhibited severe CRS and/or has not exhibited grade 2 or higher CRS. In some instances, between the time of the initiation of the administration of the cell therapy and the time of the administration of the agent or other treatment, the subject has not exhibited severe neurotoxicity and/or does not exhibit grade 2 or higher neurotoxicity.

Provided in some embodiments are methods of treatment including administering to a subject administered with a therapy, such as an immunotherapy and/or a cell therapy, an agent or other treatment capable of treating, preventing, delaying, or attenuating the development of a toxicity. In some cases, the administration of the agent or other treatment is at a time that is less than or no more than ten, seven, six, five, four or three days after initiation of the administration of the therapy. In some embodiments, the administration of the agent or other treatment is at a time at which the subject does not exhibit a sign or symptom of severe cytokine release syndrome (CRS) and/or does not exhibit grade 2 or higher CRS. In some aspects, between the time of the initiation of the administration of the cell therapy and the time of the administration of the agent or other treatment, the subject has not exhibited severe CRS and/or does not exhibit grade 2 or higher CRS. In some embodiments, the administration of the agent or other treatment is at a time at which the subject does not exhibit a sign or symptom of severe neurotoxicity and/or does not exhibit grade 2 or higher neurotoxicity. In some aspects, between the time of the initiation of the administration of the cell therapy and the time of the administration of the agent or other treatment, the subject has not exhibited severe neurotoxicity and/or does not exhibit grade 2 or higher neurotoxicity.

Provided in some aspects are methods of treatment including administering to a subject having a disease or condition an immunotherapy or a cell therapy. In some cases the method involves administering to the subject an agent or other treatment capable of treating, preventing, delaying, or attenuating the development of a toxicity. In some cases, the administration of the agent or other treatment is at a time that is less than or no more than ten, seven, six, five, four or three days after initiation of the administration of the therapy. In some embodiments, the administration of the agent or other treatment is at a time at which the subject does not exhibit a sign or symptom of severe cytokine release syndrome (CRS) and/or does not exhibit grade 2 or higher CRS. In some embodiments, between the time of the initiation of the administration of the therapy and the time of the administration of the agent or other treatment, the subject has not exhibited severe CRS and/or does not exhibit grade 2 or higher CRS. In some aspects, the administration of the agent or other treatment is at a time at which the subject does not exhibit a sign or symptom of severe neurotoxicity and/or does not exhibit grade 2 or higher neurotoxicity. In some instances, between the time of the initiation of the administration of the therapy and the time of the administration of the agent or other treatment, the subject has not exhibited severe neurotoxicity and/or does not exhibit grade 2 or higher neurotoxicity. In some embodiments, the therapy includes a dose of cells expressing a recombinant receptor.

In some of any such embodiments, the agent or other treatment is administered at a time at which the subject exhibits grade 1 CRS or is administered within 24 hours after the subject exhibits a first sign or symptom of grade 1 CRS. In some cases, the agent or other treatment is administered at a time at which the subject exhibits a sign or symptom of CRS and/or exhibits grade 1 CRS. In some cases, the agent or other treatment is administered within 24 hours after the subject exhibits a first sign or symptom of grade 1 CRS following the initiation of administration of the therapy.

In some embodiments, a sign or symptom of grade 1 CRS is a fever. In some cases, the agent or other treatment is administered within 24 hours after the first sign of a fever following initiation of administration of the therapy.

Provided in some aspects are methods of treatment including administering to a subject previously administered with a therapy, such as an immunotherapy and/or a cell therapy, an agent or other treatment capable of treating, preventing, delaying, or attenuating the development of a toxicity. In some cases, the agent or other treatment is administered within 24 hours of the first sign of a fever following initiation of administration of the therapy.

In some embodiments, prior to administering the agent or other treatment, the method includes administering to the subject the therapy for treating a disease or condition.

Provided in some embodiments are methods of treatment including administering to a subject having a disease or condition an immunotherapy and/or a cell therapy. In some instances, the method includes administering to the subject an agent or other treatment capable of treating, preventing, delaying, or attenuating the development of a toxicity to the administered immunotherapy and/or cell therapy at a time within 24 hours after the first sign of a fever following initiation of administration of the therapy. In some aspects, the agent or other treatment is administered within about 16 hours, within about 12 hours, within about 8 hours, within about 2 hours or within about 1 hour after the first sign of a fever following initiation of administration of the therapy.

In some embodiments, the fever is a sustained fever. In some cases, the fever is not reduced or not reduced by more than 1° C. after treatment with an antipyretic. In some aspects, the fever is a fever that is not reduced or not reduced by more than 1° C. after treatment with an antipyretic. In some instances, the fever has not been reduced by more than 1° C., following treatment of the subject with an antipyretic.

In some embodiments, the fever includes a temperature of at least or at least about 38.0° C. In some aspects, the fever includes a temperature that is between or between about 38.0° C. and 42.0° C., 38.0° C. and 39.0° C., 39.0° C. and 40.0° C. or 40.0° C. and 42.0° C., each inclusive. In some embodiments, the fever includes a temperature that is greater than or greater than about or is or is about 38.5° C., 39.0° C., 39.5° C., 40.0° C., 41.0° C., 42.0° C.

In some embodiments, the agent or other treatment is administered less than five days after initiation of administration of the therapy, less than four days after initiation of administration of the therapy or less than three days after initiation of administration of the therapy.

In some embodiments, the therapy is or comprises a cell therapy. In some cases, the cell therapy is or comprises an adoptive cell therapy. In some aspects, the therapy is or comprises a tumor infiltrating lymphocytic (TIL) therapy, a transgenic TCR therapy or a recombinant receptor-expressing cell therapy, which optionally is a T cell therapy. In some embodiments, the therapy is a chimeric antigen receptor (CAR)-expressing T cell therapy.

In some cases, the agent or other treatment is or comprises a steroid, or an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta.

In some aspects, the antagonist or inhibitor is or comprises an agent selected from among an antibody or antigen-binding fragment, a small molecule, a protein or peptide and a nucleic acid. In some cases, the agent or other treatment is or comprises an agent selected from among tocilizumab, situximab, sarilumab, olokizumab (CDP6038), elsilimomab, ALD518/BMS-945429, sirukumab (CNTO 136), CPSI-2634, ARGX-109, FE301 and FM101.

In some embodiments, the agent or other treatment is or comprises tocilizumab. In some such embodiments, the tocilizumab is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the tocilizumab is administered in a dosage amount of at least or at least about or about 2 mg/kg, 4 mg/kg, 6 mg/kg or 8 mg/kg.

In some aspects, the method further includes administering a steroid to the subject. In some such aspects, the steroid is administered at a time that is within 7 days, 8 days or 9 days after administration of the therapy. In some cases, the steroid is administered at a time that is within 24 hours after the first sign of hypotension following administration of the therapy. In some instances, the steroid is administered at a time in which the subject exhibits grade 2 cytokine release syndrome (CRS) or within 24 hours after the subject exhibits a first sign of grade 2 CRS following administration of the therapy. In some embodiments, the steroid is administered at a time in which the subject exhibits grade 2 neurotoxicity or within 24 hours after the subject exhibits a first sign or symptom of grade 2 neurotoxicity following administration of the therapy.

Provided in some embodiments are methods of treatment including administering a steroid to a subject administered with a therapy, such as an immunotherapy and/or a cell therapy. In some embodiments, the administration of the steroid is initiated at a time that is within 7 days, 8 days or 9 days after initiation of administration of the therapy. In some embodiments, the administration of the steroid is initiated at a time that is within 24 hours after the first sign of hypotension following initiation of administration of the therapy. In some embodiments, the administration of the steroid is initiated at a time in which the subject exhibits grade 2 cytokine release syndrome (CRS) or within 24 hours after the subject exhibits a first sign of grade 2 CRS following initiation of administration of the therapy. In some embodiments, the administration of the steroid is initiated at a time in which the subject exhibits grade 2 neurotoxicity or within 24 hours after the subject exhibits a first sign or symptom of grade 2 neurotoxicity following initiation of administration of the therapy.

In some cases, prior to administering the steroid the method includes administering to the subject the therapy for treating a disease or condition.

Provided in some aspects are methods of treatment including administering to a subject having a disease or condition a therapy, such as an immunotherapy and/or a cell therapy. In some cases, the method further involves administering to the subject a steroid. In some aspects, the administration of the steroid is initiated at a time that is within 7 days, 8 days or 9 days after initiation of administration of the therapy. In some aspects, the administration of the steroid is initiated at a time that is within 24 hours after the first sign of hypotension following initiation of administration of the therapy. In some aspects, the administration of the steroid is initiated at a time in which the subject exhibits grade 2 or higher cytokine release syndrome (CRS) or within 24 hours after the subject exhibits a first sign of grade 2 or higher CRS following initiation of administration of the therapy. In some aspects, the administration of the steroid is initiated at a time in which the subject exhibits grade 2 or higher neurotoxicity or within 24 hours after the subject exhibits a first sign or symptom of grade 2 or higher neurotoxicity following initiation of administration of the therapy.

In some embodiments, at the time of administration of the steroid, the subject does not exhibit severe CRS, does not exhibit grade 3 or higher CRS, or does not exhibit severe neurotoxicity or does not exhibit grade 3 or higher neurotoxicity.

In some aspects, the steroid is administered within 24 hours after or contemporaneously with the first sign of hypotension following initiation of administration of the therapy. In some cases, the steroid is administered simultaneously with initiation of a pressor therapy. In some instances, hypotension includes systolic blood pressure less than or about less than 90 mm Hg, 80 mm Hg, or 70 mm Hg. In some instances, hypotension includes diastolic blood pressure less than 60 mm Hg, 50 mm Hg or 40 mm Hg.

In some embodiments, the agent is or comprises a steroid that is or comprises a corticosteroid. In some aspects, the agent is a steroid that is or comprises a glucocorticoid. In some cases, the corticosteroid is or comprises dexamethasone or prednisone. In some cases, the steroid is administered intravenously or orally.

In some instances, the steroid is administered in an equivalent dosage amount of from or from about 1.0 mg to 20 mg dexamethasone per day, 1.0 mg to 10 mg dexamethasone per day, or 2.0 mg to 6.0 mg dexamethasone per day, each inclusive.

In some embodiments, prior to administering the steroid, the method includes administering an agent or other treatment capable of treating, preventing, delaying, or attenuating the development of a toxicity. In some aspects, the agent or other treatment is administered at a time that is less than or no more than ten, seven, six, five, four or three days after initiation of the administration of the therapy. In some aspects, the agent or other treatment is administered at a time at which the subject does not exhibit a sign or symptom of severe cytokine release syndrome (CRS) and/or does not exhibit grade 2 or higher CRS. In some aspects, between the time of the initiation of the administration of the therapy and the time of the administration of the agent or other treatment, the subject has not exhibited severe CRS and/or does not exhibit grade 2 or higher CRS. In some aspects, the agent or other treatment is administered at a time at which the subject does not exhibit a sign or symptom of severe neurotoxicity and/or does not exhibit grade 2 or higher neurotoxicity. In some embodiments, between the time of the initiation of the administration of the therapy and the time of the administration of the agent or other treatment, the subject has not exhibited severe neurotoxicity and/or does not exhibit grade 2 or higher neurotoxicity.

In some embodiments, the therapy includes a dose of cells expressing a recombinant receptor.

In some aspects, the agent or other treatment is administered at a time at which the subject exhibits grade 1 CRS or is administered within 24 hours after the subject exhibits a first sign or symptom of grade 1 CRS. In some embodiments, a sign or symptom of grade 1 CRS is a fever. In some embodiments, the first sign or symptom of CRS is a fever. In some instances, the agent or other treatment is administered within 24 hours after the first sign of a fever following the initiation of administration of the therapy.

In some aspects, prior to administering the steroid, the method includes administering an agent or other treatment capable of treating, preventing, delaying, or attenuating the development of a toxicity. In some cases, the agent or other treatment is administered within 24 hours after the first sign of a fever following the initiation of administration of the therapy. In some aspects, the agent or other treatment is administered within about 16 hours, within about 12 hours, within about 8 hours, within about 2 hours or within about 1 hour after the first sign of a fever following the initiation of administration of the therapy.

In some embodiments, the fever is a sustained fever. In some instances the fever is not reduced or not reduced by more than 1° C. after treatment with an antipyretic. In some embodiments, the fever is a fever that is not reduced or not reduced by more than 1° C. after treatment with an antipyretic. In some cases, the fever has not been reduced by more than 1° C., following treatment of the subject with an antipyretic.

In some cases, the fever includes a temperature of at least or at least about 38.0° C. In some embodiments, the fever includes a temperature that is between or between about 38.0° C. and 42.0° C., 38.0° C. and 39.0° C., 39.0° C. and 40.0° C. or 40.0° C. and 42.0° C., each inclusive. In some aspects, the fever includes a temperature that is greater than or greater than about or is or is about 38.5° C., 39.0° C., 39.5° C., 40.0° C., 41.0° C., 42.0° C.

In some embodiments, the agent or other treatment is administered less than five days after initiation of administration of the therapy, less than four days after initiation of administration of the therapy or less than three days after initiation of administration of the therapy.

In some cases of any of the above embodiments, the therapy is or comprises a cell therapy. In some embodiments, the cell therapy is or comprises an adoptive cell therapy. In some instances, the therapy is or comprises a tumor infiltrating lymphocytic (TIL) therapy, a transgenic TCR therapy or a recombinant-receptor expressing cell therapy, which optionally is a T cell therapy. In some embodiments, the therapy is or includes a chimeric antigen receptor (CAR)-expressing cell therapy.

In some embodiments, the agent or other treatment is or comprises an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta. In some embodiments, the antagonist or inhibitor is or comprises an agent selected from among an antibody or antigen-binding fragment, a small molecule, a protein or peptide and a nucleic acid.

In some cases, the agent or other treatment is or comprises an agent selected from among tocilizumab, situximab, sarilumab, olokizumab (CDP6038), elsilimomab, ALD518/BMS-945429, sirukumab (CNTO 136), CPSI-2634, ARGX-109, FE301 and FM101.

In some aspects, the agent or other treatment is or comprises tocilizumab. In some embodiments, the tocilizumab is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the tocilizumab is administered in a dosage amount of at least or at least about or about 2 mg/kg, 4 mg/kg, 6 mg/kg or 8 mg/kg.

In some of any of the above embodiments, the therapy is or comprises a cell therapy and the number of cells administered is between about $0.25 \times 10^6$ cells/kg body weight of the subject and $5 \times 10^6$ cells/kg, $0.5 \times 10^6$ cells/kg body weight of the subject and $3 \times 10^6$ cells/kg, between about $0.75 \times 10^6$ cells/kg and $2.5 \times 10^6$ cells/kg or between about $1 \times 10^6$ cells/kg and $2 \times 10^6$ cells/kg, each inclusive.

In some embodiments, the therapy is or comprises a cell therapy and the cells are administered in a single pharmaceutical composition containing the cells. In some cases, the therapy is or comprises a cell therapy and the dose of cells is a split dose, wherein the cells of the dose are administered in a plurality of compositions, collectively containing the cells of the dose, over a period of no more than three days.

In some embodiments, the disease or condition is or comprises a tumor or a cancer. In some cases, the disease or condition is or comprises a leukemia or lymphoma. In some embodiments, the disease or condition is a B cell malignancy or is a hematological disease or condition. In some aspects, the disease or condition is or comprises a non-Hodgkin lymphoma (NHL) or acute lymphoblastic leukemia (ALL).

In some embodiments, the therapy is a cell therapy including a dose of cells expressing a recombinant receptor. In some aspects, the recombinant receptor binds to, recognizes or targets an antigen associated with the disease or condition. In some cases, the recombinant receptor is a T cell receptor or a functional non-T cell receptor. In some instances, the recombinant receptor is a chimeric antigen receptor (CAR).

In some embodiments, the CAR contains an extracellular antigen-recognition domain that specifically binds to the antigen and an intracellular signaling domain containing an ITAM. In some cases, the antigen is CD19. In some embodiments, the intracellular signaling domain contains an intracellular domain of a CD3-zeta (CD3ζ) chain. In some embodiments, the CAR further contains a costimulatory signaling region. In some aspects, the costimulatory signaling domain contains a signaling domain of CD28 or 4-1BB.

In some embodiments, the therapy is or comprises a therapy containing a dose of cells containing T cells. In some cases, the T cells are CD4+ or CD8+. In some embodiments, the T cells are autologous to the subject.

In some embodiments, the method further includes administering a chemotherapeutic agent prior to administering the therapy. In some instances, the subject has been previously treated with a chemotherapeutic agent prior to the initiation of administration of the therapy. In some aspects, the chemotherapeutic agent includes an agent selected from the group consisting of cyclophosphamide, fludarabine, and/or a combination thereof. In some embodiments, the chemotherapeutic agent is administered between 2 and 5 days prior to the initiation of administration of the therapy. In some cases, the chemotherapeutic agent is administered at a dose of between at or about 1 g/m² of the subject and at or about 3 g/m² of the subject.

In some embodiments, toxicity is a neurotoxicity. In some embodiments, a CNS-related outcome in the subject at day up to or up to about day 7, 8, 9, 10, 11, 12, 13, 14, 15, 16, 17, 18, 19, 20, 21, 22, 23, 24, 25, 26, 27, 28, 29 or 30 following administration of the therapy is not detectable or is reduced as compared to a method including an alternative treatment regimen wherein the subject is administered the agent or other treatment after severe CRS or neurotoxicity has developed or after grade 2 or higher CRS or neurotoxicity has developed. In some embodiments, the toxic outcome is a symptom associated with grade 3 or higher neurotoxicity or is a symptom associated with grade 2 or higher CRS. In some embodiments, the toxic outcome is reduced by greater than 50%, 60%, 70%, 80%, 90% or more. In some cases, the toxic outcome is a symptom associated with grade 3 or higher neurotoxicity. In some embodiments, the toxic outcome is selected from among grade 3 or higher neurotoxicity include confusion, delirium, expressive aphasia, obtundation, myoclonus, lethargy, altered mental status, convulsions, seizure-like activity and seizures.

In some aspects, the therapy is a therapy and the cells exhibit increased or longer expansion and/or persistence in the subject than cells administered in a method including an alternative treatment regimen wherein the subject is administered the agent or other treatment after severe CRS or neurotoxicity has developed or after grade 2 or higher CRS or neurotoxicity has developed. In some instances, expansion and/or persistence is increased 2-fold, 3-fold, 4-fold, 5-fold, 6-fold, 7-fold, 8-fold, 9-fold or 10-fold.

In some embodiments, the toxic outcome is grade 3 or higher CRS comprising one or more symptom selected from among persistent fever greater than at or about 38 degrees Celsius, for at least three consecutive days; hypotension requiring high dose vasopressor or multiple vasopressors; hypoxia, which optionally comprises (e.g., plasma oxygen (PO2) levels of less than at or about 90% and respiratory failure requiring mechanical ventilation. In some embodiments, the therapy is a cell therapy comprising a dosage of cells and the cells exhibit increased or prolonged expansion and/or persistence in the subject as compared to administration of the cell therapy (in the subject or in a corresponding subject in an alternative cohort or treatment group) using alternative treatment regimen, wherein said alternative treatment regimen comprises administering the cell therapy and subsequently administering the agent or other treatment after severe CRS has developed or after grade 2 or higher CRS has developed, and optionally wherein the subject in said alternative treatment regimen is not administered said agent, and optionally is not administered any other treatment designed to treat CRS or neurotoxicity, following the administration of the cells and prior to said development of grade 2 or higher CRS or severe CRS. In some embodiments, the increase in or prolonging of expansion and/or persistence is by 2-fold, 3-fold, 4-fold, 5-fold, 6-fold, 7-fold, 8-fold, 9-fold or 10-fold.

In some embodiments, the therapy is a cell therapy comprising a dosage of cells and the cells exhibit increased or prolonged expansion and/or persistence in the subject as compared to a the administration of the cell therapy (in the subject or a corresponding subject in an alternative cohort or treatment group) using alternative treatment regimen. In some cases, said alternative treatment regimen comprises administering the cell therapy and subsequently administering the agent or other treatment after severe CRS or neurotoxicity has developed or after grade 2 or higher CRS or neurotoxicity has developed. In some cases, the subject in said alternative treatment regimen is not administered said agent. In some instances, the subject in said alternative treatment regimen is not administered any other treatment designed to treat CRS or neurotoxicity, following the administration of the cells and prior to said development of grade 2 or higher CRS or severe CRS or grade 2 or higher neurotoxicity or severe neurotoxicity.

In some embodiments, the increase in or prolonging of expansion and/or persistence is by 2-fold, 3-fold, 4-fold, 5-fold, 6-fold, 7-fold, 8-fold, 9-fold or 10-fold.

In some embodiments, the cells exhibit the same or similar expansion and/or persistence in the subject than cells administered in a method including an alternative treatment regimen wherein the subject is administered the cell therapy but in the absence of the agent or the other treatment. In some embodiments, the expansion and/or persistence is no more than 2-fold lower or reduced than in a method including an alternative treatment regimen wherein the subject is administered the cell therapy but in the absence of the agent or the other treatment.

In some embodiments, the therapy is a cell therapy, comprising engineered and/or CAR-expressing cells. In some cases, the concentration or number of the engineered and/or CAR-expressing cells in the blood of the subject at day 30, day 60, or day 90 following initiation of administration of the therapy is at least at or about 10 engineered or CAR-expressing cells per microliter, at least 50% of the total number of peripheral blood mononuclear cells (PBMCs), at least or at least about $1\times10^5$ engineered or CAR-expressing cells, and/or at least 5,000 copies of CAR-encoding or engineered receptor-encoding DNA per micrograms DNA. In some embodiments, at day 30, 60, or 90 following the initiation of the administration of the therapy, the CAR-expressing and/or engineered cells are detectable in the blood or serum of the subject. In some instances, at day 30, 60, or 90 following the initiation of the administration of the therapy, the blood of the subject contains at least 20% CAR-expressing cells, at least 10 CAR-expressing cells per microliter or at least $1\times10^4$ CAR-expressing cells. In some cases, at day 30, 60, or 90 following the initiation of the administration of the therapy, the blood of the subject contains at least 50%, 60%, 70%, 80%, or 90% of a biologically effective dose of the cells. In some embodiments, at day 30, 60, or 90 following the initiation of the administration of the therapy, the blood of the subject contains at least 20% engineered and/or CAR-expressing cells, at least 10 engineered and/or CAR-expressing cells per microliter and/or at least $1\times10^4$ engineered and/or CAR-expressing cells. In some cases, at day 30, 60, or 90 following the initiation of the administration of the therapy, the subject exhibits a reduction or sustained reduction in burden of the disease or condition. In some cases, the reduction or sustained reduction in burden of the disease or condition is at or about or at least at or about 50, 60, 70, or 80% peak reduction following the therapy administration or reduction associated with effective dose.

In some embodiments, at day 30, 60 or 90 following the initiation of the administration of the therapy, the subject does not, and/or has not, following the cell therapy treatment, exhibited severe neurotoxicity, severe CRS, grade 2 or higher CRS, grade 2 or higher neurotoxicity, and/or has not exhibited seizures or other CNS outcome; or at day 30, 60, or 90 following the initiation of the administration of the therapy, less than or about less than 25%, less than or about less than 20%, less than or about less than 15%, or less than or about less than 10% of the subjects so treated do not, and/or have not, following the cell therapy treatment, exhibited severe neurotoxicity, severe CRS, grade 2 or higher CRS, grade 2 or higher neurotoxicity, and/or have not exhibited seizures or other CNS outcome.

In some embodiments, the therapy is a cell therapy, comprising engineered and/or CAR-expressing cells; and the area under the curve (AUC) for blood concentration of engineered and/or CAR-expressing cells over time following the administration of the therapy is greater as compared to that achieved via a method comprising an alternative dosing regimen, such as where the subject is administered the therapy and is administered the agent or other treatment at a time at which the subject exhibits a severe or grade 2 or higher or grade 3 or higher CRS or neurotoxicity.

In some embodiments, also provided are agents or other treatment for use in the treatment, prevention, delay or attenuation of the development of a toxicity in a subject that has been previously administered a therapy, which therapy comprises an immunotherapy and/or a cell therapy. In some embodiments, (a) the agent or other treatment is administered to a subject: (i) at a time that is less than or no more than ten, seven, six, five, four or three days after initiation of the subject having been administered the therapy; and/or (ii) at a time at which the subject does not exhibit a sign or symptom of severe cytokine release syndrome (CRS) and/or does not exhibit grade 2 or higher CRS; and/or (iii) at a time at which the subject does not exhibit a sign or symptom of severe neurotoxicity and/or does not exhibit grade 2 or higher neurotoxicity; and/or (b) between the time of initiation of the subject having been administered the therapy and the time of the administration of the agent or other treatment, (i) the subject has not exhibited severe CRS and/or has not exhibited grade 2 or higher CRS and/or (ii) the subject has not exhibited severe neurotoxicity and/or does not exhibit grade 2 or higher neurotoxicity.

In some embodiments, the agent or other treatment is administered at a time at which the subject exhibits a sign or symptom of CRS and/or exhibits grade 1 CRS or is administered within 24 hours after the subject exhibits a first sign or symptom of grade 1 CRS following the administration of the therapy. In some embodiments, the sign or symptom of grade 1 CRS is a fever; and/or the agent or other treatment is administered within 24 hours after the first sign of a fever following administration of the therapy.

In some embodiments, also provided are agents or other treatment use in the treatment, prevention, delay or attenuation of the development of a toxicity in a subject that has been previously administered a therapy, which therapy comprises an immunotherapy and/or a cell therapy, wherein the agent or other treatment is administered within 24 hours of the first sign of a fever following administration of the therapy.

In some embodiments, also provided are agents or other treatment for use as a medicament in treating, preventing, delaying, or attenuating the development of a toxicity in a subject that has been previously administered a therapy, which therapy comprises an immunotherapy and/or a cell therapy. In some embodiments, (a) the agent or other treatment is administered to a subject: (i) at a time that is less than or no more than ten, seven, six, five, four or three days after initiation of the subject having been administered the therapy; and/or (ii) at a time at which the subject does not exhibit a sign or symptom of severe cytokine release syndrome (CRS) and/or does not exhibit grade 2 or higher CRS; and/or (iii) at a time at which the subject does not exhibit a sign or symptom of severe neurotoxicity and/or does not exhibit grade 2 or higher neurotoxicity; and/or (b) between the time of initiation of the subject having been administered the therapy and the time of the administration of the agent or other treatment, (i) the subject has not exhibited severe CRS and/or has not exhibited grade 2 or higher CRS and/or (ii) the subject has not exhibited severe neurotoxicity and/or does not exhibit grade 2 or higher neurotoxicity.

In some embodiments, the agent or other treatment is administered at a time at which the subject exhibits a sign or symptom of CRS and/or exhibits grade 1 CRS or is administered within 24 hours after the subject exhibits a first sign or symptom of grade 1 CRS following the administration of the therapy. In some embodiments, the sign or symptom of grade 1 CRS is a fever; and/or the agent or other treatment is administered within 24 hours after the first sign of a fever following administration of the therapy.

In some embodiments, also provided are agents or other treatment for use as a medicament in treating, preventing, delaying, or attenuating the development of a toxicity in a subject that has been previously administered a therapy, which therapy comprises an immunotherapy and/or a cell therapy, wherein the agent or other treatment is administered within 24 hours of the first sign of a fever following administration of the therapy.

In some embodiments, also provided are uses of agents or other treatment for the manufacture of a medicament for treating, preventing, delaying, or attenuating the development of a toxicity in a subject that has been previously administered a therapy, which therapy comprises an immunotherapy and/or a cell therapy. In some embodiments, (a) the agent or other treatment is administered to a subject: (i) at a time that is less than or no more than ten, seven, six, five, four or three days after initiation of the subject having been administered the therapy; and/or (ii) at a time at which the subject does not exhibit a sign or symptom of severe cytokine release syndrome (CRS) and/or does not exhibit grade 2 or higher CRS; and/or (iii) at a time at which the subject does not exhibit a sign or symptom of severe neurotoxicity and/or does not exhibit grade 2 or higher neurotoxicity; and/or (b) between the time of initiation of the subject having been administered the therapy and the time of the administration of the agent or other treatment, (i) the subject has not exhibited severe CRS and/or has not exhibited grade 2 or higher CRS and/or (ii) the subject has not exhibited severe neurotoxicity and/or does not exhibit grade 2 or higher neurotoxicity. In some embodiments, the agent or other treatment is administered at a time at which the subject exhibits a sign or symptom of CRS and/or exhibits grade 1 CRS or is administered within 24 hours after the subject exhibits a first sign or symptom of grade 1 CRS following the administration of the therapy. In some embodiments, the sign or symptom of grade 1 CRS is a fever; and/or the agent or other treatment is administered within 24 hours after the first sign of a fever following administration of the therapy.

In some embodiments, also provided are uses of agents or other treatment for the manufacture of a medicament for treating, preventing, delaying, or attenuating the development of a toxicity in a subject that has been previously administered a therapy, which therapy comprises an immunotherapy and/or a cell therapy, wherein the agent or other treatment is administered within 24 hours of the first sign of a fever following administration of the therapy.

In some of the embodiments of the agents, other treatment or uses thereof provided herein, the agent or other treatment is administered within about 16 hours, within about 12 hours, within about 8 hours, within about 2 hours or within about 1 hour after the first sign of a fever following administration of the therapy.

In some embodiments, the fever is a sustained fever. In some embodiments, the fever is a fever that is not reduced or not reduced by more than 1° C. after treatment with an antipyretic and/or wherein the fever has not been reduced by more than 1° C., following treatment of the subject with an antipyretic. In some embodiments, the fever comprises a temperature of at least or at least about 38.0° C. In some embodiments, the fever comprises a temperature that is between or between about 38.0° C. and 42.0° C., 38.0° C. and 39.0° C., 39.0° C. and 40.0° C. or 40.0° C. and 42.0° C., each inclusive; or the fever comprises a temperature that is greater than or greater than about or is or is about 38.5° C., 39.0° C., 39.5° C., 40.0° C., 41.0° C., 42.0° C.

In some embodiments, the agent or other treatment is or comprises a steroid, or an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1, CCR5, TNFalpha, TNFR1, IL-1, and IL-1Ralpha/IL-1beta. In some embodiments, the antagonist or inhibitor is or comprises an agent selected from among an antibody or antigen-binding fragment, a small molecule, a protein or peptide and a nucleic acid.

In some embodiments, the agent or other treatment is or comprises an agent selected from among tocilizumab, situximab, sarilumab, olokizumab (CDP6038), elsilimomab, ALD518/BMS-945429, sirukumab (CNTO 136), CPSI-2634, ARGX-109, FE301 and FM101. In some embodiments, the agent or other treatment is or comprises tocilizumab. In some embodiments, the tocilizumab is for administration in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the tocilizumab is administered in a dosage amount of at least or at least about or about 2 mg/kg, 4 mg/kg, 6 mg/kg or 8 mg/kg.

In some embodiments, the agent is or comprises a steroid that optionally is or comprises a corticosteroid, which optionally is a glucocorticoid. In some embodiments, the corticosteroid is or comprises dexamethasone or prednisone. In some embodiments, the steroid is for administration in an equivalent dosage amount of from or from about 1.0 mg to 20 mg dexamethasone per day, 1.0 mg to 10 mg dexamethasone per day, or 2.0 mg to 6.0 mg dexamethasone per day, each inclusive. In some embodiments, the steroid is formulated for intravenous or oral administration.

In some of the embodiments of the agents, other treatment or uses thereof provided herein, the therapy is or comprises a cell therapy. In some embodiments, the cell therapy is or comprises an adoptive cell therapy. In some embodiments, the therapy is or comprises a tumor infiltrating lymphocytic (TIL) therapy, a transgenic TCR therapy or a recombinant-receptor expressing cell therapy, which optionally is a T cell therapy, which optionally is a chimeric antigen receptor (CAR)-expressing cell therapy. In some embodiments, the therapy is a cell therapy comprising a dose of cells expressing a recombinant receptor, wherein: the recombinant receptor binds to, recognizes or targets an antigen associated with a disease or condition; and/or the recombinant receptor is a T cell receptor or a functional non-T cell receptor; and/or the recombinant receptor is a chimeric antigen receptor (CAR).

In some embodiments, the CAR comprises an extracellular antigen-recognition domain that specifically binds to the antigen and an intracellular signaling domain comprising an ITAM. In some embodiments, the antigen is CD19. In some embodiments, the intracellular signaling domain comprises an intracellular domain of a CD3-zeta (CD3ζ) chain. In some embodiments, the CAR further comprises a costimulatory signaling region. In some embodiments, the costimulatory signaling domain comprises a signaling domain of CD28 or 4-1BB.

In some embodiments, the therapy is a cell therapy comprising a dose of cells comprising T cells. In some embodiments, the T cells are CD4+ or CD8+. In some embodiments, the T cells are autologous to the subject. In some embodiments, the disease or condition is a tumor or a cancer. In some embodiments, the disease or condition is a leukemia or lymphoma. In some embodiments, the disease or condition is a non-Hodgkin lymphoma (NHL) or acute lymphoblastic leukemia (ALL).

In some embodiments, the subject has been previously treated with a chemotherapeutic agent prior to the administration of the therapy. In some embodiments, the chemotherapeutic agent comprises an agent selected from the group consisting of cyclophosphamide, fludarabine, and/or a combination thereof.

BRIEF DESCRIPTION OF THE DRAWINGS

FIG. 1A shows a toxicity profile of a subject exhibiting mild toxicity side effects following treatment with CAR-expressing T cells, in which no intervention of the toxicity was employed. FIG. 1B shows a toxicity profile of a subject exhibiting severe side effects in which intervention methods employing tocilizumab (toci) at a time at which CRS symptoms were severe, pressor therapy at a time at which hypotension developed and dexamethasone at a time subsequent to the pressor therapy. The timeframe at which CNS toxicity is present is depicted.

FIG. 4A and FIG. 4B show peak number of CAR T-cells per microliter of peripheral bloodin subjects with (yes) and without (no) severe CRS or severe neurotoxicity, respectively.

DETAILED DESCRIPTION

Figure 1A:
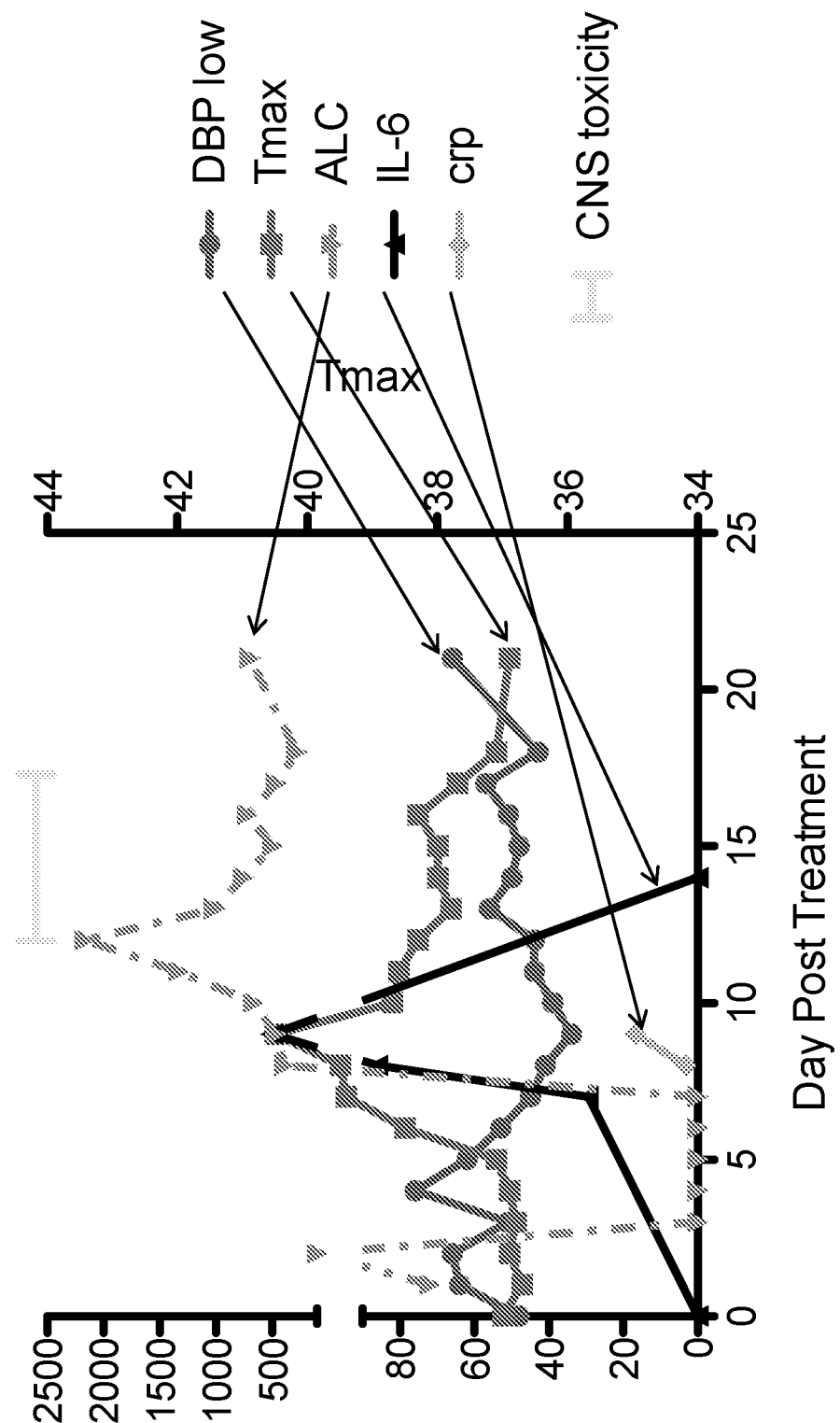
FIG. 1A and FIG. 1B show a toxicity profile of exemplary subjects treated with CAR-expressing T cells.

Provided herein are methods involving early or preemptive treatment to prevent or ameliorate potential toxicities that may be associated with certain therapies when administered to a subject.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Methods of Preemptive Intervention with Toxicity-Targeting Agents

Provided are methods involving administration of an immunotherapy, such as a cell therapy (e.g. CAR-T cell therapy) and administration of a toxicity-targeting agent for early intervention of, or risk of developing, a toxicity to the immunotherapy, such as a toxicity that is or includes cytokine release syndrome (CRS) or a neurotoxicity. In some embodiments, the methods involve administration of a toxicity-targeting agent(s) at a time when signs or symptoms of cytokine release syndrome (CRS) resulting from the immunotherapy, such as cell therapy, are relatively mild and/or are not severe. In some embodiments, the methods permit treatment of a subject with a therapy for treating a disease or disorder, such as an immunotherapy or a cell therapy, that otherwise may result in moderate to severe CRS or neurotoxicity side effects in the subjects. In the provided methods, the early intervention or preemptive treatment with a toxicity-targeting agent(s) prevents or ameliorates the risk of moderate to severe CRS or neurotoxicity while maintaining the efficacy of the therapy, such as, for the case of cell therapy, the persistence of the therapy.

In some embodiments, the subject has been or is receiving a therapy, such as an immunotherapy or a cell therapy, for example, for treating a disease or condition in a subject. For example, in some embodiments, the cell therapy is an adoptive cell therapy, including a therapy involving administration of cells expressing chimeric receptors specific for a disease or disorder of interest, such as chimeric antigen receptors (CARs) and/or other recombinant antigen receptors, as well as other adoptive immune cells and adoptive T cell therapies. In some embodiments, the adoptive cell therapy includes administration of a dose of cells expressing a recombinant receptor, such as a CAR or other recombinant antigen receptor. In some embodiments, chimeric receptors, such chimeric antigen receptor, contain one or more domains that combine a ligand-binding domain (e.g. antibody or antibody fragment) that provides specificity for a desired antigen (e.g., tumor antigen) with intracellular signaling domains. In some embodiments, the intracellular signaling domain is an activating intracellular domain portion, such as a T cell activating domain, providing a primary activation signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

Adoptive cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. In certain contexts, available approaches to adoptive cell therapy may not always be entirely satisfactory. In some contexts, optimal efficacy can depend on the ability of the administered cells to recognize and bind to a target, e.g., target antigen, to traffic, localize to and successfully enter appropriate sites within the subject, tumors, and environments thereof, to become activated, expand, to exert various effector functions, including cytotoxic killing and secretion of various factors such as cytokines, to persist, including long-term, to differentiate, transition or engage in reprogramming into certain phenotypic states (such as effector, long-lived memory, less-differentiated, and effector states), to provide effective and robust recall responses following clearance and re-exposure to target ligand or antigen, and avoid or reduce exhaustion, anergy, terminal differentiation, and/or differentiation into a suppressive state.

In some aspects, the provided embodiments are based on observations that the efficacy of adoptive cell therapy may be limited by the development of toxicity in the subject to whom such cells are administered, which toxicity in some cases can be severe. For example, in some cases, administering a dose of cells expressing a recombinant receptor, e.g. a CAR, can result in toxicity or risk thereof, such as CRS or neurotoxicity. In some cases, while a higher dose of such cells can increase the efficacy of the treatment, for example, by increasing exposure to the cells such as by promoting expansion and/or persistence, they may also result in an even greater risk of developing a toxicity or a more severe toxicity. Also, in some cases, subjects with a higher disease burden also may be at a greater risk for developing a toxicity or a more severe toxicity.

Figure 1B:
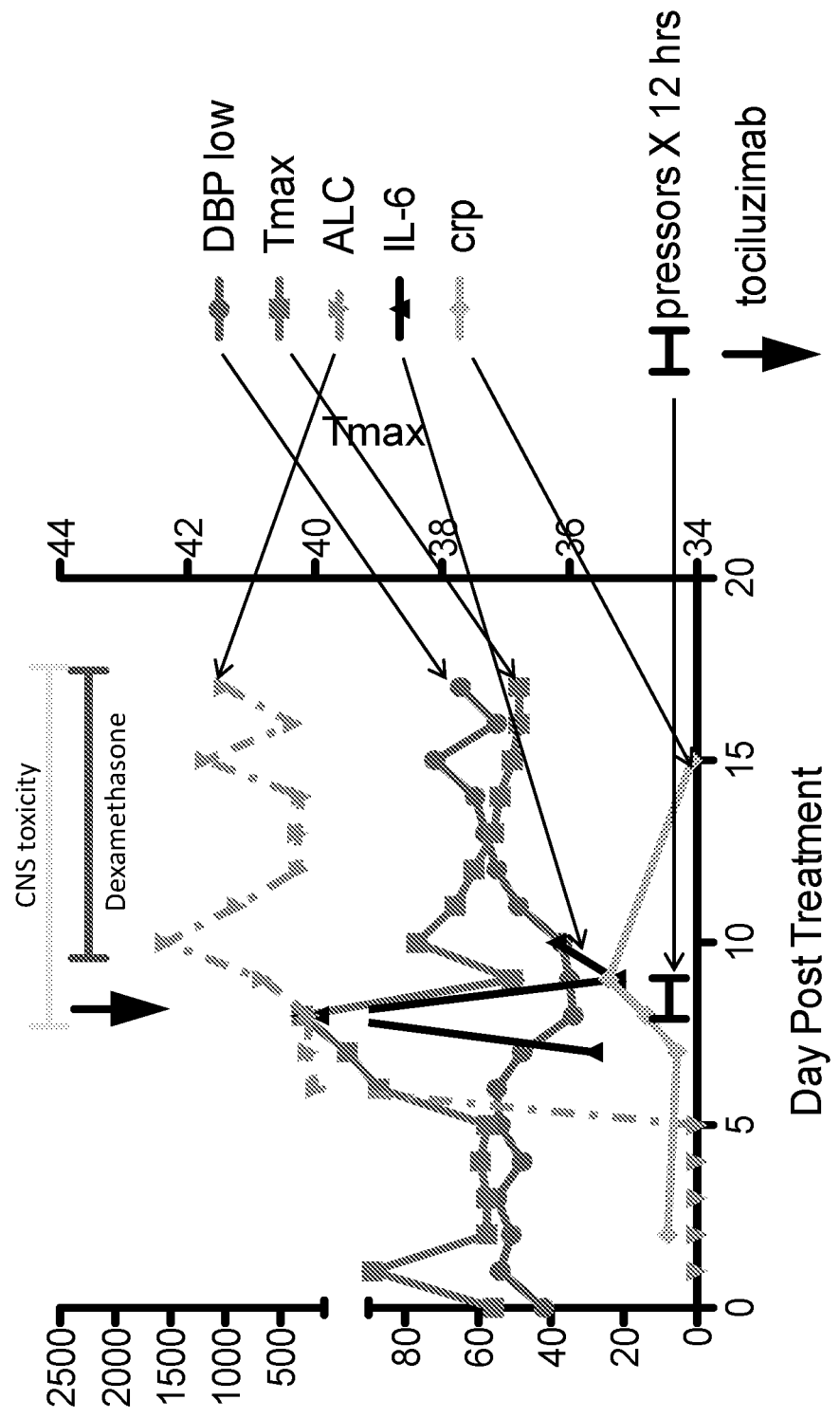
Figure 2A:
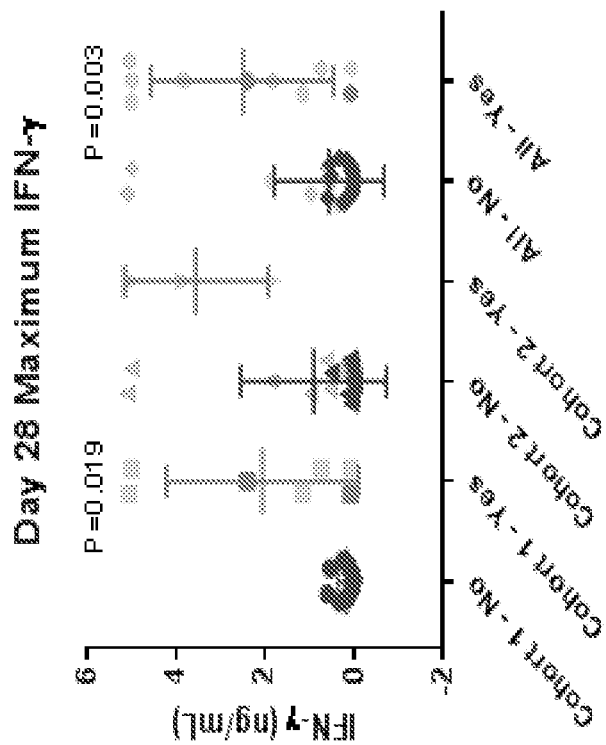
FIGS. 2A, 2B, 2C, and 2D show the correlation of peak cytokine levels for IL-6, IFN-γ, Granzyme B, and IL-2, respectively, in subjects with (yes) and without (no) severe CRS at day 28 after infusion of CAR+ T cells. P-values indicate statistically significant differences between subjects within the same cohort with and without severe CRS.
Figure 2B:
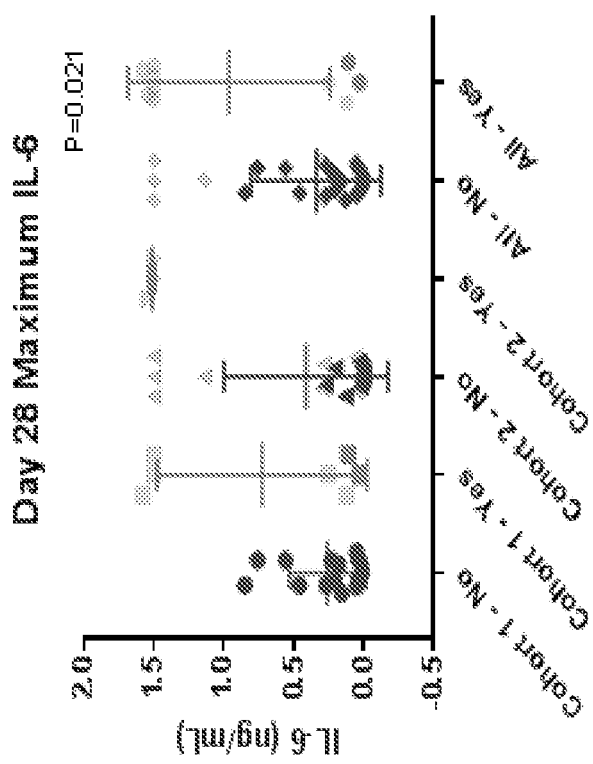
Figures 2C, 2D:
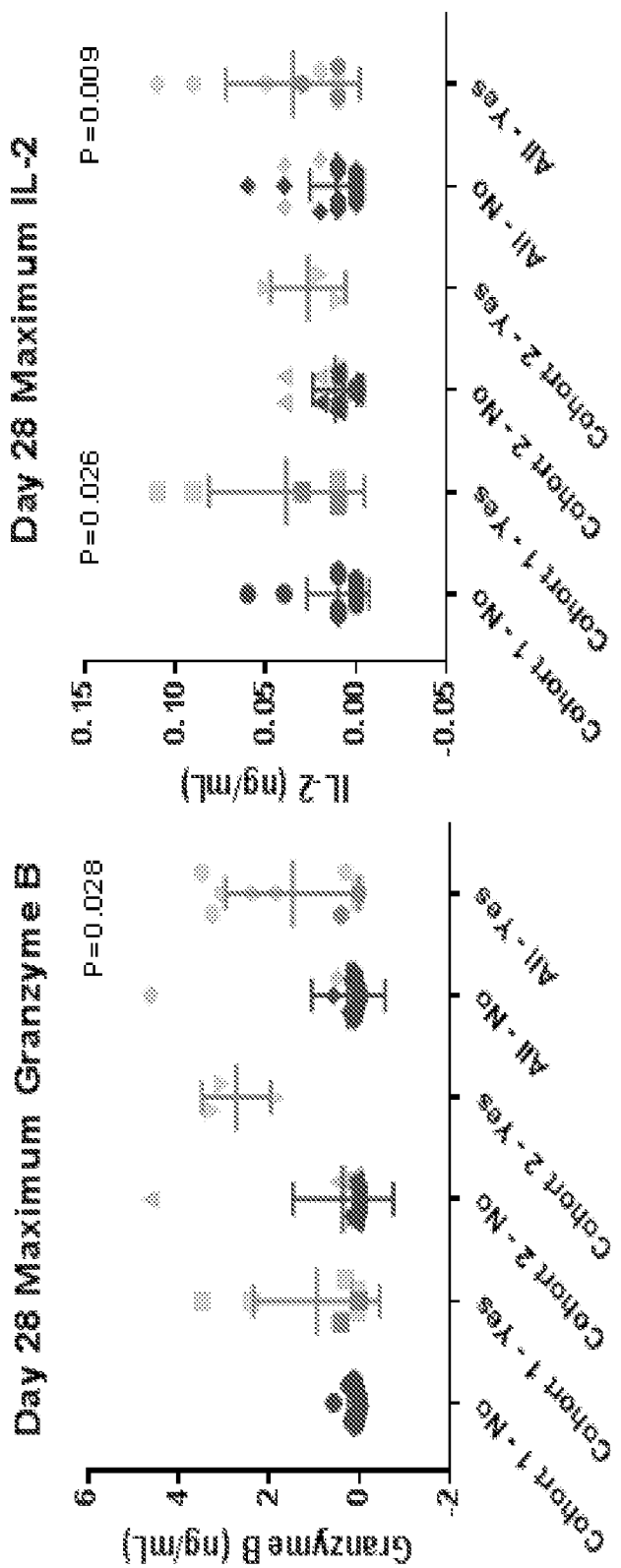

Certain available methods for treating or ameliorating toxicity may not always be entirely satisfactory. Many such approaches focus, for example, on targeting downstream effects of toxicity, such as by cytokine blockade, and/or delivering agents such as high-dose steroids which can also eliminate or impair the function of administered cells. Additionally, such approaches often involve administration of such interventions only upon detection of physical signs or symptoms of toxicity, which in general involve signs or symptoms of moderate or severe toxicity (e.g. moderate or severe CRS or moderate or severe neurotoxicity). For example, FIGS. 1A and 1B provide a comparison of toxicity profiles in which one subject (shown in FIG. 1B) is in need to an intervention and is administered such agent as a time at which severe symptoms of CRS are present. Many of these other approaches also do not prevent other forms of toxicity such as neurotoxicity, which can be associated with adoptive cell therapy.

In some cases, this is at a time where such symptoms are severe, and that therefore may require even harsher or more extreme treatments (e.g. higher dosages or an increased frequency of administration) to ameliorate or treat the toxicity.

The use of certain alternative approaches does not provide satisfactory solutions to such issues. In some cases, such agents and therapies (e.g. steroids) are themselves associated with toxic side effects. Such side effects may be even greater at the higher dose or frequency in which is it necessary to administer or treat with the agent or therapy in order to treat or ameliorate the severity of the toxicity that can result from cell therapy. In addition, in some cases, it is believed that an agent or therapy for treating a toxicity may limit the efficacy of the cell therapy, such as the efficacy of the chimeric receptor (e.g. CAR) expressed on cells provided as part of the cell therapy (Sentman (2013) Immunotherapy, 5:10).

The provided methods offer advantages over available approaches. In some embodiments, the provided methods involve the early or preemptive treatment of subjects prior to the subjects exhibiting physical signs or symptom of toxicity that are more than mild, such as prior to exhibiting physical signs or symptoms of severe toxicity. In some embodiments, the treatment occurs at a time in which a physical sign or symptom of mild CRS, such as grade 1 CRS is present, but before moderate or severe CRS has developed or before grade 2 or grade 3 CRS has developed. In some embodiments, the treatment occurs at a time in which a physical sign or symptom of mild neurotoxicity, such as grade 1 neurotoxicity is present, but before moderate or severe neurotoxicity has developed or before grade 2 or grade 3 neurotoxicity has developed. In some embodiments, the treatment with the toxicity-targeting agent(s) occurs at a time at which no physical signs or symptom of neurotoxicity has developed. Thus, in some cases, the provided methods provide the ability to intervene early before undesired CNS-related outcomes can result. In some cases, the ability to intervene early in the treatment of a toxic outcome or the potential of a toxic outcome can mean that a reduced dosage of a toxicity-targeting agent for treating or ameliorating the toxicity can be given and/or a decreased frequency of administration of such agent or therapy can be given.

In some embodiments, the provided methods include administering a toxicity-targeting agent to a subject that has been administered with a therapy, such as an immunotherapy (immune-therapy) or a cell therapy. In some embodiments, the toxicity-targeting agent is an agent that is capable of treating, preventing, delaying or attenuating the development of a toxicity in the subject. Exemplary of such toxicity-targeting agents are described below.

In some embodiments, the toxicity-targeting agent is administered (i) at a time that is less than or no more than ten, seven, six, five, four or three days after initiation of the administration of the therapy. In some embodiments, the toxicity-targeting agent is administered at a time at which the subject does not exhibit a sign or symptom of severe cytokine release syndrome (CRS) and/or does not exhibit grade 2 or higher CRS. In some embodiments, between the time of the initiation of the administration of the therapy, e.g. cell therapy, and the time of the administration of the toxicity-targeting agent, the subject has not exhibited severe CRS and/or does not exhibit grade 2 or higher CRS. In some embodiments, the toxicity-targeting agent is administered at a time at which the subject does not exhibit a sign or symptom of severe neurotoxicity and/or does not exhibit grade 2 or higher neurotoxicity. In some embodiments, between the time of the initiation of the administration of the therapy, e.g. cell therapy, and the time of the administration of the toxicity-targeting agent, the subject has not exhibited severe neurotoxicity and/or does not exhibit grade 2 or higher CRS.

In some embodiments, the provided methods are designed to or include features that result in a lower degree of toxicity, toxic outcome or symptom, toxicity-promoting profile, factor, or property, such as a symptom or outcome associated with or indicative of cytokine release syndrome (CRS) or neurotoxicity, for example, compared to administration of the therapy at a time in which the subject is administered the agent or other treatment after severe CRS has developed or after grade 2 or higher CRS has developed.

In some aspects, the toxic outcome of a therapy, such as a cell therapy, is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure.

Outcomes, signs and symptoms of CRS are known and include those described herein. In some embodiments, where a particular dosage regimen or administration effects or does not effect a given CRS-associated outcome, sign, or symptom, particular outcomes, signs, and symptoms and/or quantities or degrees thereof may be specified.

In the context of administering CAR-expressing cells, CRS, such as severe CRS, typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-10, IL-6, IL-8, and IL-10.

CRS criteria that appear to correlate with the onset of CRS to predict which patients are more likely to be at risk for developing sCRS have been developed (see Davila et al. Science translational medicine. 2014; 6(224):224ra25). Factors include fevers, hypoxia, hypotension, neurologic changes, elevated serum levels of inflammatory cytokines, such as a set of seven cytokines (IFNγ, IL-5, IL-6, IL-10, Flt-3L, fractalkine, and GM-CSF) whose treatment-induced elevation can correlate well with both pretreatment disease burden, e.g., tumor burden and sCRS symptoms. Other guidelines on the diagnosis and management of CRS are known (see e.g., Lee et al, Blood. 2014; 124(2):188-95). In some embodiments, the criteria reflective of CRS grade are those detailed in Table 1 below.

TABLE 1

Exemplary Grading Criteria for CRS

| Grade | Description of Symptoms |
|---|---|
| 1 Mild | Not life-threatening, require only symptomatic treatment such as antipyretics and anti-emetics (e.g., fever, nausea, fatigue, headache, myalgias, malaise) |
| 2 Moderate | Require and respond to moderate intervention: Oxygen requirement <40%, or Hypotension responsive to fluids or low dose of a single vasopressor, or Grade 2 organ toxicity (by CTCAE v4.0) |
| 3 Severe | Require and respond to aggressive intervention: Oxygen requirement ≥40%, or Hypotension requiring high dose of a single vasopressor (e.g., norepinephrine ≥20 μg/kg/min, dopamine ≥10 μg/kg/min, phenylephrine ≥200 μg/kg/min, or epinephrine ≥10 μg/kg/min), or Hypotension requiring multiple vasopressors (e.g., vasopressin + one of the above agents, or combination vasopressors equivalent to ≥20 μg/kg/min norepinephrine), or Grade 3 organ toxicity or Grade 4 transaminitis (by CTCAE v4.0) |
| 4 Life-threatening | Life-threatening: Requirement for ventilator support, or Grade 4 organ toxicity (excluding transaminitis) |
| 5 Fatal | Death |

In some embodiments, a subject is deemed to develop "severe CRS" ("sCRS") in response to or secondary to administration of a cell therapy or dose of cells thereof, if, following administration, the subject displays: (1) fever of at least 38 degrees Celsius for at least three days; (2) cytokine elevation that includes either (a) a max fold change of at least 75 for at least two of the following group of seven cytokines compared to the level immediately following the administration: interferon gamma (IFNγ), GM-CSF, IL-6, IL-10, Flt-3L, fracktalkine, and IL-5 and/or (b) a max fold change of at least 250 for at least one of the following group of seven cytokines compared to the level immediately following the administration: interferon gamma (IFNγ), GM-CSF, IL-6, IL-10, Flt-3L, fracktalkine, and IL-5; and (c) at least one clinical sign of toxicity such as hypotension (requiring at least one intravenous vasoactive pressor) or hypoxia (PO2 <90%) or one or more neurologic disorder(s) (including mental status changes, obtundation, and/or seizures). In some embodiments, severe CRS includes CRS with a grade of 3 or greater, such as set forth in Table 1.

In some embodiments, outcomes associated with severe CRS or grade 3 CRS or greater, such as grade 4 or greater, such as set forth in Table 1. In some embodiments, these include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen (PO2) levels of less than at or about 90%); and/or one or more neurologic disorders (including mental status changes, obtundation, and seizures). In some embodiments, severe CRS includes CRS that requires management or care in the intensive care unit (ICU).

In some embodiments, severe CRS encompasses a combination of (1) persistent fever (fever of at least 38 degrees Celsius for at least three days) and (2) a serum level of CRP of at least at or about 20 mg/dL. In some embodiments, severe CRS encompasses hypotension requiring the use of two or more vasopressors or respiratory failure requiring mechanical ventilation. In some embodiments, the dosage of vasopressors is increased in a second or subsequent administration.

In some embodiments, severe CRS or grade 3 CRS encompasses an increase in alanine aminotransferase, an increase in aspartate aminotransferase, chills, febrile neutropenia, headache, left ventricular dysfunction, encephalopathy, hydrocephalus, and/or tremor.

In some embodiments, the provided methods involve early interventions prior to the development of severe CRS in the subject or prior to the development of grade 2 or grade 3 CRS. In some embodiments, it is understood that physical signs or symptoms of CRS may exist, but such signs or symptoms are generally mild and/or are not severe. In some embodiments, the toxicity-targeting agent is administered at a time at which the subject exhibits grade 1 CRS or is administered within 24 hours after the subject exhibits a first sign or symptom of grade 1 CRS. In some embodiments, the subject is administered a toxicity-targeting agent at a time at which a first sustained fever has developed or a time at which is within 1 hours, 2 hours, 3 hours, 4 hours, 5 hours, 6 hours, 7 hours, 8 hours, 9 hours, 10 hours, 12 hours, 18 hours or 24 hours of a fever, such as a sustained fever.

In some embodiments, the subject exhibits a fever, and in some aspects is treated at a time at which the subject exhibits such fever and/or exhibits or has exhibited the fever for a particular period of time.

In some embodiments, the fever in the subject is characterized as a body temperature of the subject that is (or is measured at) at or above a certain threshold temperature or level. In some aspects, the threshold temperature is that associated with at least a low-grade fever, with at least a moderate fever, and/or with at least a high-grade fever. In some embodiments, the threshold temperature is a particular temperature or range. For example, the threshold temperature may be at or about or at least at or about 38, 39, 40, 41, or 42 degrees Celsius, and/or may be a range of at or about 38 degrees Celsius to at or about 39 degrees Celsius, a range of at or about 39 degrees Celsius to at or about 40 degrees Celsius, a range of at or about 40 degrees Celsius to at or about 41 degrees, or a range of at or about 41 degrees Celsius to at or about 42 degrees Celsius.

In some embodiments, the fever is a sustained fever; in some aspects, the subject is treated at a time at which a subject has been determined to have a sustained fever, such as within one, two, three, four, five six, or fewer hours of such determination or of the first such determination following the initial therapy having the potential to induce the toxicity, such as the disease-targeted therapy.

In some embodiments, the subject has, and/or is determined to or considered to have, a sustained fever if he or she exhibits a fever at or above the relevant threshold temperature, and where the fever or body temperature of the subject does not fluctuate by about, or by more than about, 1° C., and generally does not fluctuate by about, or by more than about, 0.5° C., 0.4° C., 0.3° C., or 0.2° C. Such absence of fluctuation above or at a certain amount generally is measured over a given period of time (such as over a 24-hour, 12-hour, 8-hour, 6-hour, 3-hour, or 1-hour period of time, which may be measured from the first sign of fever or the first temperature above the indicated threshold). For example, in some embodiments, a subject is considered to or is determined to exhibit sustained fever if he or she exhibits a fever of at least at or about or at least at or about 38 or 39 degrees Celsius, which does not fluctuate in temperature by more than at or about 0.5° C., 0.4° C., 0.3° C., or 0.2° C., over a period of 6 hours, over a period of 8 hours, or over a period of 12 hours, or over a period of 24 hours.

In some embodiments, the subject has, and/or is determined to or considered to have, a sustained fever if he or she exhibits a fever at or above the relevant threshold temperature, and where the fever or body temperature of the subject is not reduced, or is not reduced by or by more than a specified amount (e.g., by more than 1° C., and generally does not fluctuate by about, or by more than about, 0.5° C., 0.4° C., 0.3° C., or 0.2° C.), following a specified treatment, such as a treatment designed to reduce fever such as treatment with an antipyretic. An antipyretic may include any agent, e.g., compound, composition, or ingredient, that reduces fever, such as one of any number of agents known to have antipyretic effects, such as NSAIDs (such as ibuprofen, naproxen, ketoprofen, and nimesulide), salicylates, such as aspirin, choline salicylate, magnesium salicylate, and sodium salicylate, paracetamol, acetaminophen, Metamizole, Nabumetone, Phenaxone, antipyrine, febrifuges. In some embodiments, the antipyretic is acetaminophen. In some embodiments, acetaminophen can be administered at a dose of 12.5 mg/kg orally or intravenously up to every four hours. In some embodiments, it is or comprises ibuprofen or aspirin. For example, a subject is considered to have a sustained fever if he or she exhibits or is determined to exhibit a fever of at least at or about 38 or 39 degrees Celsius, which is not reduced by or is not reduced by more than at or about 0.5° C., 0.4° C., 0.3° C., or 0.2° C., or by at or about 1%, 2%, 3%, 4%, or 5%, over a period of 6 hours, over a period of 8 hours, or over a period of 12 hours, or over a period of 24 hours, even following treatment with the antipyretic such as acetaminophen. In some embodiments, the dosage of the antipyretic is a dosage ordinarily effective in such as subject to reduce fever or fever of a particular type such as fever associated with a bacterial or viral infection, e.g., a localized or systemic infection.

In some embodiments, one or more of the toxicity-targeting therapies is administered at a time at which or immediately after which the subject is determined to or confirmed to (such as is first determined or confirmed to) exhibit sustained fever, for example, as measured according to any of the aforementioned embodiments. In some embodiments, the one or more toxicity-targeting therapies is administered within a certain period of time of such confirmation or determination, such as within 30 minutes, 1 hour, 2 hours, 3 hours, 4 hours, 6 hours, or 8 hours thereof.

In some embodiments, the toxicity-targeting agent is administered prior to a physical sign or symptom of neurotoxicity. In some cases, neurotoxicity, including severe neurotoxity, is a toxic outcome that can be associated with administration of various therapies, such as cell therapies.

In some embodiments, symptoms associated with a clinical risk of neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli *Nature Reviews Neurology* 6, 657-666 (December 2010); National Cancer Institute-Common Toxicity Criteria version 4.03 (NCI-CTCAE v4.03).

In some instances, neurologic symptoms may be the earliest symptoms of sCRS. In some embodiments, neurologic symptoms are seen to begin 5 to 7 days after cell therapy infusion. In some embodiments, duration of neurologic changes may range from 3 to 19 days. In some cases, recovery of neurologic changes occurs after other symptoms of sCRS have resolved. In some embodiments, time or degree of resolution of neurologic changes is not hastened by treatment with anti-IL-6 and/or steroid(s).

In some embodiments, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 2.

TABLE 2

Exemplary Grading Criteria for neurotoxicity

| Grade | Description of Symptoms |
| --- | --- |
| 1 Asymptomatic or Mild | Mild or asymptomatic symptoms |
| 2 Moderate | Presence of symptoms that limit instrumental activities of daily living (ADL), such as preparing meals, shopping for groceries or clothes, using the telephone, managing money |
| 3 Severe | Presence of symptoms that limit self-care ADL, such as bathing, dressing and undressing, feeding self, using the toilet, taking medications |
| 4 Life-threatening | Symptoms that are life-threatening, requiring urgent intervention |
| 5 Fatal | Death |

In some embodiments, the methods reduce symptoms, outcomes or factors associated with CRS, including symptoms, outcomes or factors associated with severe CRS or grade 3 or higher CRS, compared to other methods. For example, subjects treated according to the present methods may lack detectable and/or have reduced symptoms, outcomes or factors of CRS, e.g. severe CRS or grade 3 or higher CRS, such as any described, e.g. set forth in Table 1.

In some embodiments, the methods reduce symptoms associated with CNS-outcomes or neurotoxicity compared to other methods. For example, subjects treated according to the present methods may lack detectable and/or have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods in which the administration of the toxicity-targeting agent is administered later and after severe CRS or severe neurotoxicity or other toxic outcomes have developed. In some embodiments, subjects treated according to the present methods may have reduced symptoms associated with peripheral motor neuropathy, peripheral sensory neuropathy, dysethesia, neuralgia or paresthesia.

In some embodiments, the methods reduce outcomes associated with neurotoxicity including damages to the nervous system and/or brain, such as the death of neurons. In some aspects, the methods reduce the level of factors associated with neurotoxicity such as beta amyloid (Aβ), glutamate, and oxygen radicals.

In some embodiments, subjects administered the therapy in conjunction with an early intervention with a toxicity-targeting agent have reduced symptoms, outcomes, or factors associated with CRS or associated with a CNS-related outcome or neurotoxicity (e.g. severe neurotoxicity or grade 3 or higher neurotoxicity) compared to a method comprising an alternative treatment regimen wherein the subject is administered the agent or other treatment after severe CRS has developed or after grade 2 or higher CRS or grade 2 or higher neurotoxicity has developed. In some embodiments, the CRS (e.g. severe CRS or grade 3 or higher CRS) or CNS-related or neurotoxicity (e.g. severe neurotoxicity or grade 3 or higher neurotoxicity) outcome is reduced by greater than 50%, 60%, 70%, 80%, 90% or more.

In some embodiments, administration of the cell therapy causes one more adverse events. In some embodiments, the adverse event includes, but is not limited to, an increase in alanine aminotransferase, an increase in aspartate aminotransferase, chills, febrile neutropenia, headache, hypotension, left ventricular dysfunction, encephalopathy, hydrocephalus, seizure, and/or tremor. In some embodiments, the intervention methods provided herein ameliorate or reduce such adverse events.

In some embodiments, the provided methods include administration of a toxicity-targeting agent for ameliorating a toxic outcome (e.g. an agent for ameliorating neurotoxicity or CRS, such as severe neurotoxicity or severe CRS) at a dosage that is reduced or less than the dosage of such agent administered to a subject at a time when a physical sign or symptom of severe CRS or neurotoxicity has developed and/or at a time at which the subject exhibits grade 2 or grade 3 CRS or neurotoxicity and/or at a time that is greater than 6, 7, 8, 9, 10, 11, 12, 13 or 14 days after administration or initiation of a cell therapy or after administration or initiation of a first dose of cell therapy. In some embodiments, the reduction in the dose is at least 1.2-fold, 1.3-fold, 1.4-fold, 1.5-fold, 2-fold, 3-fold, 4-fold, 5-fold, 6-fold, 7-fold, 8-fold, 9-fold or 10-fold.

In some embodiments, the provided methods include administration of the toxicity-targeting agent at a frequency in a dosage cycle or regimen that is decreased compared to the frequency of administration of an agent in a dosage cycle or regimen of such agent that is initiated at a time when a physical sign or symptom of severe CRS or neurotoxicity has developed and/or at a time at which the subject exhibits grade 2 or grade 3 CRS or neurotoxicity and/or at a time that is greater than 3 days (e.g. greater than 3 to 14 days, such as greater than 3, 4, 5, 6, 7, 8, 9, 10, 11, 12, 13 or 14 days) after administration or initiation of a cell therapy or after administration or initiation of a first dose of cell therapy. In some embodiments, where a reference regimen or cycle of treatment of an agent (e.g. steroid) involves administration for 3 days, the decrease in the frequency of administration can be to administration for 1 day or for 2 days.

In some embodiments, the provided methods are associated with the administration of a cell therapy, e.g., administration of cells in adoptive cell therapy, such as for the treatment of diseases or conditions including various tumors. The methods involve administering engineered cells expressing recombinant receptors designed to recognize and/or specifically bind to molecules associated with the disease or condition and result in a response, such as an immune response against such molecules upon binding to such molecules. The receptors may include chimeric receptors, e.g., chimeric antigen receptors (CARs), and other transgenic antigen receptors including transgenic T cell receptors (TCRs). In some embodiments, the provided methods are followed by an early intervention therapy for treating a toxicity in the subject after initiation of the cell therapy as described, such as where the early intervention is initiated before a sign or symptom of grade 2 or higher CRS or a severe CRS or before a sign or symptom of grade 2 or higher neurotoxicity or severe neurotoxicity has developed.

A. Cell Therapy and Engineered Cells

In some aspects, the provided therapeutic methods involve administering cells expressing a recombinant receptor, and compositions thereof, to subjects, e.g., patients. In some embodiments, the cells contain or are engineered to contain an engineered receptor, e.g., an engineered antigen receptor, such as a chimeric antigen receptor (CAR), or a T cell receptor (TCR). The cells include populations of such cells, compositions containing such cells and/or enriched for such cells, such as in which cells of a certain type such as T cells or CD8+ or CD4+ cells are enriched or selected. Among the compositions are pharmaceutical compositions and formulations for administration, such as for adoptive cell therapy.

In some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

1. Recombinant Receptors

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

a. Chimeric Antigen Receptors (CARs)

Exemplary antigen receptors, including CARs, and methods for engineering and introducing such receptors into cells, include those described, for example, in International Patent Application Publication Numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282. The chimeric receptors, such as CARs, generally include an extracellular antigen binding domain, such as a portion of an antibody molecule, generally a variable heavy (VH) chain region and/or variable light (VL) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

Antigens targeted by the receptors in some embodiments include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the CAR binds a pathogen-specific antigen. In some embodiments, the CAR is specific for viral antigens (such as HIV, HCV, HBV, etc.), bacterial antigens, and/or parasitic antigens.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in International Patent Application Publication Number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) *Clin. Cancer Res.*, 19:3153, International Patent Application Publication Number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 or 5.

This antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor 7, CD8, CD4, CD25, or CD16. For example, in some aspects, the CAR or other chimeric receptor includes a chimeric molecule between CD3-zeta (CD3-ζ) or Fc receptor 7 and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD8, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in International Patent Application Publication Number WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. An exemplary T2A linker sequence comprises the sequence of amino acids set forth in SEQ ID NO: 6 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. PO1747.1) or variant thereof, such as a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190 or U.S. Pat. No. 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 4. In some embodiments, the spacer is an Ig hinge, e.g., an IgG4 hinge, linked to a CH3 domain only, such as set forth in SEQ ID NO: 3. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802, 374). In some embodiments, the sequence encodes an tEGFR sequence set forth in SEQ ID NO: 7 or 16, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

b. TCRs

In some embodiments, the genetically engineered antigen receptors include recombinant T cell receptors (TCRs) and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy: The Journal of the American Society of Gene Therapy. 18:1748-1757; an Hackett et al. (2010) Molecular Therapy: The Journal of the American Society of Gene Therapy. 18:674-683.

c. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in International Patent Application Publication No: WO 2014055668 A1 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

2. Cells and Preparation of Cells for Genetic Engineering

Among the cells expressing the receptors and administered in the provided methods are engineered cells. The genetic engineering generally involves introduction of a nucleic acid encoding the recombinant or engineered component into a composition containing the cells, such as by retroviral transduction, transfection, or transformation.

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using anti-CD3/anti-CD28 antibody conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^- CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application Publication Number WO2009/072003, or US Patent Application Publication Number US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., International Patent Application Publication Number WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to $-80°$ C. at a rate of $1°$ per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL. In some aspects, the IL-2 concentration is at least about 10 units/mL. In some embodiments, the stimulating agents include PMA and ionomycin.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

3. Vectors and Methods for Genetic Engineering

Various methods for the introduction of genetically engineered components, e.g., recombinant receptors, e.g., CARs or TCRs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in International Patent Application Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

In some aspects, the cells further are engineered to promote expression of cytokines or other factors. Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization;

genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the subject to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

B. Compositions and Formulations

In some embodiments, the immunotherapy and/or a cell therapy is provided as a composition or formulation, such as a pharmaceutical composition or formulation. Such compositions can be used in accord with the provided methods, such as in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some embodiments, the T cell therapy, such as engineered T cells (e.g. CAR T cells), are formulated with a pharmaceutically acceptable carrier. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being prevented or treated with the cells, including one or more active ingredients where the activities are complementary to the cells and/or the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The pharmaceutical composition in some embodiments contain cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The cells may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

C. Treatment and Methods

In some embodiments, the immunotherapy and/or a cell therapy, e.g., a dose of cells expressing a recombinant receptor are administered to a subject to treat or prevent diseases, conditions, and disorders, including cancers. In some embodiments, the immunotherapy and/or a cell therapy, e.g., cells, populations, and compositions are administered to a subject or patient having the particular disease or condition to be treated, e.g., via adoptive cell therapy, such as adoptive T cell therapy. In some embodiments, cells and compositions, such as engineered compositions and end-of-production compositions following incubation and/or other processing steps, are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell. In some embodiments, the provided methods include an early or preemptive intervention or interventions, including by administration of agents or therapies or other treatments that are administered in addition to the immunotherapy and/or cell therapy.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, and parasitic disease, and autoimmune and inflammatory diseases. In some embodiments, the disease or condition is a tumor, cancer, malignancy, neoplasm, or other proliferative disease or disorder. Such diseases include but are not limited to leukemia, lymphoma, e.g., chronic lymphocytic leukemia (CLL), acute-lymphoblastic leukemia (ALL), non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma. In some embodiments, the subject has acute-lymphoblastic leukemia (ALL). In some embodiments, the subject has non-Hodgkin's lymphoma.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In some embodiments, the methods comprise administration of a chemotherapeutic agent, e.g., a conditioning chemotherapeutic agent, for example, to reduce tumor burden prior to the administration.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days.

In some embodiments, where the lymphodepleting agent comprises fludarabine, the subject is administered fludarabine at a dose between or between about 1 mg/m$^2$ and 100 mg/m$^2$, such as between or between about 10 mg/m$^2$ and 75 mg/m$^2$, 15 mg/m$^2$ and 50 mg/m$^2$, 20 mg/m$^2$ and 30 mg/m$^2$, or 24 mg/m$^2$ and 26 mg/m$^2$. In some instances, the subject is administered 25 mg/m² of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m²) of cyclophosphamide and 3 to 5 doses of 25 mg/m² fludarabine prior to the first or subsequent dose.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

1. Dosing

The pharmaceutical composition in some embodiments of the methods provided herein contains the cells in amounts effective to treat or prevent the disease or condition, such as a therapeutically effective or prophylactically effective amount. In some embodiments, the composition includes the cells in an amount effective to reduce burden of the disease or condition.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, which is no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the first dose.

The term "split dose" refers to a dose that is split so that it is administered over more than one day. This type of dosing is encompassed by the present methods and is considered to be a single dose.

Thus, the dose in some aspects may be administered as a split dose. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the first dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, one or more consecutive or subsequent dose of cells can be administered to the subject. In some embodiments, the consecutive or subsequent dose of cells is administered greater than or greater than about 7 days, 14 days, 21 days, 28 days or 35 days after initiation of administration of the first dose of cells. The consecutive or subsequent dose of cells can be more than, approximately the same as, or less than the first dose. In some embodiments, administration of the T cell therapy, such as administration of the first and/or second dose of cells, can be repeated.

In some embodiments, a dose of cells is administered to subjects in accord with the provided methods. In some embodiments, the size or timing of the doses is determined as a function of the particular disease or condition in the subject. It is within the level of a skilled artisan to empirically determine the size or timing of the doses for a particular disease. Dosages may vary depending on attributes particular to the disease or disorder and/or patient and/or other treatments.

In certain embodiments, the cells, or individual populations of sub-types of cells, are administered to the subject at a range of about 0.1 million to about 100 billion cells and/or that amount of cells per kilogram of body weight of the subject, such as, e.g., about 0.1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight of the subject. Dosages may vary depending on attributes particular to the disease or disorder and/or patient and/or other treatments. In some embodiments, such values refer to numbers of recombinant receptor-expressing cells; in other embodiments, they refer to number of T cells or PBMCs or total cells administered.

In some embodiments, the cell therapy comprises administration of a dose comprising a number of cells that is at least or at least about or is or is about $0.1 \times 10^6$ cells/kg body weight of the subject, $0.2 \times 10^6$ cells/kg, $0.3 \times 10^6$ cells/kg, $0.4 \times 10^6$ cells/kg, $0.5 \times 10^6$ cells/kg, $1 \times 10^6$ cell/kg, $2.0 \times 10^6$ cells/kg, $3 \times 10^6$ cells/kg or $5 \times 10^6$ cells/kg.

In some embodiments, the cell therapy comprises administration of a dose comprising a number of cells is between or between about $0.1 \times 10^6$ cells/kg body weight of the subject and $1.0 \times 10^7$ cells/kg, between or between about $0.5 \times 10^6$ cells/kg and $5 \times 10^6$ cells/kg, between or between about $0.5 \times 10^6$ cells/kg and $3 \times 10^6$ cells/kg, between or between about $0.5 \times 10^6$ cells/kg and $2 \times 10^6$ cells/kg, between or between about $0.5 \times 10^6$ cells/kg and $1 \times 10^6$ cell/kg, between or between about $1.0 \times 10^6$ cells/kg body weight of the subject and $5 \times 10^6$ cells/kg, between or between about $1.0 \times 10^6$ cells/kg and $3 \times 10^6$ cells/kg, between or between about $1.0 \times 10^6$ cells/kg and $2 \times 10^6$ cells/kg, between or between about $2.0 \times 10^6$ cells/kg body weight of the subject and $5 \times 10^6$ cells/kg, between or between about $2.0 \times 10^6$ cells/kg and $3 \times 10^6$ cells/kg, or between or between about $3.0 \times 10^6$ cells/kg body weight of the subject and $5 \times 10^6$ cells/kg, each inclusive.

In some embodiments, the dose of cells comprises between at or about $2 \times 10^5$ of the cells/kg and at or about $2 \times 10^6$ of the cells/kg, such as between at or about $4 \times 10^5$ of the cells/kg and at or about $1 \times 10^6$ of the cells/kg or between at or about $6 \times 10^5$ of the cells/kg and at or about $8 \times 10^5$ of the cells/kg. In some embodiments, the dose of cells comprises no more than $2 \times 10^5$ of the cells (e.g. antigen-expressing, such as CAR-expressing cells) per kilogram body weight of the subject (cells/kg), such as no more than at or about $3 \times 10^5$ cells/kg, no more than at or about $4 \times 10^5$ cells/kg, no more than at or about $5 \times 10^5$ cells/kg, no more than at or about $6 \times 10^5$ cells/kg, no more than at or about $7 \times 10^5$ cells/kg, no more than at or about $8 \times 10^5$ cells/kg, nor more than at or about $9 \times 10^5$ cells/kg, no more than at or about $1 \times 10^6$ cells/kg, or no more than at or about $2 \times 10^6$ cells/kg. In some embodiments, the dose of cells comprises at least or at least about or at or about $2 \times 10^5$ of the cells (e.g. antigen-expressing, such as CAR-expressing cells) per kilogram body weight of the subject (cells/kg), such as at least or at least about or at or about $3 \times 10^5$ cells/kg, at least or at least about or at or about $4 \times 10^5$ cells/kg, at least or at least about or at or about $5 \times 10^5$ cells/kg, at least or at least about or at or about $6 \times 10^5$ cells/kg, at least or at least about or at or about $7 \times 10^5$ cells/kg, at least or at least about or at or about $8 \times 10^5$ cells/kg, at least or at least about or at or about $9 \times 10^5$ cells/kg, at least or at least about or at or about $1 \times 10^6$ cells/kg, or at least or at least about or at or about $2 \times 10^6$ cells/kg.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8$^+$ and CD4$^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4$^+$ to CD8$^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4$^+$ to CD8$^+$ cells, and/or is based on a desired fixed or minimum dose of CD4$^+$ and/or CD8$^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of CD4$^+$ to CD8$^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

II. Toxicity-Targeting Agents that Treat or Ameliorate Symptoms of Toxicity

In some embodiments, the methods include an early or preemptive intervention or interventions, including by administration of agents or therapies or other treatments that treat a toxicity of an immunotherapy and/or a cell therapy, such as CRS or neurotoxicity, e.g. severe CRS or severe neurotoxicity, and/or that prevent, delay, or attenuate the development of or risk for developing CRS or neurotoxicity, e.g., severe CRS or severe neurotoxicity. For example, in some embodiments, the agent is a toxicity-targeting agent or treatment or intervention.

In some embodiments, the agent, e.g., a toxicity-targeting agent, is a steroid, is an antagonist or inhibitor of a cytokine receptor, such as IL-6 receptor, CD122 receptor (IL-2Rbeta receptor), or CCR2, or is an inhibitor of a cytokine, such as IL-6, MCP-1, IL-10, IFN-γ, IL-8, or IL-18. In some embodiments, the agent is an agonist of a cytokine receptor and/or cytokine, such as TGF-β. In some embodiments, the agent, e.g., agonist, antagonist or inhibitor, is an antibody or antigen-binding fragment, a small molecule, a protein or peptide, or a nucleic acid.

In some embodiments, a fluid bolus can be employed as an intervention, such as to treat hypotension associated with CRS. In some embodiments, the target hematocrit levels are >24%. In some embodiments, the intervention includes the use of absorbent resin technology with blood or plasma filtration. In some cases, the intervention includes dialysis, plasmapheresis, or similar technologies. In some embodiments, vassopressors or acetaminophen can be employed.

In some embodiments, the agent can be administered sequentially, intermittently, or at the same time as or in the same composition as the therapy, such as cells for adoptive cell therapy. For example, the agent can be administered before, during, simultaneously with, or after administration of the immunotherapy and/or cell therapy.

In some embodiments, the agent is administered at a time as described herein and in accord with the provided methods. In some embodiments, the toxicity-targeting agent is administered at a time that is within, such as less than or no more than, 3, 4, 5, 6, 7, 8, 9 or 10 days after initiation of the immunotherapy and/or cell therapy. In some embodiments, the toxicity-targeting agent is administered within or within about 1 day, 2 days or 3 days after initiation of administration of the immunotherapy and/or cell therapy.

In some embodiments, the agent, e.g., toxicity-targeting agent, is administered to a subject after initiation of administration of the immunotherapy and/or cell therapy at a time at which the subject does not exhibit grade 2 or higher CRS or grade 2 or higher neurotoxicity. In some aspects, the toxicity-targeting agent is administered after initiation of administration of the immunotherapy and/or cell therapy at a time at which the subject does not exhibit severe CRS or severe neurotoxicity. Thus, in the provided methods, between initiation of administration of the immunotherapy and/or cell therapy and the toxicity-targeting agent, the subject is one that does not exhibit grade 2 or higher CRS, such as severe CRS, and/or does not exhibit grade 2 or higher neurotoxicity, such as severe neurotoxicity.

Non-limiting examples of interventions for treating or ameliorating a toxicity, such as severe CRS (sCRS), are described in Table 3. In some embodiments, the intervention includes tocilizumab or other toxicity-targeting agent as described, which can be at a time in which there is a sustained or persistent fever of greater than or about 38° C. or greater than or greater than about 39° C. in the subject. In some embodiments, the fever is sustained in the subject for more than 10 hours, more than 12 hours, more than 16 hours, or more than 24 hours before intervention.

TABLE 3

| Symptoms related to CRS | Suggested Intervention |
| --- | --- |
| Fever of ≥38.3° C. | Acetaminophen (12.5 mg/kg) PO/IV up to every four hours |
| Persistent fever of ≥39° C. for 10 hours that is unresponsive to acetaminophen | Tocilizumab (8-12 mg/kg) IV |
| Persistent fever of ≥39° C. after tocilizumab | Dexamethasone 5-10 mg IV/PO up to every 6-12 hours with continued fevers |
| Recurrence of symptoms 48 hours after initial dose of tocilizumab | Tocilizumab (8-12 mg/kg) IV |
| Hypotension | Fluid bolus, target hematocrit >24% |
| Persistent/recurrent hypotension after initial fluid bolus (within 6 hours) | Tocilizumab (8-12 mg/kg) IV |
| Use of low dose pressors for hypotension for longer than 12 hours | Dexamethasone 5-10 mg IV/PO up to every 6 hours with continued use of pressors |
| Initiation of higher dose pressors or addition of a second pressor for hypotension | Dexamethasone 5-10 mg IV/PO up to every 6 hours with continued use of pressors |
| Initiation of oxygen supplementation | Tocilizumab (8-12 mg/kg) IV |
| Symptoms related to CRS | Suggested Intervention |
| Increasing respiratory support with concern for impending intubation | Dexamethasone 5-10 mg IV/PO up to every 6 hours with continued use of pressors |
| Recurrence/Persistence of symptoms for which tocilizumab was given ≥48 hours after initial dose was administered | Tocilizumab (8-12 mg/kg) IV |

In some cases, the agent or therapy or intervention, e.g., toxicity-targeting agent, is administered alone or is administered as part of a composition or formulation, such as a pharmaceutical composition or formulation, as described herein. Thus, the agent alone or as part of a pharmaceutical composition can be administered intravenously or orally, or by any other acceptable known route of administration or as described herein.

In some embodiments, the dosage of agent or the frequency of administration of the agent in a dosage regimen is reduced compared to the dosage of the agent or its frequency in a method in which a subject is treated with the agent after grade 2 or higher CRS or neurotoxicity, such as after severe, e.g., grade 3 or higher, CRS or after severe, e.g., grade 3 or higher neurotoxicity, has developed or been diagnosed (e.g. after physical signs or symptoms of grade 3 or higher CRS or neurotoxicity has manifested). In some embodiments, the dosage of agent or the frequency of administration of the agent in a dosage regimen is reduced compared to the dosage of the agent or its frequency in a method in which a subject is treated for CRS or neurotoxicity greater than 3 days, 4 days, 5 days, 6 days, 1 week, 2 weeks, three weeks, or more after administration of the immunotherapy and/or cell therapy. In some embodiments, the dosage is reduced by greater than or greater than about 1.2-fold, 1.5-fold, 2-fold, 3-fold, 4-fold, 5-fold, 6-fold, 7-fold, 8-fold, 9-fold, 10-fold or more. In some embodiments, the dosage is reduced by greater than or about 10%, 20%, 30%, 40%, 50%, 60%, 70%, 80%, 90%, or more. In some embodiments, the frequency of dosing is reduced, such as the number of daily doses is reduced or the number of days of dosing is reduced.

A. Toxicity-Targeting Agents

1. Steroid

In some embodiments, the agent, e.g., toxicity-targeting agent, that treats and/or that prevents, delays, or attenuates the development of or risk for developing a toxicity to an immunotherapy and/or a cell therapy, such as grade 2 or higher or severe CRS or neurotoxicity, is a steroid, e.g., corticosteroid. Corticosteroids typically include glucocorticoids and mineralocorticoids.

Any corticosteroid, e.g., glucocorticoid, can be used in the methods provided herein. In some embodiments, glucocorticoids include synthetic and non-synthetic glucocorticoids. Exemplary glucocorticoids include, but are not limited to: alclomethasones, algestones, beclomethasones (e.g. beclomethasone dipropionate), betamethasones (e.g. betamethasone 17-valerate, betamethasone sodium acetate, betamethasone sodium phosphate, betamethasone valerate), budesonides, clobetasols (e.g. clobetasol propionate), clobetasones, clocortolones (e.g. clocortolone pivalate), cloprednols, corticosterones, cortisones and hydrocortisones (e.g. hydrocortisone acetate), cortivazols, deflazacorts, desonides, desoximethasones, dexamethasones (e.g. dexamethasone 21-phosphate, dexamethasone acetate, dexamethasone sodium phosphate), diflorasones (e.g. diflorasone diacetate), diflucortolones, difluprednates, enoxolones, fluazacorts, flucloronides, fludrocortisones (e.g., fludrocortisone acetate), flumethasones (e.g. flumethasone pivalate), flunisolides, fluocinolones (e.g. fluocinolone acetonide), fluocinonides, fluocortins, fluocortolones, fluorometholones (e.g. fluorometholone acetate), fluperolones (e.g., fluperolone acetate), fluprednidenes, fluprednisolones, flurandrenolides, fluticasones (e.g. fluticasone propionate), formocortals, halcinonides, halobetasols, halometasones, halopredones, hydrocortamates, hydrocortisones (e.g. hydrocortisone 21-butyrate, hydrocortisone aceponate, hydrocortisone acetate, hydrocortisone buteprate, hydrocortisone butyrate, hydrocortisone cypionate, hydrocortisone hemisuccinate, hydrocortisone probutate, hydrocortisone sodium phosphate, hydrocortisone sodium succinate, hydrocortisone valerate), loteprednol etabonate, mazipredones, medrysones, meprednisones, methylprednisolones (methylprednisolone aceponate, methylprednisolone acetate, methylprednisolone hemisuccinate, methylprednisolone sodium succinate), mometasones (e.g., mometasone furoate), paramethasones (e.g., paramethasone acetate), prednicarbates, prednisolones (e.g. prednisolone 25-diethylaminoacetate, prednisolone sodium phosphate, prednisolone 21-hemisuccinate, prednisolone acetate; prednisolone farnesylate, prednisolone hemisuccinate, prednisolone-21 (beta-D-glucuronide), prednisolone metasulphobenzoate, prednisolone steaglate, prednisolone tebutate, prednisolone tetrahydrophthalate), prednisones, prednivals, prednylidenes, rimexolones, tixocortols, triamcinolones (e.g. triamcinolone acetonide, triamcinolone benetonide, triamcinolone hexacetonide, triamcinolone acetonide 21-palmitate, triamcinolone diacetate). These glucocorticoids and the salts thereof are discussed in detail, for example, in Remington's Pharmaceutical Sciences, A. Osol, ed., Mack Pub. Co., Easton, Pa. (16th ed. 1980).

In some examples, the glucocorticoid is selected from among cortisones, dexamethasones, hydrocortisones, methylprednisolones, prednisolones and prednisones. In a particular example, the glucocorticoid is dexamethasone.

In some embodiments, the agent is a corticosteroid and is administered in an amount that is therapeutically effective to treat, ameliorate or reduce one or more symptoms of a toxicity to an immunotherapy and/or a cell therapy, such as CRS or neurotoxicity. In some embodiments, indicators of improvement or successful treatment include determination of the failure to manifest a relevant score on toxicity grading scale (e.g. CRS or neurotoxicity grading scale), such as a score of less than 3, or a change in grading or severity on the grading scale as discussed herein, such as a change from a score of 4 to a score of 3, or a change from a score of 4 to a score of 2, 1 or 0.

In some aspects, the corticosteroid is provided in a therapeutically effective dose. Therapeutically effective concentration can be determined empirically by testing in known in vitro or in vivo (e.g. animal model) systems. For example, the amount of a selected corticosteroid to be administered to ameliorate symptoms or adverse effects of a toxicity to an immunotherapy and/or a cell therapy, such as CRS or neurotoxicity, can be determined by standard clinical techniques. In addition, animal models can be employed to help identify optimal dosage ranges. The precise dosage, which can be determined empirically, can depend on the particular therapeutic preparation, the regime and dosing schedule, the route of administration and the seriousness of the disease.

The corticosteroid can be administered in any amount that is effective to ameliorate one or more symptoms associated with the toxicity, such as with the CRS or neurotoxicity. The corticosteroid, e.g., glucocorticoid, can be administered, for example, at an amount between at or about 0.1 and 100 mg, per dose, 0.1 to 80 mg, 0.1 to 60 mg, 0.1 to 40 mg, 0.1 to 30 mg, 0.1 to 20 mg, 0.1 to 15 mg, 0.1 to 10 mg, 0.1 to 5 mg, 0.2 to 40 mg, 0.2 to 30 mg, 0.2 to 20 mg, 0.2 to 15 mg, 0.2 to 10 mg, 0.2 to 5 mg, 0.4 to 40 mg, 0.4 to 30 mg, 0.4 to 20 mg, 0.4 to 15 mg, 0.4 to 10 mg, 0.4 to 5 mg, 0.4 to 4 mg, 1 to 20 mg, 1 to 15 mg or 1 to 10 mg, to a 70 kg adult human subject. Typically, the corticosteroid, such as a glucocorticoid is administered at an amount between at or about 0.4 and 20 mg, for example, at or about 0.4 mg, 0.5 mg, 0.6 mg, 0.7 mg, 0.75 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg per dose, to an average adult human subject.

In some embodiments, the corticosteroid can be administered, for example, at a dosage of at or about 0.001 mg/kg (of the subject), 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.025 mg/kg, 0.03 mg/kg, 0.035 mg/kg, 0.04 mg/kg, 0.045 mg/kg, 0.05 mg/kg, 0.055 mg/kg, 0.06 mg/kg, 0.065 mg/kg, 0.07 mg/kg, 0.075 mg/kg, 0.08 mg/kg, 0.085 mg/kg, 0.09 mg/kg, 0.095 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1 mg/kg, 1.05 mg/kg, 1.1 mg/kg, 1.15 mg/kg, 1.20 mg/kg, 1.25 mg/kg, 1.3 mg/kg, 1.35 mg/kg or 1.4 mg/kg, to an average adult human subject, typically weighing about 70 kg to 75 kg.

The corticosteroid, or glucocorticoid, for example dexamethasone, can be administered orally (tablets, liquid or liquid concentrate), PO, intravenously (IV), intramuscularly or by any other known route or route described herein (e.g., with respect to pharmaceutical formulations). In some aspects, the corticosteroid is administered as a bolus, and in other aspects it may be administered over a period of time.

In some aspects, the glucocorticoid can be administered over a period of more than one day, such as over two days, over 3 days, or over 4 or more days. In some embodiments, the corticosteroid can be administered one per day, twice per day, or three times or more per day. For example, the corticosteroid, e.g., dexamethasone, may in some examples be administered at 10 mg (or equivalent) IV twice a day for three days.

In some embodiments, the dosage of corticosteroid, e.g., glucocorticoid, is administered in successively lower dosages per treatment. Hence, in some such treatment regimes, the dose of corticosteroid is tapered. For example, the corticosteroid may be administered at an initial dose (or equivalent dose, such as with reference to dexamethasone) of 4 mg, and upon each successive administration the dose may be lowered, such that the dose is 3 mg for the next administration, 2 mg for the next administration, and 1 mg for the next administration Generally, the dose of corticosteroid administered is dependent upon the specific corticosteroid, as a difference in potency exists between different corticosteroids. It is typically understood that drugs vary in potency, and that doses can therefore vary, in order to obtain equivalent effects. Table 4 shows equivalence in terms of potency for various glucocorticoids and routes of administration. Equivalent potency in clinical dosing is well known. Information relating to equivalent steroid dosing (in a non-chronotherapeutic manner) may be found in the British National Formulary (BNF) 37, March 1999.

TABLE 4

| Glucocorticoid administration | |
|---|---|
| Glucocorticoid (Route) | Equivalency Potency |
| Hydrocortisone (IV or PO) | 20 |
| Prednisone | 5 |
| Prednisolone (IV or PO) | 5 |
| Methylprednisolone sodium succinate (IV) | 4 |
| Dexamethasone (IV or PO) | 0.5-0.75 |

Thus, in some embodiments, the steroid is administered in an equivalent dosage amount of from or from about 1.0 mg to 20 mg dexamethasone per day, such as 1.0 mg to 15 mg dexamethasone per day, 1.0 mg to 10 mg dexamethasone per day, 2.0 mg to 8 mg dexamethasone per day, or 2.0 mg to 6.0 mg dexamethasone per day, each inclusive. In some cases, the steroid is administered in an equivalent dose of at or about 4 mg or at or about 8 mg dexamethasone per day.

In some embodiments, the steroid is administered if fever persists after treatment with tocilizumab. For example, in some embodiments, dexamethasone is administered orally or intravenously at a dosage of 5-10 mg up to every 6-12 hours with continued fevers. In some embodiments, tocilizumab is administered concurrently with or subsequent to oxygen supplementation.

2. Other Agents

In some embodiments, the agent, e.g. toxicity-targeting agent, that treats or ameliorates symptoms of a toxicity of immunotherapy and/or a cell therapy, such as CRS or neurotoxicity, is one that targets a cytokine, e.g., is an antagonist or inhibitor of a cytokine, such as transforming growth factor beta (TGF-beta), interleukin 6 (IL-6), interleukin 10 (IL-10), IL-2, MIP1β (CCL4), TNF alpha, IL-1, interferon gamma (IFN-gamma), or monocyte chemoattractant protein-1 (MCP-1). In some embodiments, the agent that treats or ameliorates symptoms of a toxicity of an immunotherapy and/or a cell therapy, such as CRS or neurotoxicity, is one that targets (e.g. inhibits or is an antagonist of) a cytokine receptor, such as IL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1β receptor (e.g., CCR5), TNF alpha receptor (e.g., TNFR1), IL-1 receptor (IL1-Rα/IL-1Rβ), or IL-10 receptor (IL-10R).

The amount of a selected agent that treats or ameliorates symptoms of a toxicity of an immunotherapy and/or a cell therapy, such as CRS or neurotoxicity to be administered to ameliorate symptoms or adverse effects of a toxicity to an immunotherapy and/or a cell therapy, such as CRS or neurotoxicity, can be determined by standard clinical techniques. Exemplary adverse events include, but are not limited to, an increase in alanine aminotransferase, an increase in aspartate aminotransferase, chills, febrile neutropenia, headache, hypotension, left ventricular dysfunction, encephalopathy, hydrocephalus, seizure, and/or tremor.

In some embodiments, the agent is administered in a dosage amount of from or from about 30 mg to 5000 mg, such as 50 mg to 1000 mg, 50 mg to 500 mg, 50 mg to 200 mg, 50 mg to 100 mg, 100 mg to 1000 mg, 100 mg to 500 mg, 100 mg to 200 mg, 200 mg to 1000 mg, 200 mg to 500 mg or 500 mg to 1000 mg.

In some embodiments, the agent is administered from or from about 0.5 mg/kg to 100 mg/kg, such as from or from about 1 mg/kg to 50 mg/kg, 1 mg/kg to 25 mg/kg, 1 mg/kg to 10 mg/kg, 1 mg/kg to 5 mg/kg, 5 mg/kg to 100 mg/kg, 5 mg/kg to 50 mg/kg, 5 mg/kg to 25 mg/kg, 5 mg/kg to 10 mg/kg, 10 mg/kg to 100 mg/kg, 10 mg/kg to 50 mg/kg, 10 mg/kg to 25 mg/kg, 25 mg/kg to 100 mg/kg, 25 mg/kg to 50 mg/kg to 50 mg/kg to 100 mg/kg. In some embodiments, the agent is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive. In some aspects, the agent is administered in a dosage amount of at least or at least about or about 1 mg/kg, 2 mg/kg, 4 mg/kg, 6 mg/kg, 8 mg/kg, 10 mg/kg or more. In some embodiments, the agent is administered at a dose of 4 mg/kg or 8 mg/kg.

In some embodiments, the agent is administered by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

In some embodiments, the amount of the agent is administered about or approximately twice daily, daily, every other day, three times a week, weekly, every other week or once a month.

In some embodiments, the agent is administered as part of a composition or formulation, such as a pharmaceutical composition or formulation as described below. Thus, in some cases, the composition comprising the agent is administered as described below. In other aspects, the agent is administered alone and may be administered by any known acceptable route of administration or by one described herein, such as with respect to compositions and pharmaceutical formulations.

In some embodiments, the agent that treats or ameliorates symptoms of a toxicity of the immunotherapy and/or cell therapy, such as CRS or neurotoxicity, is an antibody or antigen binding fragment. In some embodiments, the agent is tocilizumab, siltuximab, sarilumab, olokizumab (CDP6038), elsilimomab, ALD518/BMS-945429, sirukumab (CNTO 136), CPSI-2634, ARGX-109, FE301, or FM101.

In some embodiments, the agent is an antagonist or inhibitor of IL-6 or the IL-6 receptor (IL-6R). In some aspects, the agent is an antibody that neutralizes IL-6 activity, such as an antibody or antigen-binding fragment that binds to IL-6 or IL-6R. For example, in some embodiments, the agent is or comprises tocilizumab (atlizumab) or sarilumab, anti-IL-6R antibodies. In some embodiments, the agent is an anti-IL-6R antibody described in U.S. Pat. No. 8,562,991. In some cases, the agent that targets IL-6 is an anti-IL-6 antibody, such as siltuximab, elsilimomab, ALD518/BMS-945429, sirukumab (CNTO 136), CPSI-2634, ARGX-109, FE301, FM101, or olokizumab (CDP6038). In some aspects, the agent may neutralize IL-6 activity by inhibiting the ligand-receptor interactions. The feasibility of this general type of approach has been demonstrated with a natural occurring receptor antagonist for interleukin-1. See Harmurn, C. H. et al., Nature (1990) 343:336-340. In some aspects, the IL-6/IL-6R antagonist or inhibitor is an IL-6 mutein, such as one described in U.S. Pat. No. 5,591,827. In some embodiments, the agent that is an antagonist or inhibitor of IL-6/IL-6R is a small molecule, a protein or peptide, or a nucleic acid.

In some embodiments, the agent is tocilizumab. In some embodiments, tocilizumab is administered as an early intervention in accord with the provided methods a dosage of from or from about 1 mg/kg to 12 mg/kg, such as at or about 4 mg/kg, 8 mg/kg, or 10 mg/kg. In some embodiments, tocilizumab is administered by intravenous infusion. In some embodiments, tocilizumab is administered for a persistent fever of greater than 39° C. lasting 10 hours that is unresponsive to acetaminophen. In some embodiments, a second administration of tocilizumab is provided if symptoms recur after 48 hours of the initial dose.

In some embodiments, the agent is an agonist or stimulator of TGF-β or a TGF-β receptor (e.g., TGF-β receptor I, II, or III). In some aspects, the agent is an antibody that increases TGF-β activity, such as an antibody or antigen-binding fragment that binds to TGF-β or one of its receptors. In some embodiments, the agent that is an agonist or stimulator of TGF-β and/or its receptor is a small molecule, a protein or peptide, or a nucleic acid.

In some embodiments, the agent is an antagonist or inhibitor of MCP-1 (CCL2) or a MCP-1 receptor (e.g., MCP-1 receptor CCR2 or CCR4). In some aspects, the agent is an antibody that neutralizes MCP-1 activity, such as an antibody or antigen-binding fragment that binds to MCP-1 or one of its receptors (CCR2 or CCR4). In some embodiments, the MCP-1 antagonist or inhibitor is any described in Gong et al. J Exp Med. 1997 Jul. 7; 186(1): 131-137 or Shahrara et al. J Immunol 2008; 180:3447-3456. In some embodiments, the agent that is an antagonist or inhibitor of MCP-1 and/or its receptor (CCR2 or CCR4) is a small molecule, a protein or peptide, or a nucleic acid.

In some embodiments, the agent is an antagonist or inhibitor of IFN-γ or an IFN-7 receptor (IFNGR). In some aspects, the agent is an antibody that neutralizes IFN-γ activity, such as an antibody or antigen-binding fragment that binds to IFN-γ or its receptor (IFNGR). In some aspects, the IFN-gamma neutralizing antibody is any described in Dobber et al. Cell Immunol. 1995 February; 160(2):185-92 or Ozmen et al. J Immunol. 1993 Apr. 1; 150(7):2698-705. In some embodiments, the agent that is an antagonist or inhibitor of IFN-γ/IFNGR is a small molecule, a protein or peptide, or a nucleic acid.

In some embodiments, the agent is an antagonist or inhibitor of IL-10 or the IL-10 receptor (IL-10R). In some aspects, the agent is an antibody that neutralizes IL-10 activity, such as an antibody or antigen-binding fragment that binds to IL-10 or IL-10R. In some aspects, the IL-10 neutralizing antibody is any described in Dobber et al. Cell Immunol. 1995 February; 160(2):185-92 or Hunter et al. J Immunol. 2005 Jun. 1; 174(11):7368-75. In some embodiments, the agent that is an antagonist or inhibitor of IL-10/IL-10R is a small molecule, a protein or peptide, or a nucleic acid.

B. Compositions and Formulations

In some embodiments, the agents, e.g., toxicity-targeting agents are provided as a composition or formulation, such as a pharmaceutical composition or formulation. Such compositions can be used in accord with the provided methods, such as in an early intervention for the prevention, treatment or amelioration of a toxicity, such as to delay, attenuate, reduce CRS or neurotoxicity in the subject.

In some embodiments, the toxicity-targeting agents are formulated with a pharmaceutical carrier. Such carriers can include, for example, carriers such as a diluent, adjuvant, excipient, or vehicle with which the agent is administered. Examples of suitable pharmaceutical carriers are described in "Remington's Pharmaceutical Sciences" by E. W. Martin. Such compositions will contain a therapeutically effective amount of the agent, generally in purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Saline solutions and aqueous dextrose and glycerol solutions also can be employed as liquid carriers, particularly for injectable solutions. The pharmaceutical compositions can contain any one or more of a diluents(s), adjuvant(s), antiadherent(s), binder(s), coating(s), filler(s), flavor(s), color(s), lubricant(s), glidant(s), preservative(s), detergent(s), sorbent(s), emulsifying agent(s), pharmaceutical excipient(s), pH buffering agent(s), or sweetener(s) and a combination thereof. In some embodiments, the pharmaceutical composition can be liquid, solid, a lyophilized powder, in gel form, and/or combination thereof. In some aspects, the choice of carrier is determined in part by the particular agent and/or by the method of administration.

In some embodiments, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

In some embodiments, the agents are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the agent to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains agents in amounts effective to ameliorate the toxicity and/or to prevent, delay, or attenuate the development of or risk for developing a toxicity, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of toxicity or symptoms associated with toxicity occurs and/or the risk for developing the toxicity has passed. However, other dosage regimens may be useful and can be determined. The desired dosage can be delivered by a single bolus administration of the composition, by multiple bolus administrations of the composition, or by continuous infusion administration of the composition.

The agents can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the agent. In some embodiments, it is administered by multiple bolus administrations of the agent.

For the amelioration of a toxicity and/or to delay, attenuate to prevent the risk of a toxicity, the appropriate dosage may depend on the type of toxicity to be treated, the type of agent or agents, the type of cells or recombinant receptors previously administered to the subject, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. When administering a therapeutic composition (e.g., a pharmaceutical composition containing an agent that treats or ameliorates symptoms of a toxicity, such as CRS or neurotoxicity), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent is administered parenterally. In some embodiments, the agent is administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the agent in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

In some embodiments, the toxicity-targeting agents are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. In some embodiments, unit dosage forms, include, but are not limited to, tablets, capsules, pills, powders, granules, sterile parenteral solutions or suspensions, and oral solutions or suspensions, and oil water emulsions containing suitable quantities of the compounds or pharmaceutically acceptable derivatives thereof. Unit dose forms can be contained ampoules and syringes or individually packaged tablets or capsules. Unit dose forms can be administered in fractions or multiples thereof. In some embodiments, a multiple dose form is a plurality of identical unit dosage forms packaged in a single container to be administered in segregated unit dose form. Examples of multiple dose forms include vials, bottles of tablets or capsules or bottles of pints or gallons.

III. EXEMPLARY EMBODIMENTS

Among the provided embodiments are:
1. A method of treatment, comprising administering to a subject an agent or other treatment capable of treating, preventing, delaying, or attenuating the development of a toxicity, wherein, at the time of said administration, the subject has been previously administered a therapy, which therapy comprises an immunotherapy and/or a cell therapy, and wherein: (a) the administration of the agent or other treatment is: (i) at a time that is less than or no more than ten, seven, six, five, four or three days after initiation of the administration of the therapy; and/or (ii) at a time at which the subject does not exhibit a sign or symptom of severe cytokine release syndrome (CRS) and/or does not exhibit grade 2 or higher CRS; and/or (iii) at a time at which the subject does not exhibit a sign or symptom of severe neurotoxicity and/or does not exhibit grade 2 or higher neurotoxicity; and/or (b) between the time of the initiation of the administration of the therapy and the time of the administration of the agent or other treatment, (i) the subject has not exhibited severe CRS and/or has not exhibited grade 2 or higher CRS and/or (ii) the subject has not exhibited severe neurotoxicity and/or does not exhibit grade 2 or higher neurotoxicity.
2. A method of treatment, comprising: (a) administering to a subject having a disease or condition a therapy, which therapy comprises an immunotherapy or a cell therapy; and (b) administering to the subject an agent or other treatment capable of treating, preventing, delaying, or attenuating the development of a toxicity, wherein: (i) the administration of the agent or other treatment is at a time that is less than or no more than ten, seven, six, five, four or three days after initiation of the administration of the therapy; and/or (ii) the administration of the agent or other treatment is at a time at which the subject does not exhibit a sign or symptom of severe cytokine release syndrome (CRS) and/or does not exhibit grade 2 or higher CRS; and/or (iii) between the time of the initiation of the administration of the therapy and the time of the administration of the agent or other treatment, the subject has not exhibited severe CRS and/or has not exhibited grade 2 or higher CRS; and/or (iv) the administration of the agent or other treatment is at a time at which the subject does not exhibit a sign or symptom of severe neurotoxicity and/or does not exhibit grade 2 or higher neurotoxicity; and/or (v) between the time of the initiation of the administration of the therapy and the time of the administration of the agent or other treatment, the subject has not exhibited severe neurotoxicity and/or has not exhibited grade 2 or higher neurotoxicity.
3. The method of embodiment 1 or embodiment 2, wherein the agent or other treatment is administered at a time at which the subject exhibits a sign or symptom of CRS and/or exhibits grade 1 CRS or is administered within 24 hours after the subject exhibits a first sign or symptom of grade 1 CRS following the initiation of administration of the therapy.
4. The method of any of embodiments 1-3, wherein: the sign or symptom of grade 1 CRS is a fever; and/or the agent or other treatment is administered within 24 hours after the first sign of a fever following initiation of administration of the therapy.
5. A method of treatment, comprising administering to a subject previously administered with a therapy, which therapy comprises immunotherapy and/or a cell therapy, an agent or other treatment capable of treating, preventing, delaying, or attenuating the development of a toxicity, wherein the agent or other treatment is administered within 24 hours of the first sign of a fever following initiation of administration of the therapy.

6. The method of embodiment 1 or embodiment 5, further comprising, prior to administering the agent or other treatment, administering to the subject the therapy for treating a disease or condition.

7. A method of treatment, comprising: (a) administering to a subject having a disease or condition a therapy, which therapy comprises immunotherapy and/or a cell therapy; and (b) administering to the subject an agent or other treatment capable of treating, preventing, delaying, or attenuating the development of a toxicity at a time within 24 hours after the first sign of fever following initiation of administration of the therapy.

8. The method of any of embodiment 1-7, wherein the agent or other treatment is administered within about 16 hours, within about 12 hours, within about 8 hours, within about 2 hours or within about 1 hour after the first sign of a fever following initiation of administration of the therapy.

9. The method of any of embodiments 4-8, wherein the fever is a sustained fever.

10. The method of any of embodiments 4-9, wherein the fever is a fever that is not reduced or not reduced by more than 1° C. after treatment with an antipyretic and/or wherein the fever has not been reduced by more than 1° C., following treatment of the subject with an antipyretic.

11. The method of any of embodiments 4-10, wherein the fever comprises a temperature of at least or at least about 38.0° C.

12. The method of any of embodiments 4-11, wherein: the fever comprises a temperature that is between or between about 38.0° C. and 42.0° C., 38.0° C. and 39.0° C., 39.0° C. and 40.0° C. or 40.0° C. and 42.0° C., each inclusive; or the fever comprises a temperature that is greater than or greater than about or is or is about 38.5° C., 39.0° C., 39.5° C., 40.0° C., 41.0° C., 42.0° C.

13. The method of any of embodiments 1-12, wherein the agent or other treatment is administered less than five days after initiation of administration of the therapy, less than four days after initiation of administration of the therapy or less than three days after initiation of administration of the therapy.

14. The method of any of embodiments 1-13, wherein the therapy is or comprises a cell therapy.

15. The method of embodiment 14, wherein the cell therapy is or comprises an adoptive cell therapy.

16. The method of any of embodiments 1-15, wherein the therapy is or comprises a tumor infiltrating lymphocytic (TIL) therapy, a transgenic TCR therapy or a recombinant-receptor expressing cell therapy, which optionally is a T cell therapy, which optionally is a chimeric antigen receptor (CAR)-expressing cell therapy.

17. The method of any of embodiments 1-16, wherein the agent or other treatment is or comprises a steroid, or an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta.

18. The method of embodiment 17, wherein the antagonist or inhibitor is or comprises an agent selected from among an antibody or antigen-binding fragment, a small molecule, a protein or peptide and a nucleic acid.

19. The method of embodiment 17 or embodiment 18, wherein the agent or other treatment is or comprises an agent selected from among tocilizumab, situximab, sarilumab, olokizumab (CDP6038), elsilimomab, ALD518/BMS-945429, sirukumab (CNTO 136), CPSI-2634, ARGX-109, FE301 and FM101.

20. The method of any of embodiments 1-19, wherein the agent or other treatment is or comprises tocilizumab.

21. The method of embodiment 20, wherein the tocilizumab is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the tocilizumab is administered in a dosage amount of at least or at least about or about 2 mg/kg, 4 mg/kg, 6 mg/kg or 8 mg/kg.

22. The method of any of embodiment 1-21, further comprising administering a second agent, which optionally is a steroid, to the subject, wherein the steroid is administered: (i) at a time that is within 7 days, 8 days or 9 days after initiation of administration of the therapy, (ii) at a time that is within 24 hours after the first sign of hypotension following initiation of administration of the therapy; (iii) at a time at which the subject exhibits grade 2 cytokine release syndrome (CRS) or within 24 hours after the subject exhibits a first sign of grade 2 CRS following initiation of administration of the therapy; and/or (iv) at a time at which the subject exhibits grade 2 neurotoxicity or within 24 hours after the subject exhibits a first sign or symptom of grade 2 neurotoxicity following initiation of administration of the therapy.

23. A method of treatment, comprising administering a steroid to a subject administered with a therapy, which therapy comprises an immunotherapy and/or a cell therapy, wherein the administration of the steroid is initiated: (i) at a time that is within 7 days, 8 days or 9 days after initiation of administration of the therapy, (ii) at a time that is within 24 hours after the first sign of hypotension following initiation of administration of the therapy; (iii) at a time in which the subject exhibits grade 2 cytokine release syndrome (CRS) or within 24 hours after the subject exhibits a first sign of grade 2 CRS following initiation of administration of the therapy; and/or (iv) at a time in which the subject exhibits grade 2 neurotoxicity or within 24 hours after the subject exhibits a first sign or symptom of grade 2 neurotoxicity following initiation of administration of the therapy.

24. The method of embodiment 23, wherein prior to administering the steroid, the method comprises administering to the subject the therapy for treating a disease or condition.

25. A method of treatment, comprising: (a) administering to a subject having a disease or condition a therapy, which therapy comprises an immunotherapy and/or a cell therapy; and (b) administering to the subject a steroid, wherein the administration of the steroid is initiated: (i) at a time that is within 7 days, 8 days or 9 days after initiation of administration of the therapy, (ii) at a time that is within 24 hours after the first sign of hypotension following initiation of administration of the therapy; (iii) at a time in which the subject exhibits grade 2 cytokine release syndrome (CRS) or within 24 hours after the subject exhibits a first sign of grade 2 CRS following initiation of administration of the therapy; and/or (iv) at a time in which the subject exhibits grade 2 neurotoxicity or within 24 hours after the subject exhibits a first sign or symptom of grade 2 neurotoxicity following initiation of administration of the therapy.

26. The method of treatment of any of embodiments 22-25, wherein, at the time of administration of the steroid, the subject does not exhibit severe CRS, does not exhibit grade 3 or higher CRS, or does not exhibit severe neurotoxicity or does not exhibit grade 3 or higher neurotoxicity.
27. The method of any of embodiments 22-26, wherein the steroid is administered within 24 hours after or contemporaneously with the first sign of hypotension following initiation of administration of the therapy.
28. The method of any of embodiments 22-27, wherein the steroid is administered simultaneously with initiation of a pressor therapy.
29. The method of any of embodiments 22-28, wherein hypotension comprises: systolic blood pressure less than or about less than 90 mm Hg, 80 mm Hg, or 70 mm Hg; or diastolic blood pressure less than 60 mm Hg, 50 mm Hg or 40 mm Hg.
30. The method of any of embodiments 1-17 and 22-29, wherein the agent is or comprises a steroid that optionally is or comprises a corticosteroid, which optionally is a glucocorticoid.
31. The method of embodiment 30, wherein the corticosteroid is or comprises dexamethasone or prednisone.
32. The method of any of embodiments 17 or 22-31, wherein the steroid is administered in an equivalent dosage amount of from or from about 1.0 mg to 20 mg dexamethasone per day, 1.0 mg to 10 mg dexamethasone per day, or 2.0 mg to 6.0 mg dexamethasone per day, each inclusive.
33. The method of any of embodiments 17 or 22-32, wherein the steroid is administered intravenously or orally.
34. The method of any of embodiments 23-33, wherein prior to administering the steroid, the method comprises administering an agent or other treatment capable of treating, preventing, delaying, or attenuating the development of a toxicity associated, wherein: (i) the agent or other treatment is administered at a time that is less than or no more than ten, seven, six, five, four or three days after initiation of the administration of the therapy; and/or (ii) the agent or other treatment is administered at a time at which the subject does not exhibit a sign or symptom of severe cytokine release syndrome (CRS) and/or does not exhibit grade 2 or higher CRS; and/or (iii) between the time of the initiation of the administration of the therapy and the time of the administration of the agent or other treatment, the subject has not exhibited severe CRS and/or has not exhibited grade 2 or higher CRS; and/or (iv) the agent or other treatment is administered at a time at which the subject does not exhibit a sign or symptom of severe neurotoxicity and/or does not exhibit grade 2 or higher neurotoxicity; and/or (v) between the time of the initiation of the administration of the therapy and the time of the administration of the agent or other treatment, the subject has not exhibited severe neurotoxicity and/or has not exhibited grade 2 or higher CRS.
35. The method of embodiment 34, wherein the agent or other treatment is administered at a time at which the subject exhibits grade 1 CRS or is administered within 24 hours after the subject exhibits a first sign or symptom of grade 1 CRS.
36. The method of embodiment 34 or embodiment 35, wherein: the first sign or symptom of grade 1 CRS is a fever; or the agent or other treatment is administered within 24 hours after the first sign of fever following initiation of administration of the therapy.
37. The method of any of embodiments 23-36, further comprising, prior to administering the steroid, administering an agent or other treatment capable of treating, preventing, delaying, or attenuating the development of a toxicity, wherein the agent or other treatment is administered within 24 hours after the first sign of fever following initiation of administration of the therapy.
38. The method of embodiment 36 or embodiment 37, wherein the agent or other treatment is administered within about 16 hours, within about 12 hours, within about 8 hours, within about 2 hours or within about 1 hour after the first sign of fever following initiation of administration of the therapy.
39. The method of any of embodiments 36-38, wherein the fever is a sustained fever.
40. The method of any of embodiments 36-39, wherein the fever is a fever that is not reduced or not reduced by more than 1° C. after treatment with an antipyretic and/or wherein the fever has not been reduced by more than 1° C., following treatment of the subject with an antipyretic.
41. The method of any of embodiments 36-40, wherein the fever comprises a temperature of at least or at least about 38.0° C.
42. The method of any of embodiments 36-41, wherein: the fever comprises a temperature that is between or between about 38.0° C. and 42.0° C., 38.0° C. and 39.0° C., 39.0° C. and 40.0° C. or 40.0° C. and 42.0° C., each inclusive; or the fever comprises a temperature that is greater than or greater than about or is or is about 38.5° C., 39.0° C., 39.5° C., 40.0° C., 41.0° C., 42.0° C.
43. The method of any of embodiments 34-42, wherein the agent or other treatment is administered less than five days after initiation of administration of the therapy, less than four days after initiation of administration of the therapy or less than three days after initiation of administration of the therapy.
44. The method of any of embodiments 23-43, wherein the therapy is a cell therapy.
45. The method of embodiment 44, wherein the cell therapy is an adoptive cell therapy.
46. The method of any of embodiments 23-45, wherein the therapy is a tumor infiltrating lymphocytic (TIL) therapy, a transgenic TCR therapy or a recombinant-receptor expressing cell therapy, which optionally is a T cell therapy, which optionally is a chimeric antigen receptor (CAR)-expressing cell therapy.
47. The method of any of embodiments 34-46, wherein the agent or other treatment is an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta.
48. The method of embodiment 47, wherein the antagonist or inhibitor is or comprises an agent selected from among an antibody or antigen-binding fragment, a small molecule, a protein, a peptide and a nucleic acid.
49. The method of embodiment 47 or embodiment 48, wherein the agent or other treatment is or comprises an agent selected from among tocilizumab, situximab, sarilumab, olokizumab (CDP6038), elsilimomab, ALD518/BMS-945429, sirukumab (CNTO 136), CPSI-2634, ARGX-109, FE301 and FM101.

50. The method of any of embodiments 34-49, wherein the agent or other treatment is or comprises tocilizumab.
51. The method of embodiment 50, wherein the tocilizumab is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the tocilizumab is administered in a dosage amount of at least or at least about or about 2 mg/kg, 4 mg/kg, 6 mg/kg or 8 mg/kg.
52. The method of any of embodiments 1-51, wherein the therapy is or comprises a cell therapy and the number of cells administered is between about $0.25 \times 10^6$ cells/kg body weight of the subject and $5 \times 10^6$ cells/kg, $0.5 \times 10^6$ cells/kg body weight of the subject and $3 \times 10^6$ cells/kg, between about $0.75 \times 10^6$ cells/kg and $2.5 \times 10^6$ cells/kg or between about $1 \times 10^6$ cells/kg and $2 \times 10^6$ cells/kg, each inclusive.
53. The method of any of embodiments 1-52, wherein the therapy is or comprises a cell therapy and the cells are administered in a single pharmaceutical composition comprising the cells.
54. The method of any of embodiments 1-52, wherein the therapy is or comprises a cell therapy and the dose of cells is a split dose, wherein the cells of the dose are administered in a plurality of compositions, collectively comprising the cells of the dose, over a period of no more than three days.
55. The method of any of embodiments 1-54, wherein the disease or condition is a tumor or a cancer.
56. The method of any of embodiments 1-55, wherein the disease or condition is a leukemia or lymphoma.
57. The method of any of embodiments 1-56, wherein the disease or condition is a non-Hodgkin lymphoma (NHL) or acute lymphoblastic leukemia (ALL).
58. The method of any of embodiments 1-57, wherein the therapy is a cell therapy comprising a dose of cells expressing a recombinant receptor, wherein: the recombinant receptor binds to, recognizes or targets an antigen associated with the disease or condition; and/or the recombinant receptor is a T cell receptor or a functional non-T cell receptor; and/or the recombinant receptor is a chimeric antigen receptor (CAR).
59. The method of embodiment 58, wherein the CAR comprises an extracellular antigen-recognition domain that specifically binds to the antigen and an intracellular signaling domain comprising an ITAM.
60. The method of embodiment 59, wherein the antigen is CD19.
61. The method of embodiment 60, wherein the intracellular signaling domain comprises an intracellular domain of a CD3-zeta (CD3ζ) chain.
62. The method of embodiment 60 or embodiment 61, wherein the CAR further comprises a costimulatory signaling region.
63. The method of embodiment 62, wherein the costimulatory signaling domain comprises a signaling domain of CD28 or 4-1BB.
64. The method of any of any of embodiments 1-63, wherein the therapy is a cell therapy comprising a dose of cells comprising T cells.
65. The method of embodiment 64, wherein the T cells are CD4+ or CD8+.
66. The method of any of embodiment 64 or embodiment 65, wherein the T cells are autologous to the subject.
67. The method of any of embodiments 1-66, wherein the method further comprises administering a chemotherapeutic agent prior to administering the therapy and/or wherein the subject has been previously treated with a chemotherapeutic agent prior to the initiation of administration of the therapy.
68. The method of embodiment 67, wherein the chemotherapeutic agent comprises an agent selected from the group consisting of cyclophosphamide, fludarabine, and/or a combination thereof.
69. The method of embodiment 67 or embodiment 68, wherein the chemotherapeutic agent is administered between 2 and 5 days prior to the initiation of administration of the therapy.
70. The method of any of embodiments 67-69, wherein: the chemotherapeutic agent is fludarabine that is administered at a dose of between or between about 1 $mg/m^2$ and 100 $mg/m^2$, between or between about 10 $mg/m^2$ and 75 $mg/m^2$, between or between about 15 $mg/m^2$ and 50 $mg/m^2$, between or between about 20 $mg/m^2$ and 30 $mg/m^2$, or between or between about 24 $mg/m^2$ and 26 $mg/m^2$; and/or the chemotherapeutic agent is cyclophosphamide that is administered between or between about 20 mg/kg and 100 mg/kg, between or between about 40 mg/kg and 80 mg/kg or between or between about 30 mg/kg and 60 mg/kg.
71. The method of any of embodiments 1-70, wherein a toxic outcome in the subject at day up to or up to about day 7, 8, 9, 10, 11, 12, 13, 14, 15, 16, 17, 18, 19, 20, 21, 22, 23, 24, 25, 26, 27, 28, 29 or 30 following administration of the therapy is not detectable or is reduced as compared to a method comprising an alternative treatment regimen wherein the subject is administered the agent or other treatment after severe CRS has developed or after grade 2 or higher CRS has developed.
72. The method of embodiment 71, wherein the toxic outcome is reduced by greater than 50%, 60%, 70%, 80%, 90% or more.
73. The method of embodiment 71 or embodiment 72, wherein the toxic outcome is a symptom associated with grade 3 or higher neurotoxicity or is a symptom associated with grade 2 or higher CRS.
74. The method of any of embodiments 71-73, wherein the toxic outcome is grade 3 or higher neurotoxicity comprising one or more symptom selected from among confusion, delirium, expressive aphasia, obtundation, myoclonus, lethargy, altered mental status, convulsions, seizure-like activity and seizures.
75. The method of any of embodiments 71-73, wherein the toxic outcome is grade 3 or higher CRS comprising one or more symptom selected from among persistent fever greater than at or about 38 degrees Celsius, for at least three consecutive days; hypotension requiring high dose vasopressor or multiple vasopressors; hypoxia, which optionally comprises plasma oxygen ($PO_2$) levels of less than at or about 90% and respiratory failure requiring mechanical ventilation.
76. The method of any of embodiment 1-75, wherein the therapy is a cell therapy comprising a dosage of cells and the cells exhibit increased or prolonged expansion and/or persistence in the subject as compared to administration of the cell therapy in the subject or in a corresponding subject in an alternative cohort or treatment group using alternative treatment regimen, wherein said alternative treatment regimen comprises administering the cell therapy and subsequently administering the agent or other treatment after severe CRS has developed or after grade 2 or higher CRS has developed, and optionally wherein the subject in said alternative treatment regimen is not administered said agent, and optionally is not administered any other treatment designed to treat CRS or neurotoxicity, following the administration of the cells and prior to said development of grade 2 or higher CRS or severe CRS.

77. The method of embodiment 76, wherein the increase in or prolonging of expansion and/or persistence is by 2-fold, 3-fold, 4-fold, 5-fold, 6-fold, 7-fold, 8-fold, 9-fold or 10-fold.

78. The method of any of embodiments 1-77, wherein: the therapy is a cell therapy, comprising engineered and/or CAR-expressing cells; and the concentration or number of the engineered and/or CAR-expressing cells in the blood of the subject at day 30, day 60, or day 90 following initiation of administration of the therapy is at least at or about 10 engineered or CAR-expressing cells per microliter, at least 50% of the total number of peripheral blood mononuclear cells (PBMCs), at least or at least about $1\times10^5$ engineered or CAR-expressing cells, and/or at least 5,000 copies of CAR-encoding or engineered receptor-encoding DNA per micrograms DNA; and/or; at day 30, 60, or 90 following the initiation of the administration of the therapy, the CAR-expressing and/or engineered cells are detectable in the blood or serum of the subject; and/or at day 30, 60, or 90 following the initiation of the administration of the therapy, the blood of the subject contains at least 20% CAR-expressing cells, at least 10 CAR-expressing cells per microliter or at least $1\times10^4$ CAR-expressing cells; at day 30, 60, or 90 following the initiation of the administration of the therapy, the blood of the subject contains at least 50%, 60%, 70%, 80%, or 90% of a biologically effective dose of the cells; at day 30, 60, or 90 following the initiation of the administration of the therapy, the blood of the subject contains at least 20% engineered and/or CAR-expressing cells, at least 10 engineered and/or CAR-expressing cells per microliter and/or at least $1\times10^4$ engineered and/or CAR-expressing cells; at day 30, 60, or 90 following the initiation of the administration of the therapy, the subject exhibits a reduction or sustained reduction in burden of the disease or condition, that is at or about or at least at or about 50, 60, 70, or 80% peak reduction following the therapy administration or reduction associated with effective dose.

79. The method of any of embodiments 1-78, wherein: at day 30, 60 or 90 following the initiation of the administration of the therapy, the subject does not, and/or has not exhibited severe neurotoxicity, severe CRS, grade 2 or higher CRS, grade 2 or higher neurotoxicity, and/or has not exhibited seizures or other CNS outcome; or at day 30, 60, or 90 following the initiation of the administration of the therapy, less than or about less than 25%, less than or about less than 20%, less than or about less than 15%, or less than or about less than 10% of the subjects so treated do not, and/or have not exhibited severe neurotoxicity, severe CRS, grade 2 or higher CRS, grade 2 or higher neurotoxicity, and/or have not exhibited seizures or other CNS outcome.

80. The method of any of embodiments 1-79, wherein the therapy is a cell therapy, comprising engineered and/or CAR-expressing cells; and the area under the curve (AUC) for blood concentration of engineered and/or CAR-expressing cells over time following the administration of the therapy is greater as compared to that achieved via a method comprising an alternative dosing regimen wherein the subject is administered the therapy and is administered the agent or other treatment at a time at which the subject exhibits a severe or grade 2 or higher or grade 3 or higher CRS or neurotoxicity.

81. An agent or other treatment for use in the treatment, prevention, delay or attenuation of the development of a toxicity in a subject that has been previously administered a therapy, which therapy comprises an immunotherapy and/or a cell therapy, wherein: (a) the agent or other treatment is administered to a subject: (i) at a time that is less than or no more than ten, seven, six, five, four or three days after initiation of the subject having been administered the therapy; and/or (ii) at a time at which the subject does not exhibit a sign or symptom of severe cytokine release syndrome (CRS) and/or does not exhibit grade 2 or higher CRS; and/or (iii) at a time at which the subject does not exhibit a sign or symptom of severe neurotoxicity and/or does not exhibit grade 2 or higher neurotoxicity; and/or (b) between the time of initiation of the subject having been administered the therapy and the time of the administration of the agent or other treatment, (i) the subject has not exhibited severe CRS and/or has not exhibited grade 2 or higher CRS and/or (ii) the subject has not exhibited severe neurotoxicity and/or does not exhibit grade 2 or higher neurotoxicity.

82. The agent or other treatment of embodiment 81, wherein the agent or other treatment is administered at a time at which the subject exhibits a sign or symptom of CRS and/or exhibits grade 1 CRS or is administered within 24 hours after the subject exhibits a first sign or symptom of grade 1 CRS following the administration of the therapy.

83. The agent or other treatment of embodiment 81 or embodiment 82, wherein: the sign or symptom of grade 1 CRS is a fever; and/or the agent or other treatment is administered within 24 hours after the first sign of a fever following administration of the therapy.

84. An agent or other treatment for use in the treatment, prevention, delay or attenuation of the development of a toxicity in a subject that has been previously administered a therapy, which therapy comprises an immunotherapy and/or a cell therapy, wherein the agent or other treatment is administered within 24 hours of the first sign of a fever following administration of the therapy.

85. An agent or other treatment for use as a medicament in treating, preventing, delaying, or attenuating the development of a toxicity in a subject that has been previously administered a therapy, which therapy comprises an immunotherapy and/or a cell therapy, wherein: (a) the agent or other treatment is administered to a subject: (i) at a time that is less than or no more than ten, seven, six, five, four or three days after initiation of the subject having been administered the therapy; and/or (ii) at a time at which the subject does not exhibit a sign or symptom of severe cytokine release syndrome (CRS) and/or does not exhibit grade 2 or higher CRS; and/or (iii) at a time at which the subject does not exhibit a sign or symptom of severe neurotoxicity and/or does not exhibit grade 2 or higher neurotoxicity; and/or (b) between the time of initiation of the subject having been administered the therapy and the time of the administration of the agent or other treatment, (i) the subject has not exhibited severe CRS and/or has not exhibited grade 2 or higher CRS and/or (ii) the subject has not exhibited severe neurotoxicity and/or does not exhibit grade 2 or higher neurotoxicity.

86. The agent or other treatment of embodiment 85, wherein the agent or other treatment is administered at a time at which the subject exhibits a sign or symptom of CRS and/or exhibits grade 1 CRS or is administered within 24 hours after the subject exhibits a first sign or symptom of grade 1 CRS following the administration of the therapy.
87. The agent or other treatment of embodiment 85 or embodiment 86, wherein: the sign or symptom of grade 1 CRS is a fever; and/or the agent or other treatment is administered within 24 hours after the first sign of a fever following administration of the therapy.
88. An agent or other treatment for use as a medicament in treating, preventing, delaying, or attenuating the development of a toxicity in a subject that has been previously administered a therapy, which therapy comprises an immunotherapy and/or a cell therapy, wherein the agent or other treatment is administered within 24 hours of the first sign of a fever following administration of the therapy.
89. Use of an agent or other treatment for the manufacture of a medicament for treating, preventing, delaying, or attenuating the development of a toxicity in a subject that has been previously administered a therapy, which therapy comprises an immunotherapy and/or a cell therapy, wherein: (a) the agent or other treatment is administered to a subject: (i) at a time that is less than or no more than ten, seven, six, five, four or three days after initiation of the subject having been administered the therapy; and/or (ii) at a time at which the subject does not exhibit a sign or symptom of severe cytokine release syndrome (CRS) and/or does not exhibit grade 2 or higher CRS; and/or (iii) at a time at which the subject does not exhibit a sign or symptom of severe neurotoxicity and/or does not exhibit grade 2 or higher neurotoxicity; and/or (b) between the time of initiation of the subject having been administered the therapy and the time of the administration of the agent or other treatment, (i) the subject has not exhibited severe CRS and/or has not exhibited grade 2 or higher CRS and/or (ii) the subject has not exhibited severe neurotoxicity and/or does not exhibit grade 2 or higher neurotoxicity.
90. The use of embodiment 89, wherein the agent or other treatment is administered at a time at which the subject exhibits a sign or symptom of CRS and/or exhibits grade 1 CRS or is administered within 24 hours after the subject exhibits a first sign or symptom of grade 1 CRS following the administration of the therapy.
91. The use of embodiment 89 or embodiment 90, wherein: the sign or symptom of grade 1 CRS is a fever; and/or the agent or other treatment is administered within 24 hours after the first sign of a fever following administration of the therapy.
92. Use of an agent or other treatment for the manufacture of a medicament for treating, preventing, delaying, or attenuating the development of a toxicity in a subject that has been previously administered a therapy, which therapy comprises an immunotherapy and/or a cell therapy, wherein the agent or other treatment is administered within 24 hours of the first sign of a fever following administration of the therapy.
93. The agent or other treatment of any of embodiments 81-88 or the use of any of embodiments 89-92, wherein the agent or other treatment is administered within about 16 hours, within about 12 hours, within about 8 hours, within about 2 hours or within about 1 hour after the first sign of a fever following administration of the therapy.
94. The agent or other treatment or use of any of embodiments 83, 84, 87, 88 and 91-93, wherein the fever is a sustained fever.
95. The agent or other treatment or use of any of embodiments 83, 84, 87, 88 and 91-94, wherein the fever is a fever that is not reduced or not reduced by more than 1° C. after treatment with an antipyretic and/or wherein the fever has not been reduced by more than 1° C., following treatment of the subject with an antipyretic.
96. The agent or other treatment or use of any of embodiments 83, 84, 87, 88 and 91-95, wherein the fever comprises a temperature of at least or at least about 38.0° C.
97. The agent or other treatment or use of any of embodiments 83, 84, 87, 88 and 91-96, wherein: the fever comprises a temperature that is between or between about 38.0° C. and 42.0° C., 38.0° C. and 39.0° C., 39.0° C. and 40.0° C. or 40.0° C. and 42.0° C., each inclusive; or the fever comprises a temperature that is greater than or greater than about or is or is about 38.5° C., 39.0° C., 39.5° C., 40.0° C., 41.0° C., 42.0° C.
98. The agent or other treatment or use of any of embodiments 81-97, wherein the agent or other treatment is or comprises a steroid, or an antagonist or inhibitor of a cytokine receptor or cytokine selected from among IL-10, IL-10R, IL-6, IL-6 receptor, IFNγ, IFNGR, IL-2, IL-2R/CD25, MCP-1, CCR2, CCR4, MIP1β, CCR5, TNFalpha, TNFR1, IL-1, and IL-1Ralpha/IL-1beta.
99. The agent or other treatment or use of embodiment 98, wherein the antagonist or inhibitor is or comprises an agent selected from among an antibody or antigen-binding fragment, a small molecule, a protein or peptide and a nucleic acid.
100. The agent or other treatment or use of embodiment 98 or embodiment 99, wherein the agent or other treatment is or comprises an agent selected from among tocilizumab, situximab, sarilumab, olokizumab (CDP6038), elsilimomab, ALD518/BMS-945429, sirukumab (CNTO 136), CPSI-2634, ARGX-109, FE301 and FM101.
101. The agent or other treatment or use of any of embodiments 81-100, wherein the agent or other treatment is or comprises tocilizumab.
102. The agent or other treatment or use of embodiment 101, wherein the tocilizumab is for administration in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the tocilizumab is administered in a dosage amount of at least or at least about or about 2 mg/kg, 4 mg/kg, 6 mg/kg or 8 mg/kg.
103. The agent or other treatment or use of any of embodiments 81-98, wherein the agent is or comprises a steroid that optionally is or comprises a corticosteroid, which optionally is a glucocorticoid.
104. The agent or other treatment or use of embodiment 103, wherein the corticosteroid is or comprises dexamethasone or prednisone.
105. The agent or other treatment or use of any of embodiments 81-98, 103 and 104, wherein the steroid is for administration in an equivalent dosage amount of from or from about 1.0 mg to 20 mg dexamethasone per day, 1.0 mg to 10 mg dexamethasone per day, or 2.0 mg to 6.0 mg dexamethasone per day, each inclusive.
106. The agent or other treatment or use of any of embodiments 81-98 and 103-105, wherein the steroid is formulated for intravenous or oral administration.
107. The agent or other treatment or use of any of embodiments 81-106, wherein the therapy is or comprises a cell therapy.
108. The agent or other treatment or use of embodiment 107, wherein the cell therapy is or comprises an adoptive cell therapy.
109. The agent or other treatment or use of any of embodiments 81-108, wherein the therapy is or comprises a tumor infiltrating lymphocytic (TIL) therapy, a transgenic TCR therapy or a recombinant-receptor expressing cell therapy, which optionally is a T cell therapy, which optionally is a chimeric antigen receptor (CAR)-expressing cell therapy.
110. The agent or other treatment or use of any of embodiments 81-109, wherein the therapy is a cell therapy comprising a dose of cells expressing a recombinant receptor, wherein: the recombinant receptor binds to, recognizes or targets an antigen associated with a disease or condition; and/or the recombinant receptor is a T cell receptor or a functional non-T cell receptor; and/or the recombinant receptor is a chimeric antigen receptor (CAR).
111. The agent or other treatment or use of embodiment 109 or embodiment 110, wherein the CAR comprises an extracellular antigen-recognition domain that specifically binds to the antigen and an intracellular signaling domain comprising an ITAM.
112. The agent or other treatment or use of embodiment 111, wherein the antigen is CD19.
113. The agent or other treatment or use of embodiment 111, wherein the intracellular signaling domain comprises an intracellular domain of a CD3-zeta (CD3ζ) chain.
114. The agent or other treatment or use of any of embodiments 109-113, wherein the CAR further comprises a costimulatory signaling region.
115. The agent or other treatment or use of embodiment 114, wherein the costimulatory signaling domain comprises a signaling domain of CD28 or 4-1BB.
116. The agent or other treatment or use of any of embodiments 81-115, wherein the therapy is a cell therapy comprising a dose of cells comprising T cells.
117. The agent or other treatment or use of embodiment 116, wherein the T cells are CD4+ or CD8+.
118. The agent or other treatment or use of embodiment 116 or embodiment 117, wherein the T cells are autologous to the subject.
119. The agent or other treatment or use of any of embodiments 110-118, wherein the disease or condition is a tumor or a cancer.
120. The agent or other treatment or use of any of embodiments 110-119, wherein the disease or condition is a leukemia or lymphoma.
121. The agent or other treatment or use of any of embodiments 110-120, wherein the disease or condition is a non-Hodgkin lymphoma (NHL) or acute lymphoblastic leukemia (ALL).
122. The agent or other treatment or use of any of embodiments 81-121, wherein the subject has been previously treated with a chemotherapeutic agent prior to the administration of the therapy.
123. The agent or other treatment or use of embodiment 122, wherein the chemotherapeutic agent comprises an agent selected from the group consisting of cyclophosphamide, fludarabine, and/or a combination thereof.

IV. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, a "subject" is a mammal, such as a human or other animal, and typically is human. In some embodiments, the subject, e.g., patient, to whom the agent or agents, cells, cell populations, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided agents, cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, agent, cells, or composition, in the context of administration, refers to an amount effective, at dosages/amounts and for periods of time necessary, to achieve a desired result, such as a therapeutic or prophylactic result.

A "therapeutically effective amount" of an composition, e.g., a pharmaceutical formulation comprising agents or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the agents or populations of cells administered. In some embodiments, the provided methods involve administering the agents, cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

V. Examples

The following examples are included for illustrative purposes only and are not intended to limit the scope of the invention.

Example 1 Early Intervention Method for Preventing or Reducing Toxicity in Cancer Patients Treated with CAR-Expressing Autologous T Cells A cohort of subjects (n=6) with pediatric acute lymphoblastic leukemia (ALL) were administered autologous T cells expressing an anti-CD19 chimeric antigen receptor (CAR). The construct encoding the CAR also included a nucleic acid encoding truncated EGFR (EGFRt), for use as a marker. Prior to administration of the cells, patients underwent leukapheresis and were treated with a conditioning chemotherapy regimen including fludarabine and cyclophosphamide. To generate the autologous CAR-expressing T cells, T cells were isolated by immunoaffinity-based enrichment from leukapheresis samples from individual subjects, activated and transduced with a viral vector encoding an anti-CD19 CAR, followed by expansion.

Prior to administration of the CAR-expressing T cells, subjects were treated either with 30 mg/m$^2$ fludarabine daily for 3 days and 300 mg/m$^2$ cyclophosphamide daily for 3 days. At d=0, subjects were then treated with 0.5-10×10$^6$ cells/kg of CAR-expressing T cells.

As an early or preemptive treatment to prevent or ameliorate potential toxicities, subjects were administered agents capable of treating or preventing such toxicities, at a time point prior to the emergence of severe toxicity and/or prior to signs or symptoms of neurotoxicity. At the first sign of sustained fever following administration of the CAR-expressing T cells (e.g. a fever that did not subside upon administration of an anti-pyretic), subjects were treated with the anti-IL-6 receptor antibody tocilizumab at either 4 mg/kg or 8 mg/kg. In subjects exhibiting hypotension, such as hypotension to a degree indicating the subject should be treated with low-dose pressor therapy, subjects were administered the steroid dexamethasone, beginning at the time of such hypotension, such as at the time of administration of such pressor therapy. If applicable, such subjects were administered dexamethasone at 5-10 mg/day for two days.

At various time-points relative to treatment, tumor burden was assessed in the subjects. At day 63+, each of the subjects in this cohort exhibited minimal residual disease (MRD)-negative Complete remission (CR), with CAR-T persistence of greater than 80% biologically effective dose (BED), as measured by level of B cell aplasia (BCA).

One of the six subjects in this cohort developed hypotension requiring pressor therapy, and none (0/6) of the subjects developed signs or symptoms of severe neurotoxicity (CNS-outcome) or exhibited seizures. The results demonstrate the successful preemptive intervention with toxicity-targeting agent(s) showed that subjects preemptively treated with a regimen involving an early intervention using agents generally used to target outcomes of toxicities observed following CAR-T therapy (prior to the development of severe CRS or neurotoxicity symptoms) exhibited an absence of any CNS outcomes or neurotoxicity and of severe CRS, while also exhibiting persistence and continued efficacy of the CAR-T cells over time.

Example 2 Early Intervention Method for Preventing or Reducing Toxicity in Cancer Patients Treated with CAR-Expressing Autologous T Cells As an extension of the study, cohorts of subjects (total n=43) with pediatric acute lymphoblastic leukemia (ALL) were administered autologous T cells expressing an anti-CD19 chimeric antigen receptor (CAR) as described in Example 1 were assessed.

In this assessment, a subjects in a first cohort (n=20), were administered a treatment for toxicity following evidence or sign, if applicable, of a dose limiting toxicity following the CAR-T cell infusion and (2) subjects in a second cohort (n=23) were administered an early intervening therapy to ameliorate or prevent toxicity or toxic outcome, prior to developing or exhibiting dose-limiting toxicity. Specifically, in the first cohort (n=20), subjects were treated with the anti-IL-6 receptor antibody tocilizumab at 8 mg/kg with or without steroids, in the event of dose limiting toxicity. Subjects in the second cohort (n=23) was administered an early or preemptive treatment of the anti-IL-6 receptor antibody tocilizumab and optionally dexamethasone if, following administration of the CAR-expressing T cells, they exhibited persistent fever of greater than or equal to 39° C., despite antipyretics for 10 hours, persistent or recurrent hypotension after initial fluid bolus, and/or initiation of oxygen supplement. At various time-points relative to treatment, engraftment of CAR T cells and B cell aplasia was determined by flow cytometry and tumor burden was assessed in the subjects. The overall rate of minimal residual disease (MRD)-negative complete remission (CR) was 93% ($^{40}/_{43}$) and was not impacted by the use of tocilizumab or dexamethasone. The rates of MRD-negative CR in patients receiving tocilizumab without steroids, tocilizumab with steroids or steroids alone were similar (89% vs. 100% vs. 100%, respectively). Continued peripheral blood expansion of CAR T cells was seen in subjects that received tocilizumab and/or steroids. The results demonstrate that early intervention treatment with tocilizumab or dexamethasone did not impact the efficacy of the CAR T cell therapy, engraftment of the CAR T cells, or persistence of the CAR T cells. Overall rates of CRS observed in the two cohorts were 91% ($^{21}/_{23}$) and 95% ($^{19}/_{20}$), respectively. Rates of severe CRS were 30% ($^{9}/_{23}$) and 15% ($^{3}/_{20}$), respectively, p=0.3. Results of the early intervention strategy are shown in Table 5, below.

TABLE 5

| Cohort | CR rate | CRS | sCRS | NTox | sNTox | Toci | Steroids | B cell aplasia | 1 year event free survival |
|---|---|---|---|---|---|---|---|---|---|
| Dose limiting toxicity | 91% | 91% | 30% | 48% | 22% | 22% | 17% | 2.1m | 52% |
| Early intervention | 95% | 95% | 15% | 50% | 25% | 50% | 30% | 3.9m | 51% |

Figure 3:
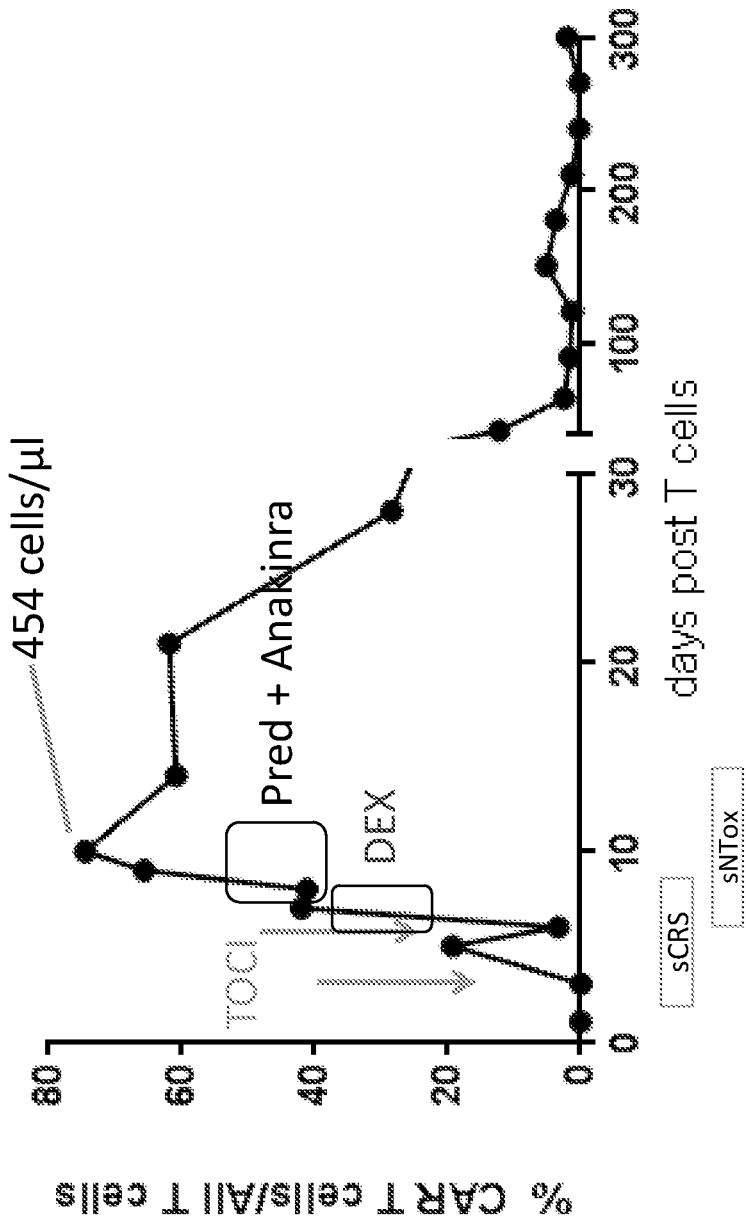
FIG. 3 depicts the percentage of CAR+ T cells among all T cells in the blood of subjects at various days post-infusion of CAR+ T cells after receiving intervention with dexamethasone (Dex), tocilizumab (toci) or prednisone+recombinant IL-1 receptor antagonist anakinra (pred+ anakinra) for treating severe toxicity, was administered. The onset of severe CRS (sCRS) and severe neurotoxicity (sNTox) is depicted. Peak expansion of CAR+ T cells was 454 cells/µL. Expansion was not affected by the administration of intervening therapies.

Cell proliferation was assessed in subjects receiving intervention for severe toxicity. The results show that expansion of CAR T cells was not affected by the administration of tocilizumab, as shown in FIG. 3. The peak number of CAR T-cells per microliter of peripheral blood was significantly higher in patients with severe CRS (FIG. 4A) and severe neurotoxicity (FIG. 4B) than those without (p=0.002 and p=0.0015, respectively). The results show that patients with higher peak CAR T cell numbers may exhibit an increased risk for severe CRS and neurotoxicity.

Various biomarkers were assessed at day 28 in subjects with and without severe CRS for each cohort. FIGS. 2A, 2B, 2C, and 2D show the correlation of peak cytokine levels for IL-6, IFN-γ, Granzyme B, and IL-2, respectively. Some biomarkers exhibited statistically significant differences between subjects within the same cohort with (yes) and without (no) severe CRS.

Table 6 presents data of adverse events for all subjects in both cohorts (N=43) that were possibly, probably, or definitely related to the study.

TABLE 6

| Adverse event | Grade 3 (N = 43) | Grade 4 (N = 43) |
|---|---|---|
| Alanine aminotransferase increased | 3 (7.0%) | 0 (0.0%) |
| Aspartate aminotransferase increased | 1 (2.3%) | 0 (0.0%) |
| Chills | 1 (2.3%) | 0 (0.0%) |
| Cytokine release syndrome | 9 (20.9%) | 9 (20.9%) |
| Febrile neutropenia | 2 (4.7%) | 0 (0.0%) |
| Headache | 1 (2.3%) | 0 (0.0%) |
| Hypotension | 0 (0.0%) | 1 (2.3%) |
| Left ventricular dysfunction | 1 (2.3%) | 0 (0.0%) |

Table 7 presents data of neurotoxicity events for all subjects in both cohorts (N=43) that were possibly, probably, or definitely related to the study.

TABLE 7

| Adverse event | Grade 2 (N = 43) | Grade 3 (N = 43) | Grade 4 (N = 43) |
|---|---|---|---|
| Any AE | 7 (16.3%) | 4 (9.3%) | 4 (9.3%) |
| Encephalopathy | 7 (16.3%) | 6 (14.0%) | 1 (2.3%) |
| Hydrocephalus | 0 (0.0%) | 0 (0.0%) | 1 (2.3%) |
| Seizure | 2 (4.7%) | 2 (4.7%) | 1 (2.3%) |
| Tremor | 1 (2.3%) | 0 (0.0%) | 1 (2.3%) |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
|---|---|---|
| 1 | ESKYGPPCPPCP | spacer (IgG4hinge) (aa) Homo sapiens |
| 2 | GAATCTAAGTACGGACCGCCCTGCCCCCCTTGCCCT | spacer (IgG4hinge) (nt) homo sapiens |
| 3 | ESKYGPPCPPCPGQPREPQVYTLPPSQEEMTKNQVSLTCLVKGFY PSDIAVEWESNGQPENNYKTTPPVLDSDGSFFLYSRLTVDKSRWQ EGNVFSCSVMHEALHNHYTQKSLSLSLGK | Hinge-CH3 spacer Homo sapiens |
| 4 | ESKYGPPCPPCPAPEFLGGPSVFLFPPKPKDTLMISRTPEVTCVVVD VSQEDPEVQFNWYVDGVEVHNAKTKPREEQFNSTYRVVSVLTVL HQDWLNGKEYKCKVSNKGLPSSIEKTISKAKGQPREPQVYTLPPS QEEMTKNQVSLTCLVKGFYPSDIAVEWESNGQPENNYKTTPPVL DSDGSFFLYSRLTVDKSRWQEGNVFSCSVMHEALHNHYTQKSLS LSLGK | Hinge-CH2-CH3 spacer Homo sapiens |
| 5 | RWPESPKAQASSVPTAQPQAEGSLAKATTAPATTRNTGRGGEEK KKEKEKEEQEERETKTPECPSHTQPLGVYLLTPAVQDLWLRDKA TFTCFVVGSDLKDAHLTWEVAGKVPTGGVEEGLLERHSNGSQSQ HSRLTLPRSLWNAGTSVTCTLNHPSLPPQRLMALREPAAQAPVKL SLNLLASSDPPEAASWLLCEVSGFSPPNILLMWLEDQREVNTSGF | IgD-hinge-Fc Homo sapiens |

| SEQ ID NO. | SEQUENCE | DESCRIPTION |
|---|---|---|
|  | APARPPPQPGSTTFWAWSVLRVPAPPSPQPATYTCVVSHEDSRTL LNASRSLEVSYVTDH |  |
| 6 | LEGGGEGRGSLLTCGDVEENPGPR | T2A artificial |
| 7 | MLLLVTSLLLCELPHPAFLLIPRKVCNGIGIGEFKDSLSINATNIKHF KNCTSISGDLHILPVAFRGDSFTHTPPLDPQELDILKTVKEITGFLLI QAWPENRTDLHAFENLEIIRGRTKQHGQFSLAVVSLNITSLGLRSL KEISDGDVIISGNKNLCYANTINWKKLFGTSGQKTKIISNRGENSC KATGQVCHALCSPEGCWGPEPRDCVSCRNVSRGRECVDKCNLLE GEPREFVENSECIQCHPECLPQAMNITCTGRGPDNCIQCAHYIDGP HCVKTCPAGVMGENNTLVWKYADAGHVCHLCHPNCTYGCTGP GLEGCPTNGPKIPSIATGMVGALLLLLVVALGIGLFM | tEGFR artificial |
| 8 | FWVLVVVGGVLACYSLLVTVAFIIFWV | CD28 (amino acids 153-179 of Accession No. P10747) *Homo sapiens* |
| 9 | IEVMYPPPYLDNEKSNGTIIHVKGKHLCPSPLFPGPSKP FWVLVVVGGVLACYSLLVTVAFIIFWV | CD28 (amino acids 114-179 of Accession No. P10747) *Homo sapiens* |
| 10 | RSKRSRLLHSDYMNMTPRRPGPTRKHYQPYAPPRDFAAYRS | CD28 (amino acids 180-220 of P10747) *Homo sapiens* |
| 11 | RSKRSRGGHSDYMNMTPRRPGPTRKHYQPYAPPRDFAAYRS | CD28 (LL to GG) *Homo sapiens* |
| 12 | KRGRKKLLYIFKQPFMRPVQTTQEEDGCSCRFPEEEEGGCEL | 4-1BB (amino acids 214-255 of Q07011.1) *Homo sapiens* |
| 13 | RVKFSRSADAPAYQQGQNQLYNELNLGRREEYDVLDKRRGRDPE MGGKPRRKNPQEGLYN ELQKDKMAEA YSEIGMKGER RRGKGHDGLY QGLSTATKDTYDALHMQALP PR | CD3 zeta *Homo sapiens* |
| 14 | RVKFSRSAEPPAYQQGQNQLYNELNLGRREEYDVLDKRRGRDPE MGGKPRRKNPQEGLYN ELQKDKMAEA YSEIGMKGER RRGKGHDGLY QGLSTATKDTYDALHMQALP PR | CD3 zeta *Homo sapiens* |
| 15 | RVKFSRSADAPAYKQGQNQLYNELNLGRREEYDVLDKRRGRDPE MGGKPRRKNPQEGLYN ELQKDKMAEA YSEIGMKGER RRGKGHDGLY QGLSTATKDTYDALHMQALP PR | CD3 zeta *Homo sapiens* |
| 16 | RKVCNGIGIGEFKDSLSINATNIKHFKNCTSISGDLHILPVAFRGDS FTHTPPLDPQELDILKTVKEITGFLLIQAWPENRTDLHAFENLEIIR GRTKQHGQFSLAVVSLNITSLGLRSLKEISDGDVIISGNKNLCYAN TINWKKLFGTSGQKTKIISNRGENSCKATGQVCHALCSPEGCWGP EPRDCVSCRNVSRGRECVDKCNLLEGEPREFVENSECIQCHPECLP QAMNITCTGRGPDNCIQCAHYIDGPHCVKTCPAGVMGENNTLVW KYADAGHVCHLCHPNCTYGCTGPGLEGCPTNGPKIPSIATGMVG ALLLLLVVALGIGLFM | tEGFR artificial |

What is claimed is:

1. A method of treating or delaying the development of cytokine release syndrome (CRS) in a subject, which has received a chimeric antigen receptor (CAR) T cell, the method comprising administering an agent comprising tocilizumab to the subject, wherein the subject (i) has a sign or symptom of grade 2 or lower CRS, and lacks a dose-limiting toxicity to the CAR T cell, or (ii) lacks a sign or symptom of grade 3 or higher CRS.

2. The method of claim 1, wherein the sign or symptom of grade 2 or lower CRS is selected from fever or hypotension or both.

3. The method of claim 2, wherein the fever comprises a temperature of at least 38.0° C., or is not reduced after treatment with an antipyretic.

4. The method of claim 2, wherein the sign or symptom of grade 2 or lower CRS is hypotension to a degree responsive to fluids or low dose pressor therapy.

5. The method of claim 1, wherein the agent is administered within 24 hours after onset of the sign or symptom of grade 2 or lower CRS.

6. The method of claim 5, wherein the agent is administered within 16 hours after onset of the sign or symptom of grade 2 or lower CRS.

7. The method of claim 1, wherein the subject lacks a sign or symptom of grade 2 or higher CRS.

8. The method of claim 1, wherein the subject has a leukemia or lymphoma.

9. The method of claim 1, wherein the CAR T cell comprises an anti-CD19 CAR.

10. The method of claim 1, further comprising administering a steroid to the subject.

11. The method of claim 1, wherein the subject has a sign or symptom of grade 2 or lower CRS, and lacks a dose-limiting toxicity to the CAR T cell.

12. The method of claim 1, wherein the subject lacks a sign or symptom of grade 3 or higher CRS.

13. The method of claim 2, wherein the sign or symptom of grade 2 or lower CRS is fever.

14. The method of claim 2, wherein the sign or symptom of grade 2 or lower CRS is hypotension.

15. The method of claim 3, wherein the fever comprises a temperature of at least 38.0° C.

16. The method of claim 3, wherein the fever is not reduced after administration of an antipyretic.

17. The method of claim 4, wherein the sign or symptom of grade 2 or lower CRS is hypotension to a degree responsive to fluids.

18. The method of claim 4, wherein the sign or symptom of grade 2 or lower CRS is hypotension to a degree responsive to low dose pressor therapy.

19. The method of claim 8, wherein the subject has a leukemia.

20. The method of claim 8, wherein the subject has a lymphoma.

* * * * *

UNITED STATES PATENT AND TRADEMARK OFFICE
CERTIFICATE OF CORRECTION

PATENT NO. : 12,098,208 B2
APPLICATION NO. : 18/329987
DATED : September 24, 2024
INVENTOR(S) : Michael C. Jensen It is certified that error appears in the above-identified patent and that said Letters Patent is hereby corrected as shown below:

On the Title Page

In Column 1, Line 3, Item (56) under Other Publications, delete "Ther ucleic Acids" and insert --Ther nucleic Acids--.

In Column 1, Line 10, Item (56) under Other Publications, delete "Opin Pedatr., 26" and insert --Curr Opin Pediatr., 26--.

In Column 1, Line 11, Item (56) under Other Publications, delete "the Plentivirus?" Mol" and insert --the Lentivirus?"Mol--.

In Column 1, Line 13, Item (56) under Other Publications, delete "and managemetn in" and insert --and management in--.

In Column 2, Line 62, Item (56) under Other Publications, delete "19-29z CART Cell" and insert --19-29z CAR T Cell--.

In Column 1, Line 2, Item (56) under Other Publications, delete "Gene Therpy,"Mol" and insert --Gene Therapy,"Mol--.

In Column 1, Line 38, Item (56) under Other Publications, delete "MRL-Ipr Mouse" and insert --MRL-lpr Mouse--.

In Column 1, Line 64, Item (56) under Other Publications, delete "of CART Cells" and insert --of CAR T Cells--.

In Column 2, Line 4, Item (56) under Other Publications, delete "J Imunol (2008)" and insert --J Immunol (2008)--.

Signed and Sealed this
Thirteenth Day of May, 2025

Coke Morgan Stewart
*Acting Director of the United States Patent and Trademark Office*

In Column 2, Line 6, Item (56) under Other Publications, delete "8(6):ofab161." and insert --8(6):of ab161.--.

In Column 2, Line 25, Item (56) under Other Publications, delete "refractory chromic lymphocytic" and insert --refractory chronic lymphocytic--.

In the Drawings

On Sheet 2 of 6, Fig. 1B, Line 7 (Approx.), delete "tociluzimab" and insert --tocilizumab--.

In the Specification

In Column 1, Line 10, delete "No. 11/518,814 issued" and insert --No. 11,518,814 issued--.

In Column 4, Line 11, delete "CCR5, TNFalpha, TNFR1," and insert --CCR5, TNF alpha, TNFR1,--.

In Column 6, Line 58, delete "CCR5, TNFalpha, TNFR1," and insert --CCR5, TNF alpha, TNFR1,--.

In Column 8, Line 33, delete "oxygen (PO2) levels" and insert --oxygen ($PO_2$) levels--.

In Column 8, Line 56, delete "to a the administration" and insert --to the administration--.

In Column 12, Line 15, delete "CCR4, MIP1, CCR5, TNFalpha, TNFR1," and insert --CCR4, MIP1β, CCR5, TNF alpha, TNFR1,--.

In Column 13, Line 51, delete "peripheral bloodin subjects" and insert --peripheral blood in subjects--.

In Column 15, Line 15 (Approx.), delete "exhaustion, anergy, terminal" and insert --exhaustion, energy, terminal--.

In Column 17, Line 36 (Approx.), delete "are IL-10, IL-6," and insert --are IL-1β, IL-6,--.

In Column 18, Line 27, delete "Flt-3L, fracktalkine, and" and insert --Flt-3L, fractalkine, and--.

In Column 18, Line 31 (Approx.), delete "Flt-3L, fracktalkine, and" and insert --Flt-3L, fractalkine, and--.

In Column 18, Line 35 (Approx.), delete "hypoxia (PO2 <90%) or" and insert --hypoxia ($PO_2$ <90%) or--.

In Column 18, Line 51 (Approx.), delete "Flt-3L, fracktalkine, and" and insert --Flt-3L, fractalkine, and--.

In Column 18, Line 56 (Approx.), delete "oxygen (PO2) levels" and insert --oxygen ($PO_2$) levels--.

CERTIFICATE OF CORRECTION (continued)
U.S. Pat. No. 12,098,208 B2

In Column 20, Line 19 (Approx.), delete "Nabumetone, Phenaxone, antipyrine," and insert --Nabumetone, Phenazone, antipyrine,--.

In Column 20, Lines 49-50, delete "severe neurotoxity, is" and insert --severe neurotoxicity, is--.

In Column 22, Line 2, delete "neuropathy, dysethesia, neuralgia" and insert --neuropathy, dysesthesia, neuralgia--.

In Column 24, Line 34, delete "fetal acethycholine e receptor," and insert --fetal acetylcholine receptor,--.

In Column 26, Line 18, delete "receptor 7, CD8," and insert --receptor γ, CD8,--.

In Column 26, Line 20, delete "CD3-zeta (CD3-ζ) or" and insert --CD3-zeta (CD3ζ) or--.

In Column 26, Line 21, delete "receptor 7 and" and insert --receptor γ and--.

In Column 29, Line 4, delete "No. PO1747.1) or" and insert --No. P01747.1) or--.

In Column 37, Line 30, delete "as Dynalbeads or" and insert --as Dynabeads or--.

In Column 43, Line 25, delete "hypoxanthine phosphribosyltransferase (HPRT)" and insert --hypoxanthine phosphoribosyltransferase (HPRT)--.

In Column 47, Line 22, delete "fetal acethycholine e receptor," and insert --fetal acetylcholine receptor,--.

In Column 47, Lines 59-60, delete "injection, subconjectval injection, subconjuntival injection," and insert --injection, subconjunctival injection,--.

In Column 52, Line 50, delete "1:1.8, 1:1.9:1:2," and insert --1:1.8, 1:1.9, 1:2,--.

In Column 53, Line 59, delete "embodiments, vassopressors or" and insert --embodiments, vasopressors or--.

In Column 55, Line 33, delete "to: alclomethasones, algestones," and insert --to: alclometasones, algestones,--.

In Column 55, Line 41, delete "desonides, desoximethasones, dexamethasones" and insert --desonides, desoximetasone, dexamethasones--.

In Column 55, Lines 44-45, delete "enoxolones, fluazacorts, flucloronides, fludrocortisones" and insert --enoxolones, flazacorts, fluorides, fludrocortisones--.

In Column 55, Line 49, delete "acetate), fluperolones (e.g.," and insert --acetate), fluoroquinolones (e.g.,--.

CERTIFICATE OF CORRECTION (continued)
U.S. Pat. No. 12,098,208 B2

In Column 55, Line 52, delete "halometasones, halopredones, hydrocortamates," and insert --halometasones, haloperidols, hydrocortamates,--.

In Column 55, Line 67, delete "prednisolone acetate; prednisolone" and insert --prednisolone acetate, prednisolone--.

In Column 56, Line 4, delete "prednisones, prednivals, prednylidenes," and insert --prednisones, predniwels, prednylidenes,--.

In Column 57, Line 34 (Approx.), delete "administration" and insert --administration.--.

In Column 58, Lines 62-63, delete "injection, subconjectval injection, subconjuntival injection," and insert --injection, subconjunctival injection,--.

In Column 60, Line 12 (Approx.), delete "an IFN-7 receptor" and insert --an IFN-γ receptor--.

In Column 61, Line 50, delete "example, p-toluenesulphonic acid." and insert --example, p- toluenesulfonic acid.--.

In Column 62, Lines 24-25, delete "injection, subconjectval injection, subconjuntival injection," and insert --injection, subconjunctival injection,--.

In Column 63, Line 9, delete "saline, polyoi (for" and insert --saline, polyol (for--.

In Column 65, Line 13, delete "of embodiment 1-7," and insert --of embodiments 1-7,--.

In Column 65, Line 59, delete "CCR5, TNFalpha, TNFR1," and insert --CCR5, TNF alpha, TNFR1,--.

In Column 66, Line 13, delete "of embodiment 1-21," and insert --of embodiments 1-21,--.

In Column 68, Line 57, delete "CCR5, TNFalpha, TNFR1," and insert --CCR5, TNF alpha, TNFR1,--.

In Column 69, Line 59, delete "of any of any of embodiments" and insert --of any of embodiments--.

In Column 70, Line 57, delete "of embodiment 1-75," and insert --of embodiments 1-75,--.

In Column 74, Line 21, delete "CCR5, TNFalpha, TNFR1," and insert --CCR5, TNF alpha, TNFR1,--.

In Columns 79-80, Line 4 (Approx.), (TABLE 5), delete "applasia" and insert --aplasia--.

SEQUENCE LISTING

```
Sequence total quantity: 16
SEQ ID NO: 1              moltype = AA   length = 12
FEATURE                   Location/Qualifiers
REGION                    1..12
                          note = Spacer (IgG4hinge)
source                    1..12
                          mol_type = protein
```

```
                            organism = Homo sapiens
SEQUENCE: 1
ESKYGPPCPP CP                                                            12

SEQ ID NO: 2            moltype = DNA   length = 36
FEATURE                 Location/Qualifiers
misc_feature            1..36
                        note = Spacer (IgG4hinge)
source                  1..36
                        mol_type = other DNA
                        organism = Homo sapiens
SEQUENCE: 2
gaatctaagt acggaccgcc ctgcccccct tgccct                                  36

SEQ ID NO: 3            moltype = AA   length = 135
FEATURE                 Location/Qualifiers
REGION                  1..135
                        note = Hinge-CH3 spacer
source                  1..135
                        mol_type = protein
                        organism = Homo sapiens
SEQUENCE: 3
ESKYGPPCPP CPGQPRESKY GPPCPPCPGQ PREPQVYTLP PSQEEMTKNQ VSLTCLVKGF         60
YPSDIAVEWE SNGQPENNYK TTPPVLDSDG SFFLYSRLTV DKSRWQEGNV FSCSVMHEAL        120
HNHYTQKSLS LSLGK                                                        135

SEQ ID NO: 4            moltype = AA   length = 229
FEATURE                 Location/Qualifiers
REGION                  1..229
                        note = Hinge-CH2-CH3 spacer
source                  1..229
                        mol_type = protein
                        organism = Homo sapiens
SEQUENCE: 4
ESKYGPPCPP CPAPEFLGGP SVFLFPPKPK DTLMISRTPE VTCVVVDVSQ EDPEVQFNWY         60
VDGVEVHNAK TKPREEQFNS TYRVVSVLTV LHQDWLNGKE YKCKVSNKGL PSSIEKTISK        120
AKGQPREPQV YTLPPSQEEM TKNQVSLTCL VKGFYPSDIA VEWESNGQPE NNYKTTPPVL        180
DSDGSFFLYS RLTVDKSRWQ EGNVFSCSVM HEALHNHYTQ KSLSLSLGK                   229

SEQ ID NO: 5            moltype = AA   length = 282
FEATURE                 Location/Qualifiers
REGION                  1..282
                        note = IgD-hinge-Fc
source                  1..282
                        mol_type = protein
                        organism = Homo sapiens
SEQUENCE: 5
RWPESPKAQA SSVPTAQPQA EGSLAKATTA PATTRNTGRG GEEKKKEKEK EEQEERETKT         60
PECPSHTQPL GVYLLTPAVQ DLWLRDKATF TCFVVGSDLK DAHLTWEVAG KVPTGVEEG        120
LLERHSNGSQ SQHSRLTLPR SLWNAGTSVT CTLNHPSLPP QRLMALREPA AQAPVKLSLN       180
LLASSDPPEA ASWLLCEVSG FSPPNILLMW LEDQREVNTS GFAPARPPPQ PGSTTFWAWS       240
VLRVPAPPSP QPATYTCVVS HEDSRTLLNA SRSLEVSYVT DH                          282

SEQ ID NO: 6            moltype = AA   length = 24
FEATURE                 Location/Qualifiers
REGION                  1..24
                        note = T2A
source                  1..24
                        mol_type = protein
                        organism = synthetic construct
SEQUENCE: 6
LEGGGEGRGS LLTCGDVEEN PGPR                                               24

SEQ ID NO: 7            moltype = AA   length = 357
FEATURE                 Location/Qualifiers
REGION                  1..357
                        note = tEGFR
source                  1..357
                        mol_type = protein
                        organism = synthetic construct
SEQUENCE: 7
MLLLVTSLLL CELPHPAFLL IPRKVCNGIG IGEFKDSLSI NATNIKHFKN CTSISGDLHI         60
LPVAFRGDSF THTPPLDPQE LDILKTVKEI TGFLLIQAWP ENRTDLHAFE NLEIIRGRTK        120
QHGQFSLAVV SLNITSLGLR SLKEISDGDV IISGNKNLCY ANTINWKKLF GTSGQKTKII        180
SNRGENSCKA TGQVCHALCS PEGCWGPEPR DCVSCRNVSR GRECVDKCNL LEGEPREFVE        240
NSECIQCHPE CLPQAMNITC TGRGPDNCIQ CAHYIDGPHC VKTCPAGVMG ENNTLVWKYA        300
DAGHVCHLCH PNCTYGCTGP GLEGCPTNGP KIPSIATGMV GALLLLLVVA LGIGLFM           357

SEQ ID NO: 8            moltype = AA   length = 27
```

```
FEATURE                     Location/Qualifiers
REGION                      1..27
                            note = CD28 (amino acids 153-179 of Accession No. P10747)
source                      1..27
                            mol_type = protein
                            organism = Homo sapiens
SEQUENCE: 8
FWVLVVVGGV LACYSLLVTV AFIIFWV                                         27

SEQ ID NO: 9                moltype = AA   length = 66
FEATURE                     Location/Qualifiers
REGION                      1..66
                            note = CD28 (amino acids 114-179 of Accession No. P10747)
source                      1..66
                            mol_type = protein
                            organism = Homo sapiens
SEQUENCE: 9
IEVMYPPPYL DNEKSNGTII HVKGKHLCPS PLFPGPSKPF WVLVVVGGVL ACYSLLVTVA     60
FIIFWV                                                                66

SEQ ID NO: 10               moltype = AA   length = 41
FEATURE                     Location/Qualifiers
REGION                      1..41
                            note = CD28 (amino acids 180-220 of P10747)
source                      1..41
                            mol_type = protein
                            organism = Homo sapiens
SEQUENCE: 10
RSKRSRLLHS DYMNMTPRRP GPTRKHYQPY APPRDFAAYR S                         41

SEQ ID NO: 11               moltype = AA   length = 41
FEATURE                     Location/Qualifiers
REGION                      1..41
                            note = CD28 (LL to GG)
source                      1..41
                            mol_type = protein
                            organism = synthetic construct
SEQUENCE: 11
RSKRSRGGHS DYMNMTPRRP GPTRKHYQPY APPRDFAAYR S                         41

SEQ ID NO: 12               moltype = AA   length = 42
FEATURE                     Location/Qualifiers
REGION                      1..42
                            note = 4-1BB (amino acids 214-255 of Q07011.1)
source                      1..42
                            mol_type = protein
                            organism = Homo sapiens
SEQUENCE: 12
KRGRKKLLYI FKQPFMRPVQ TTQEEDGCSC RFPEEEEGGC EL                        42

SEQ ID NO: 13               moltype = AA   length = 112
FEATURE                     Location/Qualifiers
REGION                      1..112
                            note = CD3 zeta
source                      1..112
                            mol_type = protein
                            organism = Homo sapiens
SEQUENCE: 13
RVKFSRSADA PAYQQGQNQL YNELNLGRRE EYDVLDKRRG RDPEMGGKPR RKNPQEGLYN     60
ELQKDKMAEA YSEIGMKGER RRGKGHDGLY QGLSTATKDT YDALHMQALP PR             112

SEQ ID NO: 14               moltype = AA   length = 112
FEATURE                     Location/Qualifiers
REGION                      1..112
                            note = CD3 zeta
source                      1..112
                            mol_type = protein
                            organism = Homo sapiens
SEQUENCE: 14
RVKFSRSAEP PAYQQGQNQL YNELNLGRRE EYDVLDKRRG RDPEMGGKPR RKNPQEGLYN     60
ELQKDKMAEA YSEIGMKGER RRGKGHDGLY QGLSTATKDT YDALHMQALP PR             112

SEQ ID NO: 15               moltype = AA   length = 112
FEATURE                     Location/Qualifiers
REGION                      1..112
                            note = CD3 zeta
source                      1..112
                            mol_type = protein
                            organism = Homo sapiens
```

```
SEQUENCE: 15
RVKFSRSADA PAYKQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 16           moltype = AA  length = 335
FEATURE                 Location/Qualifiers
REGION                  1..335
                        note = tEGFR
source                  1..335
                        mol_type = protein
                        organism = synthetic construct
SEQUENCE: 16
RKVCNGIGIG EFKDSLSINA TNIKHFKNCT SISGDLHILP VAFRGDSFTH TPPLDPQELD    60
ILKTVKEITG FLLIQAWPEN RTDLHAFENL EIIRGRTKQH GQFSLAVVSL NITSLGLRSL   120
KEISDGDVII SGNKNLCYAN TINWKKLFGT SGQKTKIISN RGENSCKATG QVCHALCSPE   180
GCWGPEPRDC VSCRNVSRGR ECVDKCNLLE GEPREFVENS ECIQCHPECL PQAMNITCTG   240
RGPDNCIQCA HYIDGPHCVK TCPAGVMGEN NTLVWKYADA GHVCHLCHPN CTYGCTGPGL   300
EGCPTNGPKI PSIATGMVGA LLLLLVVALG IGLFM                             335
```